United States Patent
DeMattei et al.

(10) Patent No.: US 9,024,040 B2
(45) Date of Patent: May 5, 2015

(54) PROCESSES FOR PREPARING BENZIMIDAZOLE COMPOUNDS

(75) Inventors: John DeMattei, San Diego, CO (US); Sagar Shakya, San Diego, CO (US); Anthony D. Piscopio, Boulder, CO (US); Bruno P. Hache, Boulder, CO (US); Matthew Charles Evans, Macclesfield (GB); James Gair Ford, Macclesfield (GB); Simon Mark Pointon, Macclesfield (GB); Koen Peeters, Mont-Saint-Guibert (BE); Timothy John Lilley, Macclesfield (GB); John Leonard, Macclesfield (GB)

(73) Assignee: Array Biopharma Inc., Boulder, CO (US)

( * ) Notice: Subject to any disclaimer, the term of this patent is extended or adjusted under 35 U.S.C. 154(b) by 0 days.

(21) Appl. No.: 13/614,941

(22) Filed: Sep. 13, 2012

(65) Prior Publication Data

US 2013/0245279 A1     Sep. 19, 2013

Related U.S. Application Data

(62) Division of application No. 13/229,459, filed on Sep. 9, 2011, now Pat. No. 8,383,832, which is a division of application No. 11/993,745, filed as application No. PCT/US2006/024084 on Jun. 21, 2006, now Pat. No. 8,039,637.

(60) Provisional application No. 60/693,270, filed on Jun. 23, 2005.

(51) Int. Cl.
| | | |
|---|---|---|
| *C07D 235/00* | (2006.01) | |
| *C07D 403/02* | (2006.01) | |
| *C07D 235/18* | (2006.01) | |
| *C07D 235/06* | (2006.01) | |
| *C07C 205/58* | (2006.01) | |
| *C07C 229/60* | (2006.01) | |
| *C07C 201/08* | (2006.01) | |
| *C07C 227/04* | (2006.01) | |
| *C07C 227/08* | (2006.01) | |
| *C07C 227/18* | (2006.01) | |

(52) U.S. Cl.
CPC ............ *C07D 235/06* (2013.01); *C07C 205/58* (2013.01); *C07C 229/60* (2013.01); *C07C 201/08* (2013.01); *C07C 227/04* (2013.01); *C07C 227/08* (2013.01); *C07C 227/18* (2013.01)

(58) Field of Classification Search
USPC ................ 548/304.4, 304.7, 306.1, 310.7
See application file for complete search history.

(56) References Cited

U.S. PATENT DOCUMENTS

| | | | |
|---|---|---|---|
| 3,959,261 | A | 5/1976 | Lerch et al. |
| 4,870,074 | A | 9/1989 | Kon et al. |
| 5,597,823 | A | 1/1997 | Meyer et al. |
| 5,817,823 | A | 10/1998 | Hong et al. |
| 6,087,368 | A | 7/2000 | Macor et al. |
| 6,544,985 | B2 | 4/2003 | Adam et al. |
| 6,894,068 | B2 | 5/2005 | Michejda et al. |
| 7,160,915 | B2 | 1/2007 | Barrett et al. |
| 7,632,865 | B2 | 12/2009 | Kato et al. |
| 2003/0232869 | A1 | 12/2003 | Wallace et al. |
| 2005/0187231 | A1 | 8/2005 | Lee et al. |

FOREIGN PATENT DOCUMENTS

| | | |
|---|---|---|
| DE | 2334973 A1 | 1/1975 |
| EP | 556393 A1 | 8/1993 |
| EP | 676397 A1 | 10/1995 |
| EP | 757985 A1 | 12/1997 |
| JP | 6332129 | 12/1994 |
| WO | 9220320 A1 | 11/1992 |
| WO | 9622992 A1 | 8/1996 |
| WO | 9964004 A1 | 12/1999 |
| WO | 0042022 A1 | 7/2000 |
| WO | 0105390 A2 | 1/2001 |

(Continued)

OTHER PUBLICATIONS

Abuzar, Syed et al, Synthesis of N-Aryl- & N-Heteroaryl-benzimidazoles as Potential Anthelmintics, Indian Journal of Chemistry. Section B: Organic and Medicinal Chemistry, Council of Scientific and Industrial Research, Jul. 1980, 599-600, vol. 19B.

Blanksma J.J., Preparation of Halogen Derivatives of Benzaldehyde, Chemisch Weekblad, Sigma Chemie, Den Haag, NL, Jan. 1, 1912, 862-870, vol. 9; 2 supplementary pages from SciFinder®.

Carter, Robert E. et al, The synthesis of some highly substituted benzene derivatives and several new biphenyls, Arkiv Foer, Jan. 1, 1967, 257-262, vol. 27 No. 23.

(Continued)

*Primary Examiner* — Nyeemah A Grazier
(74) *Attorney, Agent, or Firm* — Sarah S. Mastous; Array BioPharma Inc.

(57) ABSTRACT

Provided are processes for the preparation of benzimidazole structures having Formula VIIIb-1:

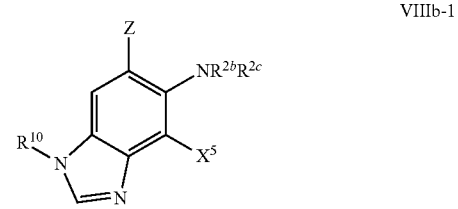

and salts and solvates thereof, wherein Z, $X^5$, $R^{2b}$, $R^{2c}$ and $R^{10}$ are as defined herein. Compounds of Formula VIIIb-1 are useful for the preparation of benzimidazole derivatives.

11 Claims, 10 Drawing Sheets

(56) References Cited

FOREIGN PATENT DOCUMENTS

| WO | 0105393 A2 | 1/2001 |
| WO | 02083622 A2 | 10/2002 |
| WO | 03032984 A1 | 4/2003 |
| WO | 03077855 A2 | 9/2003 |
| WO | 2004106348 A1 | 12/2004 |
| WO | 2005009975 A2 | 2/2005 |
| WO | 2005077895 A1 | 8/2005 |
| WO | 2005080352 A2 | 9/2005 |

OTHER PUBLICATIONS

Database Registry (On-line), Chemical Abstracts Service, Columbus, OH, Nov. 16, 1984, Database accession No. 69217-32-9.

Ellis, G.P. et al., "One-Step Synthesis and Spectral Study of Some 1-Methylbenzimidazoles, including Use of a Lanthanide Shift Reagent", J.C.S. Perkin 1, 1974, pp. 903-906.

Ettel, Viktor et al, Chromatographic Separation of Mixtures of Nitro Compounds, Chemick Listy—J. Chem., Czech Chemical Society, Jan. 1, 1958, 623-630, vol. 52; and 3 supplementary pages from SciFinder®.

Extended European Search Report, EP Application No. 06 785 244.2 dated Sep. 29, 2010.

Goldstein, Henri et al, Sur l'acide 4, 5-dinitro-2-chloro-benzoique, Helvetica Chimica Acta, 1937, 1407-1412, vol. 20; and 1 supplementary page from SciFinder®.

Goldstein Henri et al, Sur L'Acide Dinitro-4,5-Anthranilique, Helvetic Chimica Acta, 1951, 1860-1868, vol. 34; and 2 supplementary pages from SciFinder®.

Hartwig, John F., Transition Metal Catalyzed Synthesis of Arylamines and Aryl Ethers from Aryl Halides and Triflates: Scope and Mechanism, Angew. Chem. Int. Ed., Jan. 1, 1998, 2046-2067, vol. 37.

Int'l Search Report and Written Opinion corresponding to PCT Application No. PCT/US06/24084.

Keyser et al., "lin-Benzoguanine. Synthesis by Two Independent Methods", J. Org. Chem. vol. 41, No. 22, pp. 3529-3532, 1976.

Keyser, Gene E. et al, Synthesis of Iin-Benzoinosine, Iin-Benzoxanthosine, and Iin-Benzoguanosine, J. Org. Chem., Aug. 1979, 2989-2994, vol. 44. No. 17.

Kumar, Shiv et al, Possible Anthelmintic Agents: Syntheses of Various Imidazoquinazo-Iinone Carbamates, Indian Journal of Chemistry, Dec. 1981, 1068-1071, vol. 20B.

Leonard, Nelson J. et al, Linear Benzoadenine. A Stretched-Out Analog of Adenine, J. Org. Chem., Feb. 1975, 356-363, vol. 40 No. 3.

Milata V. et al., "Simple and Convenient Procedure for the Preparation of 1-Methyl-4-Nitrobenzimidazole", Department of Organic Chemistry, Faculty of Chemical Technology, Slovak Technical University, vol. 25, No. 6, 1993.

Morgan, G.T. et al., "Bases derived from 2-Chloro-4:5-dinitrotoluene", CLXXX.—Ortho-Chlorodinitrotoluenes. Part III. pp. 1537-1546, (1921).

Rotella, et al., "N-3-Substituted Imidazoquinazolinones: Potent and Selective PDE5 Inhibitors as Potential Agents for Treatment of Erectile Dysfunction", J. Med. Chem. (2000), 43(26): 1257-1263.

Rotella, et al., "Optimization of Substituted N-3-Benzylimidazoquinazolinone Sulfonamides as Potent and Selctive PDE5 Inhibitors", J. Med. Chem. (2000), 43(26): 5037-5043.

Schneller, Stewart W. et al, The Synthesis of "Stretched-Out" Analogs of Lumazine, 6,7-Dimethyllumazine and 2-Amino-5,6,7,8-tetra-hydro-6,7-dimethyl-4-pteridinone (1,2), J. Heterocyclic Chem., May 1981, 539-542, vol. 18.

Zefirov, N.S. et al., "Solid-Phase Synthesis of 1,2-Benzophenazine and Some Fused Imidazole Derivatives", Chemistry Department of the Moscow State University, Moscow, Russia, 4 pages, (1996).

PROCESSES FOR PREPARING BENZIMIDAZOLE COMPOUNDS

RELATED APPLICATION

The present application is a divisional of U.S. patent application Ser. No. 13/229,459, filed Sep. 9, 2011 now U.S. Pat. No. 8,383,832, which is a divisional of U.S. patent application Ser. No. 11/993,745, filed Jan. 26, 2010 now U.S. Pat. No. 8,039,637, which is a Section 371(e) filing from PCT/US06/24084, filed Jun. 21, 2006, which claims priority of U.S. Provisional Application Ser. No. 60/693,270 filed Jun. 23, 2005, each of which is incorporated herein in its entirety by reference.

BACKGROUND OF THE INVENTION

1. Field of the Invention

This invention relates to processes for the preparation of heterocyclic compounds. More specifically, this invention relates to the synthesis of compounds that can be used to prepare pharmaceutical agents such as benzimidazole derivatives. This invention further includes intermediate compounds obtained during the synthesis of the heterocyclic compounds according to this invention and to the methods of preparation thereof.

2. Description of the State of the Art

Benzimidazole derivatives have been investigated as therapeutics for treating cancers, viral infections, and diseases and pathological conditions involving inflammation and have been disclosed in a number of patents and publications in the last several years, including U.S. Patent Publication Nos. 2003/0232869, 2004/0116710, and 2003/0216460; U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

In particular, WO 03/077914 describes the synthesis of the sodium salt of a benzimidazole derivative 11 from 2,3,4-trifluorobenzoic acid in 11 linear steps as illustrated in Scheme 1. This route is not only very long in terms of the number of steps, but also includes a number of chemical transformations that could be hazardous to carry out on a manufacturing scale, and/or produce levels of by-products that would not be acceptable in a final active pharmaceutical ingredient (API). It will be appreciated by those skilled in the art that for a process to be suitable for industrial application it should be (i) amenable to being performed on large scale, (ii) have minimal environmental impact (for example in terms of amount of raw materials required and/or the amount of waste produced), (iii) safe (for example, use materials of low toxicity that do not produce toxic waste), and (iv) as low in cost as possible (for example, by being a higher yielding and more convergent synthesis). Since heterocyclic compounds such as benzimidazoles are potentially useful as therapeutics, there is an on-going need for a more efficient synthetic route for the production of benzimidazole derivatives that is more amenable to or suitable for large-scale manufacture.

Scheme 1

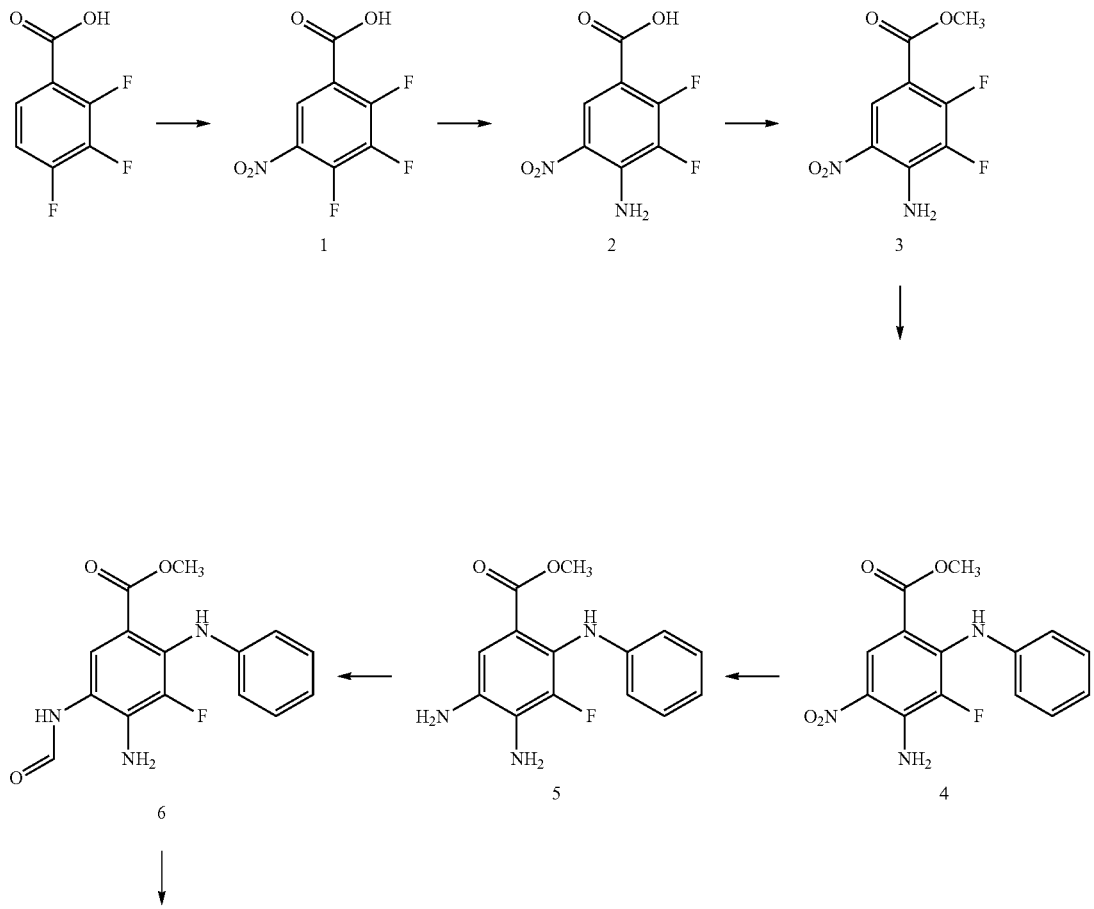

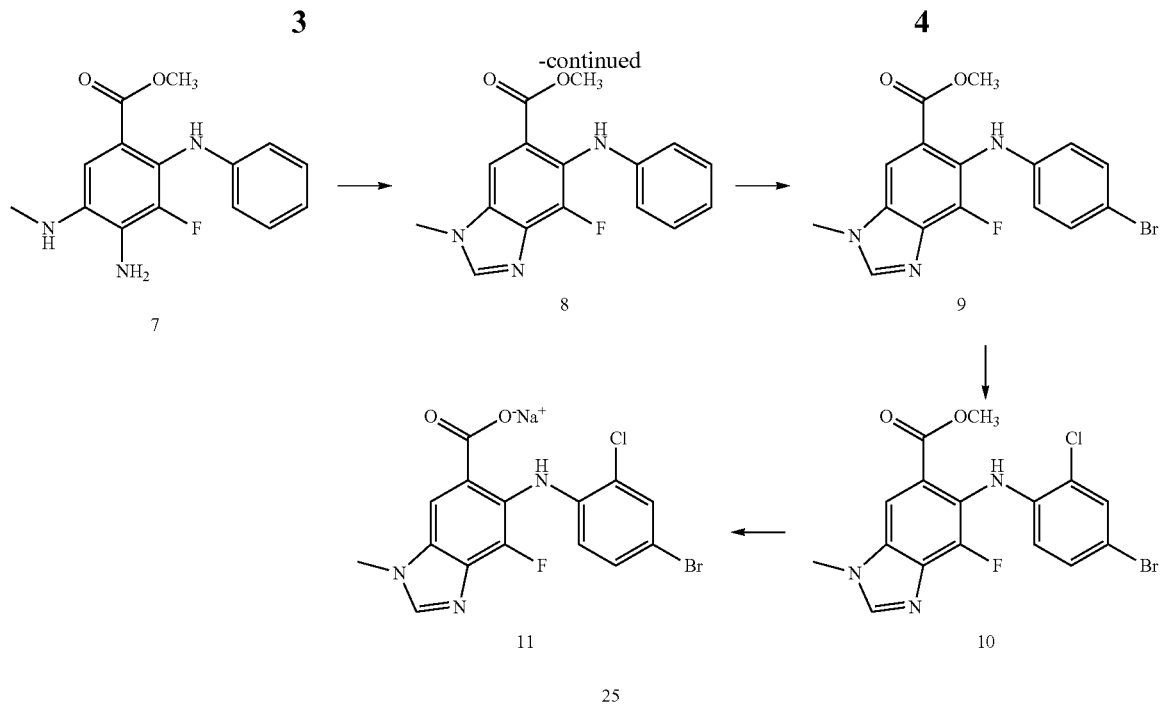

SUMMARY OF THE INVENTION

In general, the present invention provides methods for preparing heterocyclic compounds and their synthetic intermediates, which are useful for the production of therapeutic compounds such as benzimidazole derivatives.

According to one aspect of the present invention, methods are provided for the preparation of compounds of the general Formulas Ia-1, Ia-2, Ib-1, Ib-2 and Ic-1 and their synthetic intermediates

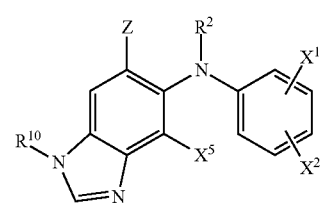

Ia-1

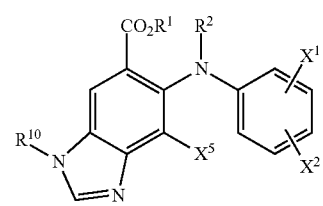

Ia-2

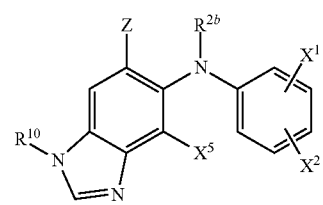

Ib-1

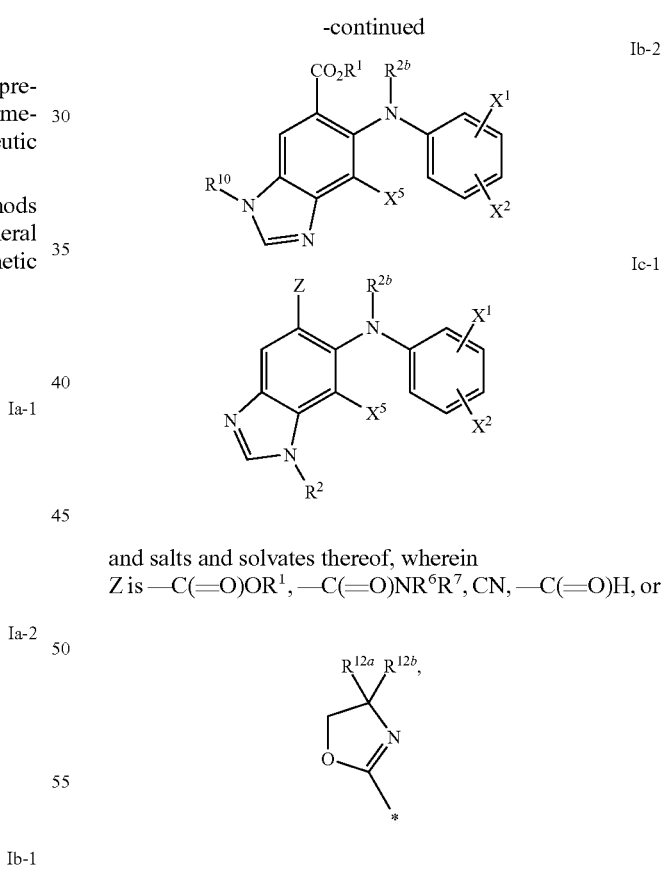

and salts and solvates thereof, wherein
Z is —C(=O)OR$^1$, —C(=O)NR$^6$R$^7$, CN, —C(=O)H, or or a moiety that can be transformed into any one of said Z groups, for example through hydrolysis;
R$^1$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, $C_1$-$C_4$ alkyl, $C_2$-$C_4$ alkenyl, $C_2$-$C_4$ alkynyl, $C_3$-$C_6$ cycloalkyl, and $C_3$-$C_6$ heterocycloalkyl;

$R^2$ and $R^{2b}$ are independently hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —$COR^6$, —$C(O)OR^6$ or —$C(O)NR^6R^7$, wherein said alkyl, alkenyl, alkynyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl, wherein for Formula Ic-1, $R^2$ is not hydrogen;

$X^1$ and $X^2$ are independently selected from hydrogen, F, Cl, Br, I, $OR^8$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl and $C_1$-$C_{10}$ thioalkyl, wherein said alkyl, alkenyl, alkynyl, cycloalkyl, cycloalkylalkyl and thioalkyl portions are optionally substituted with one or more groups independently selected from oxo, halogen, cyano, nitro, trifluoromethyl, difluoromethoxy, trifluoromethoxy and azido;

$X^5$ is H, F, Cl, Br, I or $C_1$-$C_6$ alkyl;

$R^6$ and $R^7$ are independently hydrogen, trifluoromethyl, —$OR^8$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^6$ and $R^7$ together with the atom to which they are attached form a 4 to 10 membered heteroaryl or heterocyclic ring, wherein said heteroaryl and heterocyclic rings are optionally substituted with one or more groups independently selected from halogen, trifluoromethyl, difluoromethoxy, trifluoromethoxy and $OR^8$;

$R^8$ is hydrogen, $C_1$-$C_{10}$ alkyl, $C_2$-$C_{10}$ alkenyl, aryl or arylalkyl, wherein said alkyl, alkenyl, aryl and arylalkyl are optionally substituted with one or more groups independently selected from OH, —O—($C_1$-$C_{10}$-alkyl) and —O—($C_1$-$C_{10}$-alkenyl);

$R^{10}$ is hydrogen, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$; and $R^{12a}$ and $R^{12b}$ are independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl and heteroarylalkyl, or $R^{12a}$ and $R^{12b}$ together with the atom to which they are attached form a 4 to 10 membered carbocyclic, heteroaryl or heterocyclic ring.

More specifically, one embodiment of the present invention provides a process, referred to herein as Method 1, for preparing N-3 benzimidazole compounds represented by Formula Ia-1 and their synthetic intermediates

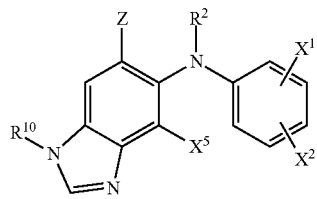

Ia-1 and salts and solvates thereof, wherein Z, $R^2$, $R^{10}$, $X^1$, $X^2$ and $X^5$ are as defined herein, said method comprising:

nitrating a compound having the Formula

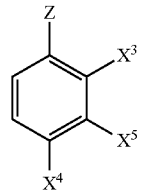

wherein $X^3$ and $X^4$ are independently F, Cl, Br, I or a sulfonate ester, and Z and $X^5$ are as defined herein, to provide a compound of Formula II

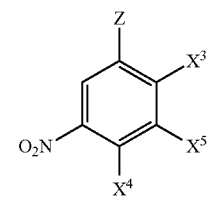

II wherein $X^3$, $X^4$, $X^5$ and Z are as defined herein;

treating said compound of Formula II, optionally at elevated temperature and/or pressure, with two or more equivalents of (i) a reagent that contains or generates ammonia, (ii) a primary or secondary amine other than an aromatic amine or (iii) a reagent that delivers a group that can subsequently be converted into an amine to provide a compound of Formula VI-11, or treating said compound of Formula II with (iv) two or more equivalents of a metal azide, optionally at elevated temperatures and/or pressure, to provide a compound of Formula VI-12

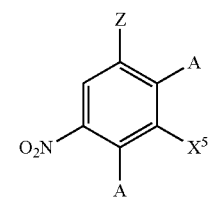

VI-11: A = $NR^2R^{2a}$
VI-12: A = $N_3$ wherein $X^5$, $R^2$ and Z are as defined herein, and $R^{2a}$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^6$, —$C(O)OR^6$, —$C(O)NR^6R^7$, —$OR^1$ or —$NHR^1$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl;

reducing said compound of Formula VI-11 or VI-12 to provide a compound of Formula VIIa-1

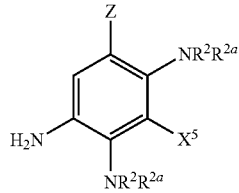

VIIa-1 wherein $X^5$, $R^2$, $R^{2a}$ and Z are as defined herein, and wherein when A of Formula VI-11 or VI-12 is —NH-benzyl, —NHOR$^1$, —NHNHR$^1$ or N$_3$, then $R^2$ and $R^{2a}$ of Formula VIIa-1 are hydrogen;

when $R^{2a}$ is hydrogen, cyclizing said compound of Formula VIIa-1 to provide a compound of Formula VIIIa-1

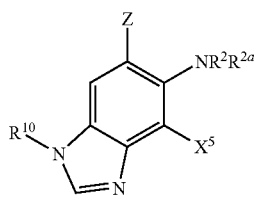

VIIIa-1 wherein Z, $R^2$, $R^{2a}$, $R^{10}$ and $X^5$ are as defined herein; and when $R^{2a}$ is hydrogen, coupling said compound of Formula VIIIa-1 with a reagent having the formula

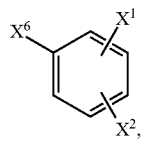

wherein $X^1$ and $X^2$ are as defined herein and $X^6$ is F, Cl, Br, I, —OSO$_2$CF$_3$, alkyl sulfonate, aryl sulfonate, alkylaryl sulfonate, —B(OR$^8$)$_2$, —BF$_3$ or —Bi(R$^1$)$_2$, optionally either (i) at elevated temperature and optionally in the presence of a base, or (ii) in the presence of a metal-based catalyst and a base, to provide said compound of Formula Ia-1.

In a particular embodiment of Method 1, there is provided a process for preparing a compound of Formula Ia-1

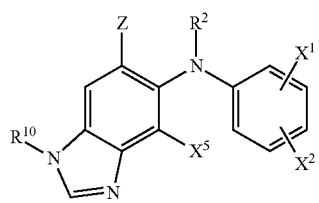

Ia-1 and salts and solvates thereof, wherein:

Z is —C(=O)OR$^1$, R$^1$ is C$_1$-C$_{10}$ alkyl, and R$^2$, R$^{10}$, X$^1$, X$^2$ and X$^5$ are as defined herein, said process comprising:

i) nitrating a compound having the Formula

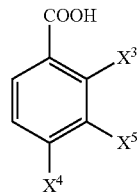

wherein $X^3$ and $X^4$ are independently F, Cl, Br, I, or a sulfonate ester and $X^5$ is as defined herein, to provide a compound of Formula II

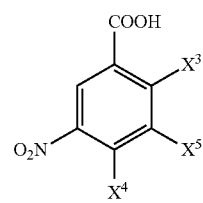

II wherein $X^3$, $X^4$ and $X^5$ are as defined herein;

ii) reacting the compound of Formula II with a compound of formula R$^1$OH, wherein R$^1$ is C$_1$-C$_{10}$ alkyl, to form the corresponding ester having the formula

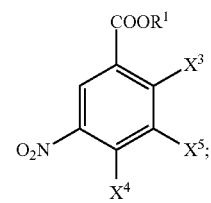

wherein R$^1$ is C$_1$-C$_{10}$ alkyl and X$^3$, X$^4$ and X$^5$ are as defined herein;

iii) reacting the ester from step (ii) with two or more equivalents of a reagent that generates ammonia to form a compound of Formula VI-11

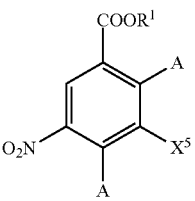

VI-11: A = NR$^3$R$^{3a}$ wherein R$^{2a}$ is hydrogen, R$^1$ is C$_1$-C$_{10}$ alkyl and R$^2$ and X$^5$ are as defined herein;

iv) reducing said compound of Formula VI-11 to provide a compound of Formula VIIa-1

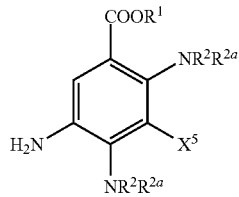

VIIa-1 wherein $R^{2a}$ is hydrogen, $R^1$ is $C_1$-$C_{10}$ alkyl and $R^2$ and $X^5$ are as defined herein;

v) cyclizing said compound of Formula VIIa-1 to provide a compound of Formula VIIIa-1

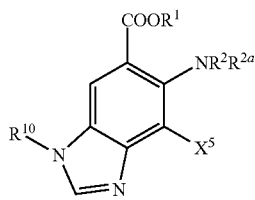

VIIIa-1 wherein $R^{2a}$ is hydrogen, $R^1$ is $C_1$-$C_{10}$ alkyl, and $R^2$, $R^{10}$ and $X^5$ are as defined herein; and vi) coupling said compound of Formula VIIIa-1 with a reagent having the Formula

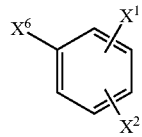

wherein $X^1$ and $X^2$ are as defined herein and $X^6$ is F, Cl, Br, I, —OSO$_2$CF$_3$, alkyl sulfonate, aryl sulfonate, alkylaryl sulfonate, —B(OR$^8$)$_2$, —BF$_3$ or —Bi(R$^1$)$_2$, to provide said compound of Formula Ia-1.

The coupling stage of this process is optionally carried out at either i) elevated temperature and optionally in the presence of a base or ii) in the presence of a metal-based catalyst and a base.

In another particular embodiment of Method 1, there is provided a process for preparing a compound of Formula Ia-1

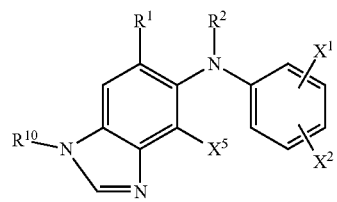

Ia-1 and salts and solvates thereof, wherein $R^1$, $R^2$, $R^{10}$, $X^1$, $X^2$ and $X^5$ are as defined herein, said method comprising:

coupling a compound of Formula VIIIa-1,

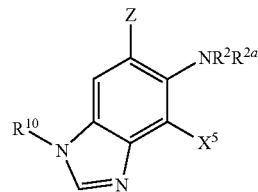

VIIIa-1 wherein $R^{2a}$ is hydrogen, with a reagent having the Formula X

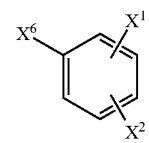

X wherein $X^1$ and $X^2$ are as defined herein and $X^6$ is F, Cl, Br, I, —OSO$_2$CF$_3$, alkyl sulfonate, aryl sulfonate, alkylaryl sulfonate, —B(O—R$^8$)$_2$, —BF$_3$ or —Bi(R$^1$)$_2$, in the presence of a suitable metal-based catalyst and a base in an appropriate solvent.

In one embodiment the reagent of Formula X has the Formula

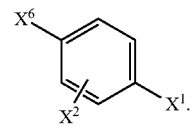

where $X^1$ is Br, $X^2$ is alkyl or halogen and $X^6$ is iodo.

In one embodiment the compound for Formula Ia-1 is isolated as its esterified form (i.e., wherein Z is COOR$^1$). In another embodiment the ester group COOR$^1$ is hydrolyzed and the compound is isolated as a free acid (wherein Z is COOH) or a salt thereof, for example a sodium salt.

In another embodiment, the present invention provides a method, referred to herein as Method 2, for preparing N-3 benzimidazole compounds represented by Formula Ia-2 and their synthetic intermediates

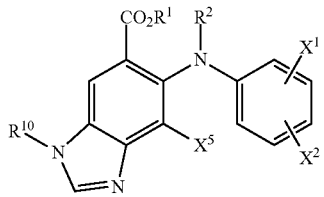

Ia-2 and salts and solvates thereof, wherein $R^1$, $R^2$, $R^{10}$, $X^1$, $X^2$ and $X^5$ are as defined herein, said method comprising:

nitrating a compound having the Formula

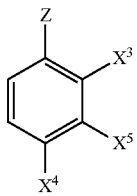

wherein $X^3$, $X^4$, $X^5$ and Z are as defined herein, to provide a compound of Formula II

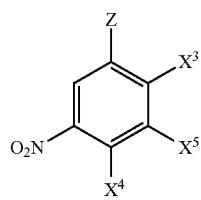

wherein Z, $X^3$, $X^4$ and $X^5$ are as defined herein;

treating said compound of Formula II optionally at an elevated temperature and/or pressure with two or more equivalents of (i) a reagent that contains or generates ammonia, (ii) a primary or secondary amine other than an aromatic amine or (iii) a reagent that delivers a group that can subsequently be converted into an amine to provide a compound of Formula VI-11 wherein $R^{2a}$ is as defined herein; or treating said compound of Formula II with (iv) two or more equivalents of a metal azide optionally at an elevated temperature and/or pressure to provide a compound of Formula VI-12

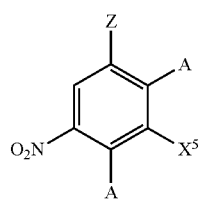

VI-11: A = $NR^2R^{2a}$
VI-12: A = $N_3$ wherein Z, $X^5$, $R^2$ and $R^{2a}$ are as defined herein;

reacting said compound of Formula VI-11 or VI-12 with a compound having the Formula $R^1OH$, wherein $R^1$ is as defined herein, optionally in the presence of an activating agent that activates the Z group towards reaction with said compound having the Formula $R^1OH$, to provide a compound of Formula Va-11 or Va-12

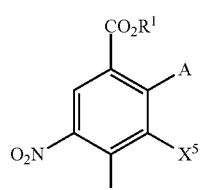

Va-11: A = $NR^2R^{2a}$
Va-12: A = $N_3$ wherein $R^1$, $R^2$, $R^{2a}$ and $X^5$ are as defined herein;

reducing said compound of Formula Va-11 or Va-12 to provide a compound of Formula VIIa-2

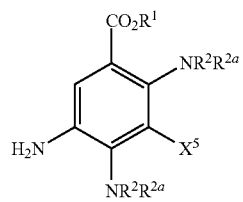

VIIa-2 wherein $R^1$, $R^2$, $R^{2a}$ and $X^5$ are as defined herein, and wherein when A of Formula Va-11 or Va-12 is —NH-benzyl, —$NHOR^1$, —$NHNHR^1$ or $N_3$, then $R^2$ and $R^{2a}$ of Formula VIIa-2 are hydrogen;

when $R^{2a}$ is hydrogen, cyclizing said compound of Formula VIIa-2 to provide a compound of Formula VIIIa-2

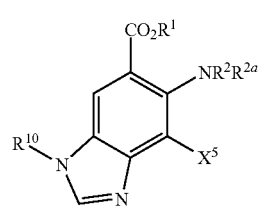

VIIIa-2 wherein $R^1$, $R^2$, $R^{2a}$, $R^{10}$ and $X^5$ are as defined herein; and when $R^{2a}$ is hydrogen, coupling said compound of Formula VIIIa-2 with a reagent having the Formula

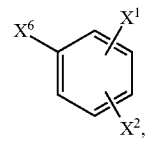

optionally either (i) at elevated temperature and optionally in the presence of a base, or (ii) in the presence of a metal-based catalyst and a base, wherein $X^1$, $X^2$ and $X^6$ are as defined herein, to provide said compound of Formula Ia-2.

Yet another embodiment of the present invention provides a method, referred to herein as Method 3, for preparing N–3 benzimidazole compounds represented by Formula Ib-1 and their synthetic intermediates

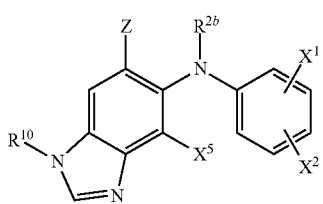

Ib-1 and salts and solvates thereof, wherein Z, $R^{2b}$, $R^{10}$, $X^1$, $X^2$ and $X^5$ are as defined herein, said method comprising:

nitrating a compound having the Formula

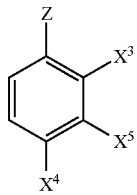

wherein $X^3$, $X^4$, $X^5$ and Z are as defined herein, to provide a compound of Formula II

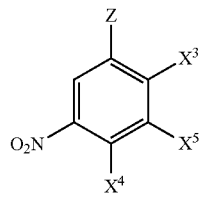

II wherein $X^3$, $X^4$, $X^5$ and Z are as defined herein;

reacting said compound of Formula II with (i) a reagent that contains or generates ammonia, (ii) a primary or secondary amine other than an aromatic amine or (iii) a reagent that delivers a group that can subsequently be converted into an amine under conditions that allow selective displacement of $X^4$ to provide a compound of Formula III-11; or reacting said compound of Formula II with (iv) a metal azide under conditions that allow selective displacement of $X^4$ to provide a compound of Formula III-12

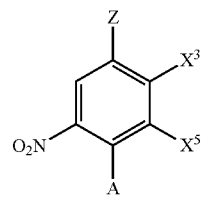

III-11: A = $NR^2R^{2a}$
III-12: A = $N_3$ wherein $X^3$, $X^5$, $R^2$, $R^{2a}$ and Z are as defined herein;

reacting said compound of Formula III-11 or III-12, optionally at elevated temperatures, with (i) a reagent that contains or generates ammonia, (ii) a primary or secondary amine other than an aromatic amine or (iii) a reagent that delivers a group that can subsequently be converted into an amine to provide a compound having Formula Vb-11 wherein B is $-NR^{2b}R^{2c}$ and A is $-NR^2R^{2a}$ or $N_3$; or reacting said compound of Formula III-11 or III-12 with (iv) a metal azide, optionally at elevated temperatures, to provide a compound of Formula Vb-12 wherein B is $N_3$ and A is $-NR^2R^{2a}$ or $N_3$,

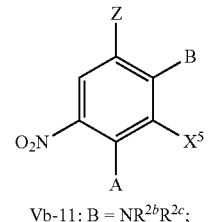

Vb-11: B = $NR^{2b}R^{2c}$;
A = $NR^2R^{2a}$ or $N_3$
Vb-12: B = $N_3$,
A = $NR^2R^{2a}$ or $N_3$ wherein Z, $X^5$, $R^2$, $R^{2a}$, and $R^{2b}$ are as defined herein and $R^{2c}$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, $-COR^6$, $-C(O)OR^6$, $-C(O)NR^6R^7$, $-OR^1$ or $-NHR^1$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl;

reducing said compound of Formula Vb-11 or Vb-12 to provide a compound of Formula VIIb-1

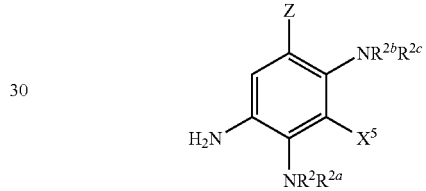

VIIb-1 wherein Z, $R^2$, $R^{2a}$, $R^{2b}$, $R^{2c}$ and $X^5$ are as defined herein, and wherein when A and/or B of Formula Vb-11 or Vb-12 is $-NH$-benzyl, $N_3$, $-NHOR^1$ or $-NHNHR^1$, then $R^2$ and $R^{2a}$ and/or $R^{2b}$ and $R^{2c}$, respectively, of Formula VIIb-1 are hydrogen;

when $R^{2a}$ is hydrogen, cyclizing said compound of Formula VIIb-1 to provide a compound of Formula VIIIb-1

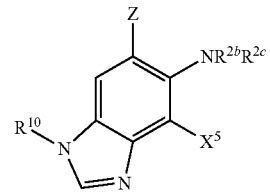

VIIIb-1 wherein Z, $R^{2b}$, $R^{2c}$, $R^{10}$ and $X^5$ are as defined herein; and when $R^2$ is hydrogen, coupling said compound of Formula VIIIb-1 with a reagent having the formula

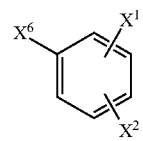

optionally either (i) at elevated temperature and optionally in the presence of a base, or (ii) in the presence of a metal-based catalyst and a base, wherein $X^1$, $X^2$ and $X^6$ are as defined herein, to provide said compound of Formula Ib-1.

In another embodiment, the present invention provides a process, referred to herein as Method 4, for preparing N–3 benzimidazole compounds represented by Formula Ib-2 and their synthetic intermediates

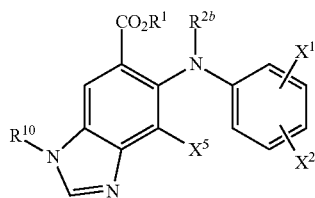

and salts and solvates thereof, wherein $R^1$, $R^{2b}$, $R^{10}$, $X^1$, $X^2$ and $X^5$ are as defined herein, said method comprising:
nitrating a compound having the formula

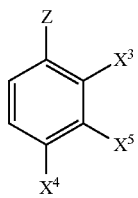

wherein $X^3$, $X^4$, $X^5$ and Z are as defined herein, to provide a compound of Formula II

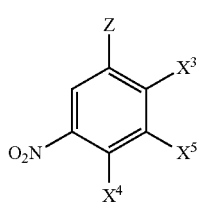

wherein $X^3$, $X^4$, $X^5$ and Z are as defined herein;
reacting said compound of Formula II with (i) a reagent that contains or generates ammonia, (ii) a primary or secondary amine other than an aromatic amine or (iii) a reagent that delivers a group that can subsequently be converted into an amine, under conditions that allow selective displacement of $X^4$, to provide a compound of Formula III-11, or reacting said compound of Formula II with (iv) a metal azide under conditions that allow selective displacement of $X^4$ to provide a compound of Formula III-12

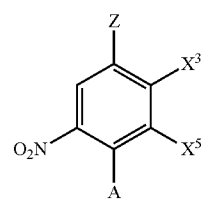

III-11: A = $NR^2R^{2a}$
III-12: A = $N_3$ wherein Z, $R^2$, $R^{2a}$, $X^3$ and $X^5$ are as defined herein;
reacting said compound of Formula III-11 or III-12 with a compound having the formula $R^1OH$ wherein $R^1$ is as defined herein, optionally in the presence of an activating agent that activates the Z group towards reaction with said compound of formula $R^1OH$, to provide a compound of Formula IV-21 or IV-22

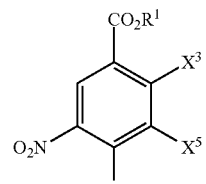

IV-21: A = $NR^2R^{2a}$
IV-22: A = $N_3$ wherein $R^1$, $R^2$, $R^{2a}$, $X^3$ and $X^5$ are as defined herein;
reacting said compound of Formula IV-21 or IV-22, optionally at elevated temperatures, with (i) a reagent that contains or generates ammonia, (ii) a primary or secondary amine other than an aromatic amine or (iii) a reagent that delivers a group that can subsequently be converted into an amine to provide a compound of Formula Vb-21 wherein B is —$NR^{2b}R^{2c}$ and A is —$NR^2R^{2a}$ or $N_3$, or reacting said compound of Formula IV-21 or IV-22 with (iv) a metal azide, optionally at elevated temperatures, to provide a compound of Formula Vb-22 wherein B is $N_3$ and A is —$NR^2R^{2a}$ or $N_3$,

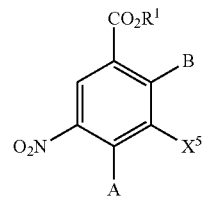

Vb-21: B = $NR^{2b}R^{2c}$
Vb-22: B = $N_3$ wherein $R^1$, $R^2$, $R^{2a}$, $R^{2b}$, $R^{2c}$ and $X^5$ are as defined herein;
reducing said compound of Formula Vb-21 or Vb-22 to provide a compound of Formula VIIb-2

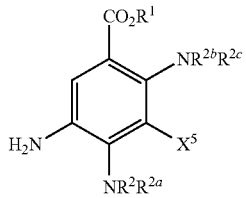

wherein $R^1$, $R^2$, $R^{2a}$, $R^{2b}$, $R^{2c}$ and $X^5$ are as defined herein, and wherein when A and/or B of Formula Vb-21 or Vb-22 is —NH-benzyl, $N_3$, —$NHOR^1$ or —$NHNHR^1$, then $R^2$ and $R^{2a}$ and/or $R^{2b}$ and $R^{2c}$, respectively, of Formula VIIb-2 are hydrogen;
when $R^{2a}$ is hydrogen, cyclizing said compound of Formula VIIb-2 to provide a compound of Formula VIIIb-2

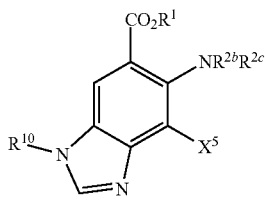

VIIIb-2 wherein $R^1$, $R^{2b}$, $R^{2c}$, $R^{10}$ and $X^5$ are as defined herein; and when $R^{2c}$ is hydrogen, coupling said compound of Formula VIIIb-2 with a compound having the formula

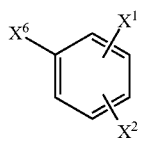

optionally either (i) at elevated temperature and optionally in the presence of a base, or (ii) in the presence of a metal-based catalyst and a base, wherein $X^1$, $X^2$ and $X^6$ are as defined herein, to provide said compound of Formula Ib-2.

Yet another embodiment of the present invention provides a method, referred to herein as Method 5, for preparing N–1 benzimidazole compounds represented by Formula Ic-1 and their synthetic intermediates

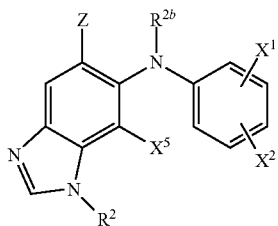

Ic-1 and salts and solvates thereof, wherein Z, $R^{2b}$, $X^1$, $X^2$ and $X^5$ are as defined herein, said method comprising:

cyclizing a compound of Formula VIIb-1

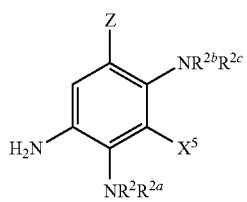

VIIb-1 prepared as described in Method 3, wherein $R^2$ is not hydrogen and Z, $R^{2a}$, $R^{2b}$, $R^{2c}$ and $X^5$ are as defined herein to provide a compound of Formula XIb-1

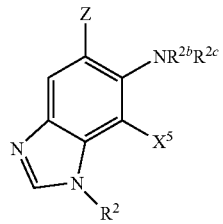

VIb-1 wherein Z, $R^{2b}$, $R^{2c}$, $R^{10}$ and $X^5$ are as defined herein and $R^2$ is not hydrogen; and coupling said compound of Formula XIb-1 with a reagent having the formula

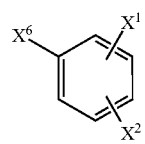

optionally either (i) at elevated temperatures and optionally in the presence of a base, or (ii) in the presence of a metal-based catalyst and a base, wherein $X^1$, $X^2$ and $X^6$ are as defined herein, to provide said compound of Formula Ic-1.

The step of cyclizing a compound of Formula VIIa-1, VIIa-2, VIIb-1 or VIIb-2 to provide benzimidazole core structures in any of the above-described Methods 1-5 can be performed in several ways. Several cyclization methods, namely Methods A-E, are described in general below with respect to the cyclization of a compound of Formula VIIb-1 for ease of explanation; however, it is to be understood that Methods A-E apply equally to the cyclization of compounds of Formulas VIIa-1, VIIa-2 and VIIb-2. The cyclization methods will provide either N–3 benzimidazole derivatives or N–1 benzimidazole derivatives, depending on the reagents used and the substituents on the compounds of Formulas VIIa-1, VIIa-2, VIIb-1 and VIIb-2.

Method A:

According to Method A, a compound of Formula VIIb-1, wherein $R^2$ and $R^{2a}$ are hydrogen, can be cyclized to the corresponding benzimidazole represented by Formula VIIIb-1, wherein $R^{10}$ is hydrogen, by a "one pot" method upon treatment with (i) formic acid, optionally in the presence of an additional acid or (ii) a formic acid derivative in the presence of an acid. The compound of Formula VIIIb-1 can then be carried on to a compound of Formula Ib as described in detail below.

Method B:

According to Method B, a compound of Formula VIIb-1, wherein $R^{2a}$ is hydrogen and $R^2$ is not hydrogen, can be cyclized to the corresponding N–3 benzimidazole represented by Formula VIIIb-1 by a multi-step method upon treatment with (i) formic acid, optionally in the presence of an additional acid, (ii) a formic acid derivative in the presence of an acid, or (iii) formaldehyde or a formaldehyde derivative in the presence of an acid, to provide an intermediate N–1 benzimidazole compound represented by the Formula XIb-1. The compound of Formula XIb-1 can then be carried on to the N–3 benzimidazole derivative Formula Ib-1 by alkylating the N–3 position, followed by removal of the $R^2$ group at the N–1 position.

Method C:

According to Method C, a compound of Formula VIIb-1, wherein $R^2$ and $R^{2a}$ are hydrogen, can be cyclized to the corresponding N-3 benzimidazole represented by Formula VIIIb-1 wherein $R^{10}$ is methyl, by a "one pot" method upon treatment with two or more equivalents of formaldehyde or a formaldehyde derivative in the presence of an acid. The compound of Formula VIIIb-1 can then be carried on to the N-3 benzimidazole compound represented by Formula Ib-1 as described in detail below.

Method D:

According to Method D, a compound of Formula VIIb-1, wherein $R^2$ and $R^{2a}$ are hydrogen, can be cyclized to the corresponding benzimidazole represented by Formula VIIIb-1, wherein $R^{10}$ is not hydrogen, by a step-wise process comprising:

(a) reacting a compound of Formula VIIb-1

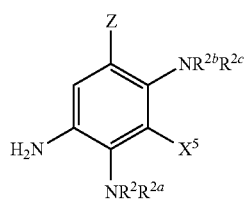

VIIb-1 with a suitable acylating agent to provide a compound of Formula IXb

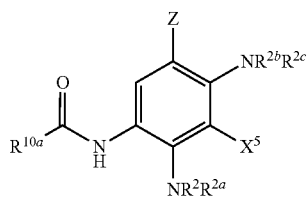

IXb wherein Z, $R^2$, $R^{2a}$ and $X^5$ are as defined herein and $R^{10a}$ is H, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl, and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$;

(b) reducing the amide group of said compound of Formula IXb to provide a compound of Formula Xb

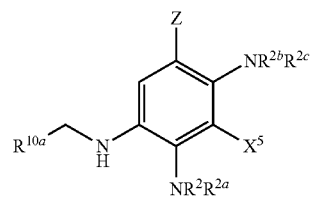

Xb wherein Z, $R^2$, $R^{2a}$, $R^{10a}$ and $X^5$ are as defined herein; and (c) reacting said compound of Formula Xb with (i) formic acid optionally in the presence of an additional acid or (ii) a formic acid derivative in the presence of an acid to provide said compound of Formula VIIIb-1. Alternatively, according to another embodiment of Method D, compound of Formula Xb may be obtained by reaction of said compound of Formula VIIb-1 with an alkylating agent of formula $R^{10a}CH_2L$, wherein L is a leaving group, such as Cl, Br, I, OMs, OTs, OTf, etc.

Method E:

According to Method E, a compound of Formula VIIb-1, wherein $R^{2a}$ is hydrogen and $R^2$ is not hydrogen, can be cyclized to the corresponding benzimidazole compound of Formula VIIIb-1, wherein $R^{10}$ is not hydrogen, by a step-wise method comprising:

(a) reacting a compound of Formula VIIb-1

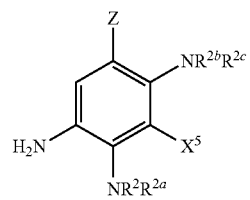

XIIb-1 with a suitable acylating agent to provide a compound of Formula IXb

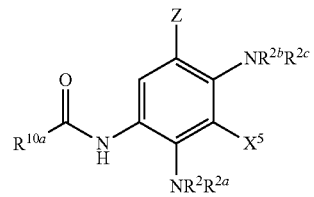

IXb wherein Z, $R^2$, $R^{2a}$ and $X^5$ are as defined herein and $R^{10a}$ is H, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl, and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$;

(b) reducing the amide group of said compound of Formula IXb to provide a compound of Formula Xb

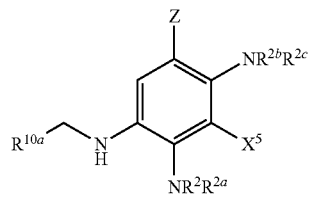

Xb wherein Z, $R^2$, $R^{2a}$, $R^{2b}$, $R^{2c}$, $R^{10a}$ and $X^5$ are as defined herein;

(c) reacting said compound of Formula Xb with (i) formic acid optionally in the presence of an additional acid or (ii) a formic acid derivative in the presence of an acid to provide said compound of Formula XIIb-1

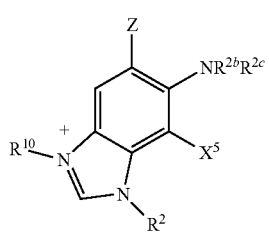

VIIb-1 wherein Z, $R^2$, $R^{2b}$, $R^{2c}$, $R^{10a}$ and $X^5$ are as defined herein; and removing the $R^2$ group to provide the N-3 benzimidazole compound of Formula Ib-1. Alternatively, according to another embodiment of Method E, a compound of Formula Xb may be obtained by reaction of a compound of Formula VIIb-1 with an alkylating agent of formula $R^{10a}CH_2L$, wherein L is a leaving group, such as Cl, Br, I, OMs, OTs, OTf, etc.

In a further aspect, the present invention provides compounds of Formulas III, Va-1, Vb-1, VIIa-1, VIIb-1, VIIIa-1, VIIIb-1 and XIb-1 and salts and solvates thereof. Compounds having Formulas III, Va-1, Vb-1, VIIa-1, VIIb-1, VIIIa-1, VIIIb-1 and XIb-1 are useful for the synthesis of heterocyclic compounds including, but not limited to, benzimidazoles, benzimidazolones, pyrazines, and piperazines.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the detailed description and in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
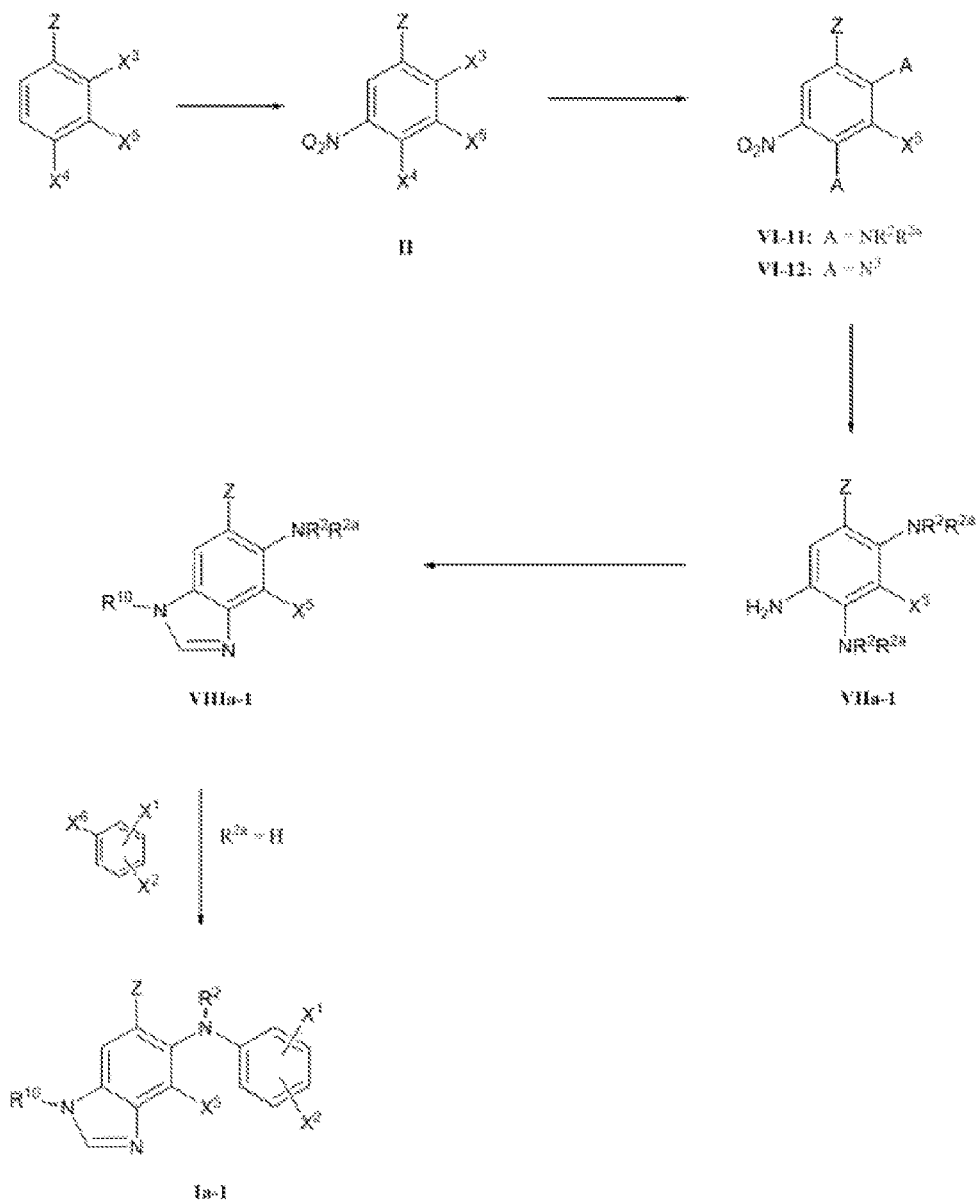
FIG. 1 shows a reaction scheme (Method 1) for the synthesis of compounds having the Formula Ia-1.

One aspect of the present invention provides methods for the preparation of compounds of the general Formulas Ia-1, Ia-2, Ib-1, Ib-2 and Ic-1 and their synthetic intermediates

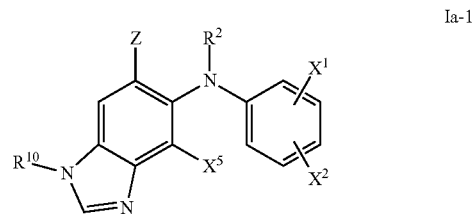

Ia-1

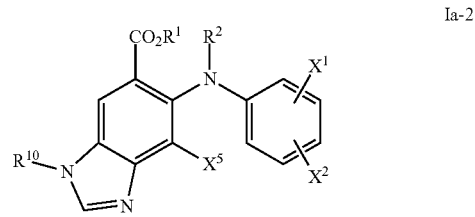

Ia-2

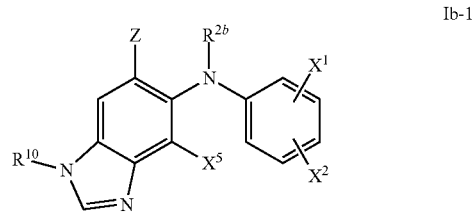

Ib-1

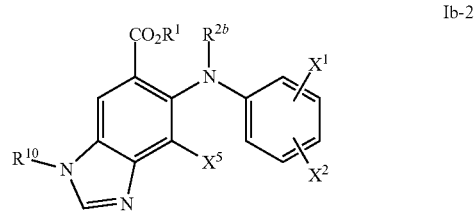

Ib-2

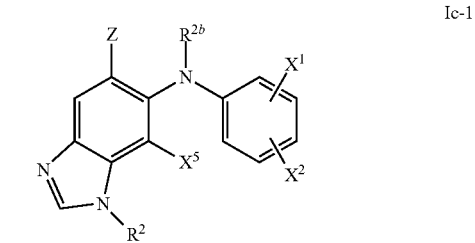

Ic-1 and salts and solvates thereof, wherein:

Z is —C(=O)OR$^1$, —C(=O)NR$^6$R$^7$, CN, —C(=O)H, or

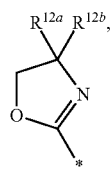

or a moiety that may be transformed into any of said Z groups, for example through hydrolysis;

R$^1$ is hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, C$_1$-C$_4$ alkyl, C$_2$-C$_4$ alkenyl, C$_2$-C$_4$ alkynyl, C$_3$-C$_6$ cycloalkyl and C$_3$-C$_6$ heterocycloalkyl;

R$^2$ is hydrogen, C$_1$-C$_{10}$ alkyl, C$_2$-C$_{10}$ alkenyl, C$_2$-C$_{10}$ alkynyl, arylalkyl, trialkylsilyl, dialkylarylsilyl, —COR$^6$, —C(O)OR$^6$ or —C(O)NR$^6$R$^7$, wherein said alkyl, alkenyl, alkynyl and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl, wherein for Formula Ic-1, R$^2$ is not hydrogen;

R$^{2b}$ is hydrogen, C$_1$-C$_{10}$ alkyl, C$_2$-C$_{10}$ alkenyl, C$_2$-C$_{10}$ alkynyl, arylalkyl, trialkylsilyl, dialkylarylsilyl, —COR$^6$, —C(O)OR$^6$ or —C(O)NR$^6$R$^7$, wherein said alkyl, alkenyl, alkynyl and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl;

X$^1$ and X$^2$ are independently selected from hydrogen, F, Cl, Br, I, OR$^8$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl or C$_1$-C$_{10}$ thioalkyl, wherein said alkyl, alkenyl, alkynyl, cycloalkyl, cycloalkylalkyl and thioalkyl portions are optionally substituted with one or more groups independently selected from oxo, halogen, cyano, nitro, trifluoromethyl, difluoromethoxy, trifluoromethoxy and azido;

X$^5$ is H, F, Cl, Br, I or C$_1$-C$_6$ alkyl;

R$^6$ and R$^7$ are independently hydrogen, trifluoromethyl, —OR$^8$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, or R$^6$ and R$^7$ together with the atom to which they are attached form a 4 to 10 membered heteroaryl or heterocyclic ring, wherein said heteroaryl and heterocyclic rings are optionally substituted with one or more groups independently selected from halogen, trifluoromethyl, difluoromethoxy, trifluoromethoxy and OR$^8$;

R$^8$ is hydrogen, C$_1$-C$_{10}$ alkyl, C$_2$-C$_{10}$ alkenyl, aryl or arylalkyl, wherein said alkyl, alkenyl, aryl and arylalkyl are optionally substituted with one or more groups independently selected from OH, —O—(C$_1$-C$_{10}$-alkyl) and —O—(C$_1$-C$_{10}$-alkenyl);

R$^{10}$ is hydrogen, C$_1$-C$_{10}$ alkyl, C$_3$-C$_{10}$ cycloalkylalkyl, arylalkyl, heteroarylalkyl or heterocyclylalkyl, wherein said alkyl, cycloalkylalkyl, arylalkyl, heteroarylalkyl and heterocyclylalkyl portions are optionally substituted with one or more groups independently selected from halogen, hydroxyl, cyano, nitro, azido, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, —NR$^6$R$^7$ and —OR$^8$; and R$^{12a}$ and R$^{12b}$ are independently selected from hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl and heteroarylalkyl, or R$^{12a}$ and R$^{12b}$ together with the atom to which they are attached form a 4 to 10 membered carbocyclic, heteroaryl or heterocyclic ring.

Methods for preparing N–3 benzimidazole compounds of the general Formulas Ia-1, Ia-2, Ib-1 and Ib-2 can be performed in several ways. Four methods, namely Methods 1-4, are shown in FIGS. 1-4, respectively, and are described below. Method 5 describes the synthesis of the N–1 benzimidazole derivatives represented by Formula Ic-1.

In certain embodiments of Methods 1-5, Z is —C(=O)NR$^6$R$^7$. In certain embodiments, R$^6$ is OR$^8$ and R$^7$ is H. In certain embodiments, R$^8$ is C$_1$-C$_{10}$ alkyl optionally substituted with OH, O—(C$_1$-C$_6$-alkyl) or —O—(C$_1$-C$_{10}$-alkenyl). In certain embodiments, R$^8$ is —(CH$_2$)$_2$—OH. In particular embodiments, Z is —C(=O)NH(CH$_2$)$_2$—OH.

In certain embodiments of Methods 1-5, Z is COOR$^1$. In certain embodiments, R$^1$ is C$_1$-C$_{10}$ alkyl. In particular embodiments, R$^1$ is methyl.

In certain embodiments of Methods 1-5, X$^5$ is halogen. In particular embodiments, X$^5$ is F.

In certain embodiments of Methods 1-5, X$^1$ and X$^2$ are H or halogen, and X$^6$ is halogen. In other embodiments, X$^2$ is alkyl. In certain embodiments, X$^1$ is Br. In certain embodiments, X$^2$ is Cl. In certain embodiments, X$^6$ is iodo.

In certain embodiments of Methods 1-5, R$^{10}$ is C$_1$-C$_{10}$ alkyl. In particular embodiments, R$^{10}$ is methyl.

In other embodiments of Methods 1-5, R$^2$ and R$^{2b}$ are hydrogen.

In certain embodiments, Methods 1-5 provide methods of preparing compounds of Ia-1, Ia-2, Ib-1, Ib-2 and Ic-1 wherein Z is —C(=O)NR$^6$R$^7$, X$^5$ is halogen, X$^1$ and X$^2$ are H or halogen, and R$^{10}$ is C$_1$-C$_{10}$ alkyl. In certain embodiments, R$^6$ is OR$^8$, R$^7$ is H, X$^5$ is F, X$^2$ is Cl, and R$^{10}$ is methyl. In particular embodiments, Z is —C(=O)NH—(CH$_2$CH$_2$OH), X$^5$ is F, X$^2$ is Cl, and R$^{10}$ is methyl.

In certain embodiments, Methods 1-5 provide methods of preparing compounds of Ia-1, Ia-2, Ib-1, Ib-2 and Ic-1 wherein Z is COOR$^1$, X$^5$ is halogen, X$^1$ and X$^2$ are H or halogen, and R$^{10}$ is C$_1$-C$_{10}$ alkyl. In certain embodiments, R$^1$ is C$_1$-C$_{10}$ alkyl, X$^5$ is F, X$^2$ is Cl, and R$^{10}$ is methyl. In particular embodiments, Z is COOCH$_2$, X$^5$ is F, X$^2$ is Cl, and R$^{10}$ is methyl.

Method 1:

One embodiment of the present invention provides a method, referred to herein as Method 1 and shown schematically in FIG. 1, for preparing compounds of Formula Ia-1 and their synthetic intermediates

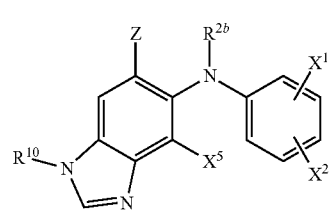

Ia-1 and salts and solvates thereof, wherein $X^1$, $X^2$, $X^3$, $R^2$ and $R^{10}$ are as defined herein, and Z is —C(═O)OR$^1$, —C(═O)NR$^6$R$^7$, CN, —C(═O)H, or

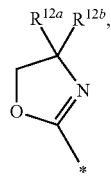

or a moiety that can be transformed into any one of said Z groups, for example through hydrolysis. Examples of moieties that can be transformed into the defined Z groups through hydrolysis include, but are not limited to, orthoesters having the formula C(OR$^1$)$_3$ and acetals having the formula CH(OR$^1$)$_2$.

More specifically, Method 1 comprises nitrating a compound having the Formula

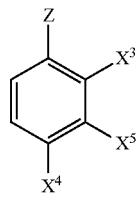

wherein $X^3$ and $X^4$ are independently F, Cl, Br, I, or a sulfonate ester such as, but not limited to, trifluoromethanesulfonate, methanesulfonate, benzenesulfonate or p-toluenesulfonate, and $X^5$ and Z are as defined herein, to provide a compound of Formula II

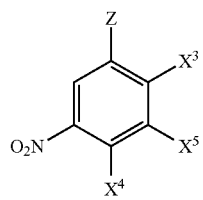

II wherein $X^3$, $X^4$ and $X^5$ are as defined herein. In one embodiment of a compound of Formula II, $X^3$, $X^4$ and are F.

Nitration reaction conditions, which are well known to those skilled in the art, can include reacting an aromatic system with nitric acid in the presence of an activating agent such as concentrated sulfuric acid. For example, in one embodiment a 2,3,4-trihalobenzoic can be treated with fuming nitric acid in H$_2$SO$_4$ to provide a 2,3,4-trihalo-5-nitrobenzoic acid, such as 2,3,4-trifluoro-5-nitrobenzoic acid, in high yield.

The compound of Formula II then undergoes a bis-amination reaction comprising a nucleophilic displacement of $X^3$ and $X^4$. Nucleophilic substitution of a leaving group (such as a halide, or sulfonate ester) ortho- or para- to a nitro group in an aromatic ring is a method well known in the art for the introduction of an amino group into an aromatic ring. In the case of compounds of Formula II, leaving groups at positions ortho- and para- to the nitro group can be replaced in a single process under suitable conditions. Examples of bis-aminations are illustrated herein for Method 1 as well as Method 2 below. More specifically, according to Method 1a compound of Formula II is treated optionally at elevated temperatures with two or more equivalents of (i) a reagent that contains or generates ammonia, (ii) a primary or secondary amine other than an aromatic amine or (iii) a reagent that delivers a group that can subsequently be converted into an amine to provide a compound of Formula VI-11 wherein A is NR$^2$R$^{2a}$, or said compound of Formula II is treated with (iv) two or more equivalents of a metal azide optionally at elevated temperatures and/or pressure to provide a compound of Formula VI-12 wherein A is N$_3$

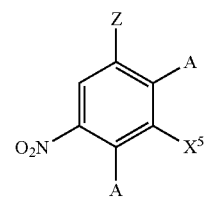

VI-11: A = NR$^2$R$^{2a}$
VI-12: A = N$_3$ wherein $X^5$, $R^2$ and Z are as defined herein, and $R^{2a}$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —COR$^6$, —C(O)OR$^6$, —C(O)NR$^6$R$^7$, —OR$^1$, or —NHR$^1$, wherein said alkyl, alkenyl, alkynyl, benzyl, allyl, or arylalkyl portions are optionally substituted with one or more groups independently selected from halogen, hydroxyl, $C_1$-$C_4$ alkyl, $C_2$-$C_4$ alkenyl and $C_2$-$C_4$ alkynyl. In certain embodiments, $R^{2a}$ is a nitrogen protecting group such as hydrogen, substituted or unsubstituted benzyl, allyl or —C(O)OR$^6$. In a particular embodiment, $R^{2a}$ is hydrogen.

In a particular embodiment of Method 1, the compound of Formula II, where Z is COOH, can undergo an esterification of the Z group and a bis-amination in one step. This may be achieved by reacting the compound of Formula II, where Z is COOH, with a compound of formula R$^1$OH wherein R$^1$ is $C_1$-$C_{10}$ alkyl, optionally in the presence of an activating agent, to form the corresponding ester in-situ, followed by reaction of the ester with two or more equivalents of (i) a reagent that generates ammonia, for example ammonium hydroxide or (ii) a primary or secondary amine other than an aromatic amine to provide a compound of Formula VI-11, wherein Z is COOR$^1$, R$^1$ is $C_1$-$C_{10}$ alkyl, and $R^2$ and $R^{2a}$ are as defined herein.

Examples of activating agents include, but are not limited to, (a) mineral and organic acids; (b) reagents capable of converting a carboxylic acid into an acid chloride including, but not limited to, halogenating agents such as SOCl$_2$ or (COCl)$_2$, alkyl chloroformates, aryl chloroformates and acid chlorides (such as trimethylacetyl chloride); (c) carbodiimides, including, but not limited to, dicyclohexylcarbodiimide (DCC); (d) trialkylsilyl halides including, but not limited to, trimethylsilyl chloride (Me$_3$SiCl); (e) chloroformates such as alkyl chloroformates (e.g., isobutyl chloroformate) and aryl chloroformates (phenyl chloroformate), and (f) dialkylazodicarboxylates such as, but not limited to, diethylazodicarboxylate (DEAD), which is typically used in conjunction with a phosphine reagent such as, but not limited to, Ph$_3$P. In one embodiment, the activating agent is trimethylsilyl chloride.

Examples of reagents that contain or generate ammonia include, but are not limited to, $NH_3$ and $NH_4OH$. Examples of primary and secondary amines suitable for purposes of this invention include amines having the formula $HNR^2R^{2a}$, wherein $R^2$ and $R^{2a}$ are as defined herein. Specific examples of primary and secondary amines include, but are not limited to methylamine, benzylamine, dibenzylamine, allylamine, diallylamine and hexamethyldisilazane. Examples of reagents that deliver a group that can subsequently be converted into an amine include, but are not limited to, (1) metal amides such as sodium, potassium and lithium amide, or alkylated derivatives thereof, (2) protected ammonia or amide equivalents such as, but not limited to, hydroxylamines and hydrazines, (3) nitrogen nucleophiles having the Formula $MNR^2R^{2a}$ wherein M is a metal such as Na, K, Li, Cs, Mg or Al, and (4) metal silylamides such as lithium (bis)(trimethylsilyl)amide, sodium (bis)(trimethylsilyl)amide or potassium (bis)(trimethylsilyl)amide. Examples of metal azides include, but are not limited to, sodium azide ($NaN_3$), potassium azide ($KN_3$) and lithium azide ($LiN_3$).

The bis-amination reaction can be performed in any suitable organic or aqueous solvent, including but not limited to N-methylpyrrolidine, THF, dioxane, at temperatures ranging from −20° C. to 200° C. In certain embodiments the reaction is performed at elevated temperatures in the range of about 50 and 100° C. One example of a method for preparing a compound of Formula VI-11 comprises reacting a compound of Formula II with ammonium hydroxide at a temperature between 50 and 100° C., in particular between 80 and 90° C.

Another example of a method for preparing a compound of Formula VI-11 from a compound of Formula II comprises reacting, for example, a compound of Formula II, wherein $Z=CO_2H$, and $X^3$ and $X^4=F$, with excess ammonium hydroxide solution in N-methylpyrrolidine at an elevated temperature, for example between 80-90° C., in a sealed reactor, under a slight pressure of ammonia, for example 0-5 bar, to provide compound Formula VI-11 wherein $Z=CO_2H$, $R^2=H$, and $R^{2a}=H$ in high yield.

This invention also provides compounds of Formulas VI-11 and VI-12 and salts and solvates thereof, wherein Z, $X^5$, A, $R^2$ and $R^{2a}$ are as defined herein. In some embodiments of compounds of Formula VI-11 and VI-12, Z is —$COOR^1$ or —$C(=O)NR^6R^7$. In certain embodiments, $R^6$ is —$OR^8$ and $R^7$ is H. In particular embodiments, $R^8$ is —$(CH_2)_2$—OH. In some embodiments, $X^5$ is halogen. In particular embodiments, $X^5$ is F. In some embodiments of compounds of Formula VI-11, A is $NH_2$.

The compound of Formula VI-11 or VI-12 is then reduced to provide compound of Formula VIIa-1

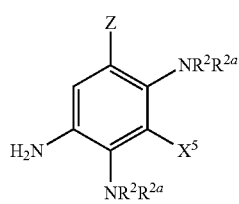

VIIa-1 wherein $X^5$, $R^2$, $R^{2a}$ and Z are as defined herein, wherein when A of said compound of Formula VI-11 or Formula VI-12 is —NH-benzyl, —$NHOR^1$, —$NHNHR^1$, or $N_3$, then $R^2$ and $R^{2a}$ of the compound of Formula VIIa-1 are hydrogen.

The reduction step can be performed utilizing reaction conditions and reagents well known to those skilled in the art. Examples of suitable methods for reducing an aromatic nitro group include, but are not limited to, dissolving metal reductions, catalytic hydrogenations, and enzymatic reactions. More specific examples of dissolving metal reductions include the use of a metal in a suitable solvent under acidic conditions. Examples of metals suitable for dissolving metal reductions include, but are not limited to, Zn, Fe and Sn. Suitable solvent systems include water and/or organic solvents such as, but not limited to, alcohols, carboxylic acids, ethers or a mixture of these. For example, in one embodiment a compound of Formula VI-11 or VI-12 can be converted to a compound of Formula VIIa-1 using zinc powder and concentrated HCl in a mixture of methanol and water, at temperatures between 0-100° C., more typically at 50-70° C. Catalytic hydrogenations can be performed with hydrogen in the presence of a metal catalyst in a suitable solvent system under hydrogen (for example, 1-20 atm. $H_2$) typically at temperatures between 0-100° C. Suitable metal catalysts for use in catalytic hydrogenations include, but are not limited to, Pd, Pt, Rh and Ni. Examples of suitable solvent systems include, but are not limited to, alcohols (e.g., methanol, ethanol, isopropanol), acetic acid, esters (e.g., ethyl acetate) and ethers (e.g., THF). Mixed solvents, including aqueous mixtures are also commonly used for hydrogenations. Catalytic hydrogenation was found to be particularly effective for the conversion of a compound of Formula VI-11 or VI-12 into a compound of Formula VIIa-1. In one embodiment, platinum oxide was found to be an effective and convenient catalyst, providing a compound of VIIa-1 free from carbon residue. In another embodiment, $Pd(OH)_2$ was a suitable hydrogenation catalyst. In a particular embodiment palladium supported on carbon was found to be effective. The reaction can be carried out in a range of organic solvents, and a mixture of methanol and THF was found to be both effective and convenient. Hydrogen pressure in a range between 2-10 bar was effective and the temperature was typically between 20-80° C.

This invention further provides compounds of Formula VIIa-1 and salts and solvates thereof wherein Z, $X^5$, $R^2$ and $R^{2a}$ are as defined herein. In some embodiments of compounds of Formula VIIa-1, Z is —$COOR^1$ or —$C(=O)NR^6R^7$. In certain embodiments, $R^6$ is $OR^8$ and $R^7$ is H. In particular embodiments, $R^8$ is —$(CH_2)_2$—OH. In some embodiments, $X^5$ is halogen. In particular embodiments, $X^5$ is F. In other embodiments, $R^2$ and $R^{2a}$ are hydrogen.

With continued reference to FIG. 1, the compound of Formula VIIa-1 can be cyclized to the benzimidazole derivative represented by Formula VIIIa-1 when $R^{2a}$ of said compound of Formula VIIa-1 is hydrogen.

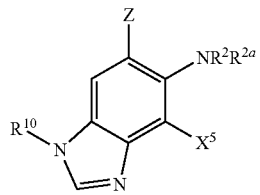

VIIIa-1

The cyclization step to provide the benzimidazole core structure can be performed in several ways, such as any one of Methods A-E as described herein.

Also provided herein are compounds of Formula VIIIa-1 and salts and solvates thereof wherein Z, $X^5$, $R^2$, $R^{2a}$ and $R^{10}$ are as defined herein. In some embodiments of compounds of Formula VIIIa-1, Z is $COOR^1$ or —$C(=O)NR^6R^7$. In certain embodiments, $R^6$ is $OR^8$ and $R^7$ is H. In particular embodiments, $R^8$ is —($CH_2$)$_2$—OH. In some embodiments of compounds of Formula VIIIa-1, $R^1$ is $C_1$-$C_{10}$ alkyl. In particular embodiments, $R^1$ is methyl. In some embodiments of compounds of Formula VIIIa-1, $X^5$ is halogen. In particular embodiments, $X^5$ is F. In some embodiments of compounds of Formula VIIIa-1, $R^2$ and $R^{2a}$ are hydrogen. In other embodiments, $R^{10}$ is methyl.

When $R^{2a}$ is hydrogen, the compound of Formula VIIIa-1 can be directly converted to compound of Formula Ia-1 as shown in FIG. 1. Several methods are known in the literature for the preparation of diarylamines by coupling an aromatic amine with a halobenzene (see, for Example, PCT Publication No. WO 02/083622). Nucleophilic aromatic substitutions and transition metal catalyzed processes are particularly common coupling methods. However, there are very few examples of efficient transition metal catalyzed coupling processes that provide diarylamines that are highly substituted in both rings, as is the case for compounds of Formula Ia-1. In addition, very few of the catalysts that have been reported in the literature for a coupling reaction between a trihalobenzene and an aromatic amine to provide the desired product in high yield. However, particular catalyst systems have been identified herein that can be employed to give high yields for the coupling of compounds of Formula VIIIa-1 with aryl halides.

More specifically, one embodiment for the preparation of compounds of Formula Ia-1, as shown in FIG. 1, comprises a coupling reaction between a compound of Formula VIIIa-1, wherein $R^{2a}$ is hydrogen, and an aryl halide in the presence of a suitable metal-based catalyst and a base in an appropriate solvent. In one embodiment, the aryl halide has the Formula

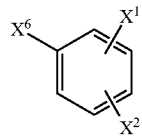

wherein $X^1$ and $X^2$ are as defined herein and $X^6$ is F, Cl, Br, I, —$OSO_2CF_3$, alkyl sulfonate, aryl sulfonate, alkylaryl sulfonate, —B(O—$R^8$)$_2$, —$BF_3$ or —Bi($R^1$)$_2$. In another embodiment, the aryl halide has the Formula

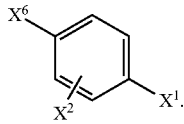

In certain embodiments, $X^1$ is F, Cl, Br, or I, $X^2$ is $C_1$-$C_{10}$ alkyl, F, Cl, Br, or I, and $X^6$ is F, Cl, Br, or I. In certain embodiments, $X^1$ is Br. In certain embodiments, $X_2$ is Cl. In another embodiment, $X^6$ is iodo. In a particular embodiment, 4-bromo-2-chloroiodobenzene was found to be an effective and regioselective partner for the coupling reaction in the conversion of compounds of Formula VIIIa-1 to compounds of Formula Ia-1, wherein the iodo group of 4-bromo-2-chloroiodobenzene is selectively displaced. Suitable bases for use in the coupling reactions of this invention include, but are not limited to, Group I and Group II metal bases such as $Na_2CO_3$, $K_2CO_3$, $Cs_2CO_3$, NaOH and NaOtBu, and organic bases such as triethylamine. Suitable solvents for the coupling reaction include, but are not limited to, toluene, anisole, 2-methyltetrahydrofuran and dioxane.

Suitable metal-based catalysts for this coupling reaction include, but are not limited to, organometallic catalysts. The phrase "organometallic catalyst" means a catalyst comprising a metal and an organic ligand. Examples of metals include, but are not limited to, palladium, copper, nickel, and platinum. The preferred ligands for copper include those containing heteroatoms such as oxygen, sulfur, nitrogen or phosphorous. Ligands containing oxygen groups are generally inexpensive and readily available, and ethylene glycol is a particular example of a convenient ligand that is effective in the process. For palladium catalyzed coupling reactions, phosphine ligands have been shown to be effective, and in certain cases bidentate ligands containing either two phosphine groups or one phosphine group and a second heteroatom-containing group have been shown to be effective. Examples of such ligands include, but are not limited to, DPE-phos and Xantphos. Illustrative examples of suitable organopalladium catalysts include, but are not limited to, Pd(OAc)$_2$ and Xantphos, Pd(OAc)$_2$ and DPE-phos, Pd$_2$(dba)$_3$ and Xantphos, Pd$_2$(dba)$_3$ and DPE-phos, palladium tetrakis(triphenylphosphine), and palladium dichloride [bis(diphenylphosphino)ferrocene]. Other organopalladium catalysts are known, and may be found in Comprehensive Organic Transformations, $2^{nd}$ ed., by Richard C. Larock, VCH Publishers, Inc., New York, 1999. Preferred catalysts include, but are not limited to, Pd(OAc)$_2$ and Pd$_2$(dba)$_3$ in combination with Xantphos or DPE-phos. A particular embodiment of the present invention comprises refluxing a compound of Formula VIIIa-1, wherein $R^{2a}$ is hydrogen, and a halo-substituted benzene in toluene in the presence of a catalytic amount of Pd(OAc)$_2$, Xantphos, and an excess amount of a suitable base such as $Cs_2CO_3$. Another embodiment of the present invention comprises refluxing a compound of Formula VIIIa-1, wherein $R^{2a}$ is hydrogen, and a halo-substituted benzene in toluene in the presence of a catalytic amount of Pd(OAc)$_2$ and DPE-phos in the presence of a suitable base. A particular embodiment of the present invention comprises heating a compound of Formula VIIIa-1 and a substituted halobenzene (e.g. 2-chloro-4-iodobromobenzne) at a temperature between 40-140° C. in anisole in the presence of a catalytic amount of Pd$_2$(dba)$_3$ and Xantphos and an excess amount of a suitable base such as $Cs_2CO_3$.

Figure 5:
FIG. 5 shows the structures of organometallic ligands used in certain aryl halide coupling reactions of the present invention.
Figure 5:
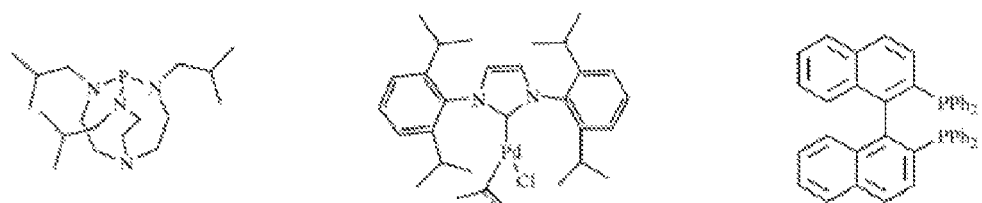
Figure 5:
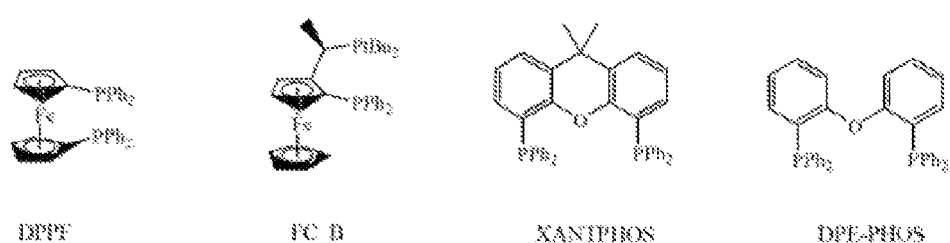
Figure 5:
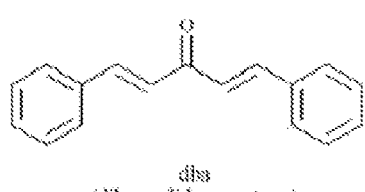

Table 1 summarizes a selection of ligands, bases and solvents that have been evaluated for the metal-catalyzed coupling reaction of the present invention. FIG. 5 illustrates several ligands evaluated in organometallic coupling reactions to convert compounds of Formula VIIIa-1 to compound of Formula Ia-1, and the chemical names for the ligands are provided in Table 2.

TABLE 1

| Ligand | Base | Solvent | % Conversion after 28 hrs |
|---|---|---|---|
| BINAP | $Cs_2CO_3$ | Dioxane | 64 |
| BINAP | $Cs_2CO_3$ | Anisole | 44 |
| Carbene | $Cs_2CO_3$ | Toluene | 2 |
| Carbene | $Cs_2CO_3$ | Dioxane | 4 |
| Cycloh_B | $Cs_2CO_3$ | Anisole | 17 |
| Cycloh_B | $Cs_2CO_3$ | Dioxane | 2 |
| 'B_A_B | $Cs_2CO_3$ | Dioxane | 1 |
| DPPF | $Cs_2CO_3$ | Toluene | 47 |
| DPPF | $K_3PO_4$ | Anisole | 17 |
| DPPF | $Cs_2CO_3$ | Dioxane | 30 |
| DPPF | $Cs_2CO_3$ | Anisole | 49 |
| DPPF | $K_3PO_4$ | Dioxane | 45 |
| DPPF | $Cs_2CO_3$ | TFT | 27 |
| FC_B | $Cs_2CO_3$ | Anisole | 89 |

TABLE 1-continued

| Ligand | Base | Solvent | % Conversion after 28 hrs |
|---|---|---|---|
| FC_B | $K_3PO_4$ | Toluene | 14 |
| FC_B | NaOtBu | NMP | 8 |
| tbut_B | $Cs_2CO_3$ | Dioxane | 2 |
| S Phos | $Cs_2CO_3$ | Dioxane | 12 |
| DPE-phos | $Cs_2CO_3$ | Dioxane | 48 |
| DPE-phos | $Cs_2CO_3$ | Dioxane | 54 |
| DPE-phos | $Cs_2CO_3$ | Toluene | 53 |
| DPE-phos | $Cs_2CO_3$ | Anisole | 59 |
| Verk_B | $Cs_2CO_3$ | Dioxane | 4 |
| Xantphos | $Cs_2CO_3$ | Toluene | 73 |
| Xantphos | $Cs_2CO_3$ | Anisole | 99 |
| Xantphos | $Cs_2CO_3$ | Dioxane | 79 |
| Xantphos | $Cs_2CO_3$ | Dioxane | 60 |
| Xantphos | $Cs_2CO_3$ | Dioxane | 70 |
| Xantphos | $Cs_2CO_3$ | Dioxane | 91 |
| Xantphos | $Cs_2CO_3$ | Dioxane | 99 |
| Xantphos | $K_3PO_4$ | Anisole | 74 |

TABLE 2

| | |
|---|---|
| S Phos | 2-dicyclohexylphosphino-2',6'-dimethoxy-1,1'-biphenyl |
| Cycloh_B | 2-(dicyclohexylphosphino)-2'-(N,N-dimethylamino)-biphenyl |
| $^t$B_A_B | 2-di-t-butylphosphino-2'-(N,N-dimethylamino)biphenyl |
| $^t$But_B | 2-(di-t-butylphosphino)biphenyl |
| VerkB | 2,8,9-tri-i-butyl-2,5,8,9-tetraaza-1-phosphabicyclo[3.3.3]-undecane |
| Carbene | allylchloro[1,3-bis(2,6-di-i-propyl-phenyl)imidazol-2-ylidene]palladium(II) |
| Rac-BINAP | racemic-2,2'-bis(diphenylphosphino)-1,1'-binaphthyl |
| DPPF | 1,1'-bis(diphenylphosphino)ferrocene |
| FC_B | (R)-(-)-1-[(S)-2-(diphenylphosphino)ferrocenyl]ethyldi-t-butylphosphine |
| Xanthphos | 9,9-dimethyl-4,5-bis(diphenylphosphino)xanthene |
| DPE-phos | bis(2-diphenylphosphinophenyl)ether |

In one embodiment a Pd scavenger, for example Silicycle Siliabond Si-Thiourea can be used to reduce the Pd content of the compounds produced by the process of the invention.

Alternatively, the metal-catalyzed coupling reaction can be carried out using a copper catalyst (see F. Y. Kwong, A. Klapars and S. L. Buchwald, *Organic Letters* 2002, 4, 581-584). Examples of suitable copper-based catalysts include, but are not limited to, CuI/ethylene glycol. In one embodiment, the reaction is carried out in an alcoholic solvent, such as isopropanol or 2-butanol, with a simple chelating diol catalyst, such as ethylene glycol.

In an alternative embodiment, the coupling of a compound of Formula VIIIa-1 with an aryl halide to provide a compound of Formula Ia-1 can proceed by direct nucleophilic displacement, optionally in the presence of a base such as a lithium amide, at either ambient or elevated temperature.

Method 2:

In yet another embodiment, the present invention provides a method, referred to herein as Method 2, for preparing compounds of Formula Ia-2 and their synthetic intermediates

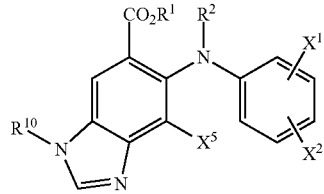

Figure 2:
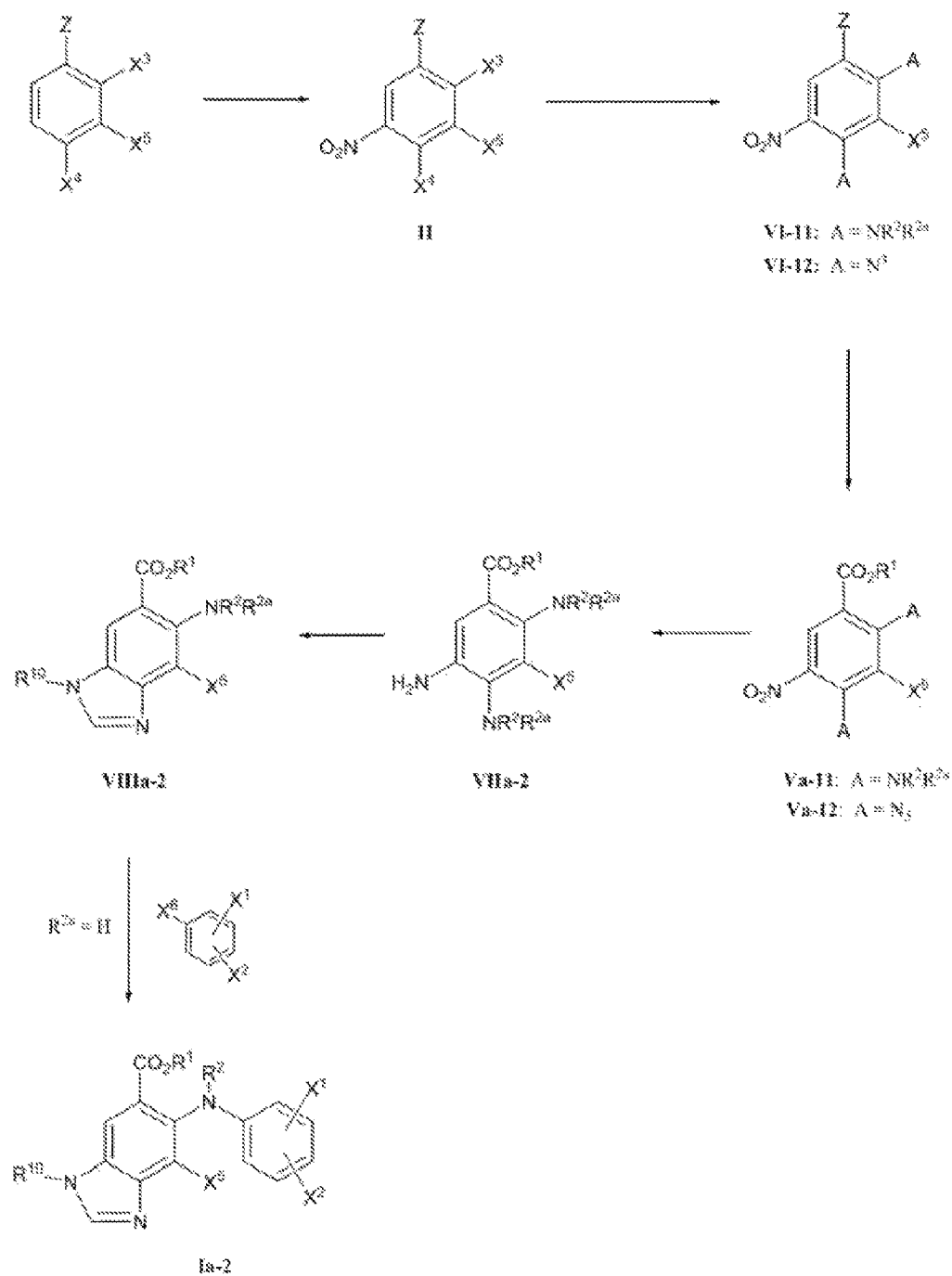
FIG. 2 shows a reaction scheme (Method 2) for the synthesis of compounds having the Formula Ia-2.

Ia-2 and salts and solvates thereof, wherein $R^1$, $R^2$, $R^{10}$, $X^1$, $X^2$ and $X^5$ are as defined herein. Method 2, as illustrated in FIG. 2, follows the diamination route of Method 1, with the exception that the Z group is converted to a —COOR$^1$ group at some point during the synthesis of compounds of Formula Ia-2. For example, as shown in FIG. 2, the Z group of a compound of Formula VI-11 or VI-12 (prepared as described in Method 1)

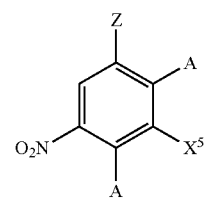

VI-11: A = $NR^2R^{2a}$
VI-12: A = $N_3$ can be converted to the corresponding ester derivative represented by Formula Va-11 or Va-12

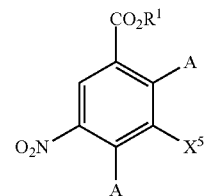

Va-11: A = $NR^2R^{2a}$
Va-12: A = $N_3$ wherein $R^1$, $R^2$, $R^{2a}$ and $X^5$ are as defined herein, by reacting a compound of Formula VI-11 or VI-12 with a compound having the formula $R^1OH$, optionally in the presence of an activating agent that activates said Z group towards reaction with the compound of formula $R^1OH$, wherein $R^1$ is as defined herein. Examples of activating agents suitable for purposes of this invention include, but are not limited to, the activating agents listed above for Method 1, including (a) mineral and organic acids; (b) reagents capable of converting a carboxylic acid into an acid chloride including, but not limited to, halogenating agents; (c) carbodiimides; (d) trialkylsilyl halides; (e) chloroformates and (f) dialkylazodicarboxylates alone or together with a phosphine reagent.

Compounds of Formulas Va-11 and Va-12 can be converted to a compound of Formula Ia-2 in a manner similar to that described in Method 1. More specifically, as shown in FIG. 2, one embodiment for the conversion of a compound of Formula Va-11 or Va-12 to a compound of Formula Ia-2 comprises:

(i) reducing said compound of Formula Va-11 or Va-12 to provide a compound of Formula VIIa-2

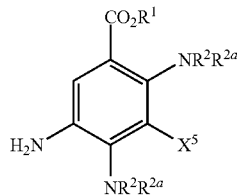

VIIa-2 wherein $R^1$, $R^2$, $R^{2a}$ and $X^5$ are as defined herein, and wherein when A of said compound of Formula Va-11 or Va-12 is —NH-benzyl, —NHOR$^1$, —NHNHR$^1$ or $N_3$, then $R^2$ and $R^{2a}$ of Formula VIIa-2 are hydrogen;

(ii) when $R^{2a}$ is hydrogen, cyclizing said compound of Formula VIIa-2 using methods such as, but not limited to, any one of cyclization Methods A-E described herein, to provide a compound of Formula VIIIa-2

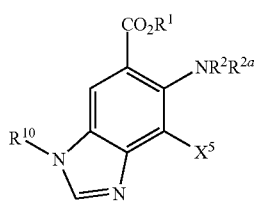

VIIIa-2 wherein $R^1$, $R^2$, $R^{2a}$, $R^{10}$ and $X^5$ are as defined herein; and (iii) when $R^{2a}$ is hydrogen, coupling the benzimidazole represented by Formula VIIIa-2 with a compound having the Formula

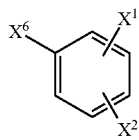

wherein $X^1$, $X^2$ and $X^6$ are as defined herein, optionally either (i) at elevated temperature and optionally in the presence of a base, or (ii) in the presence of a metal-based catalyst and a base, to provide said compound of Formula Ia-2. In certain embodiments, $X^1$, $X^2$ and $X^6$ are independently F, Cl, Br, or I. In certain embodiments, $X^1$ is Br. In certain embodiments, $X_2$ is Cl. In another embodiment, $X^6$ is iodo. In a particular embodiment, the compound of Formula VIIIa-2 is reacted with is 4-bromo-2-chloroiodobenzene.

In one embodiment, the synthesis of compounds of VIIIa-2 from compounds of Formula Va-11 or Va-12 is performed without isolation of the intermediate compound VIIa-2. In other embodiment, the intermediate compound of Formula VIIa-2 is isolated.

While Method 2 as illustrated in FIG. 2 shows the conversion of the Z group to a COOR$^1$ group during the preparation of a compound of Formula Va-11 or Va-12 from a compound of Formula VI-11 or VI-12, it is to be understood that FIG. 2 shows only one of several embodiments of Method 2 for ease of explanation. That is, the Z group can be converted to COOR$^1$ at any point during the process of Method 2.

Figure 3:
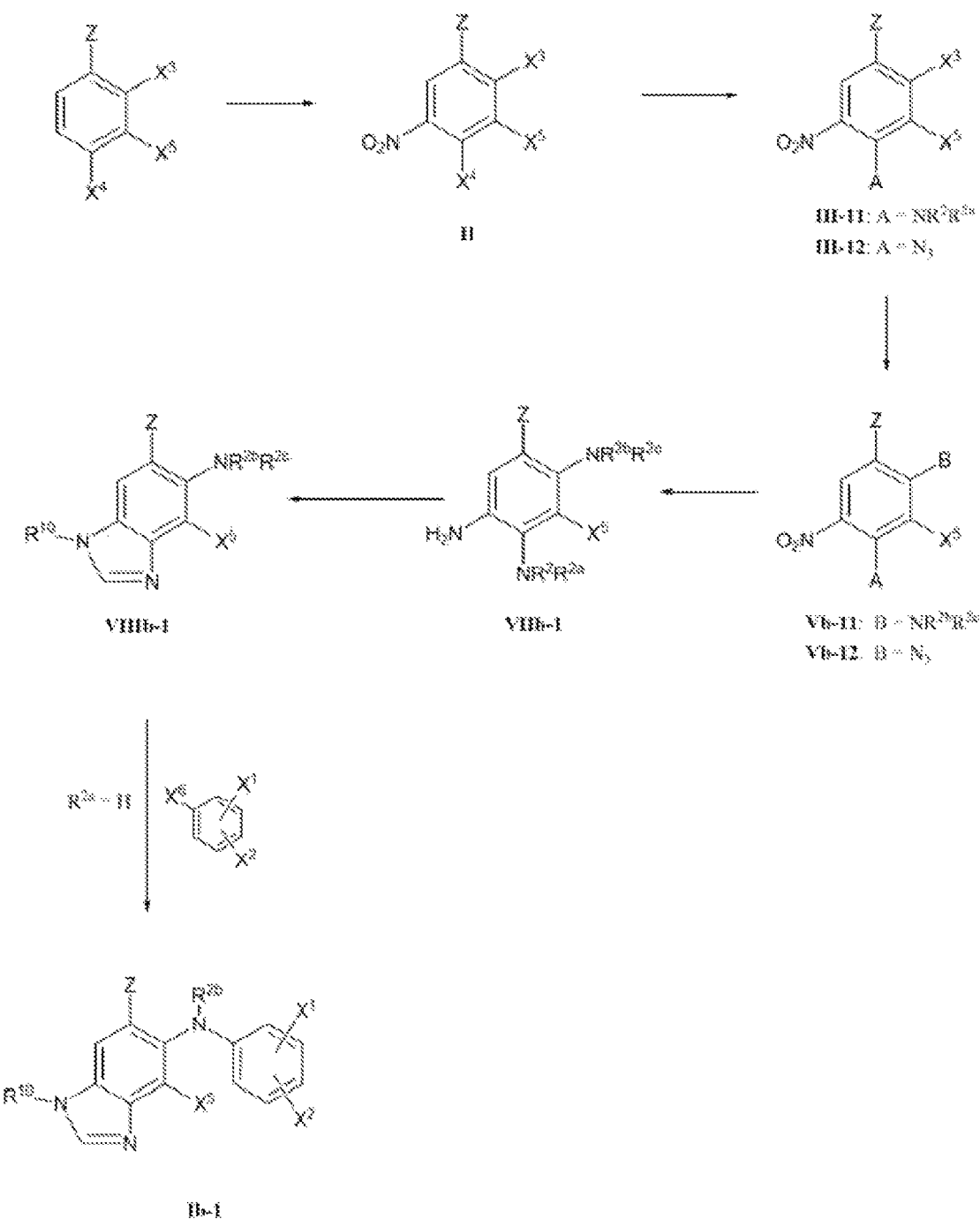
FIG. 3 shows a reaction scheme (Method 3) for the synthesis of compounds having the Formula Ib-1.

Method 3:

In yet another embodiment, the present invention provides a stepwise amination method, referred to herein as Method 3 and shown generally in FIG. 3, for the preparation of compounds of Formula Ib and their synthetic intermediates

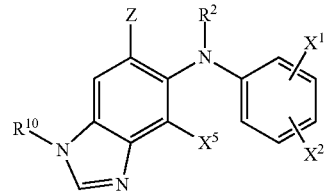

Ib-1 and salts and solvates thereof, wherein Z, $X^1$, $X^2$, $X^5$, $R^{2b}$ and $R^{10}$ are as defined herein. In general, according to one embodiment of the invention, a method for preparing a compound of Formula Ib-1 according to Method 3 comprises nitrating a compound having the Formula

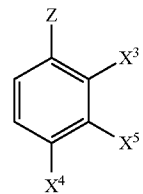

wherein $X^3$, $X^4$, $X^5$ and Z are as defined herein, to provide a compound of Formula II

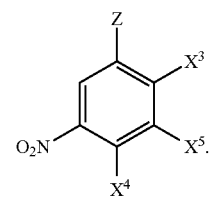

II

Nitration reaction conditions are well known to those skilled in the art. For example, in one embodiment a trihalobenzoic acid can be treated with fuming nitric acid in $H_2SO_4$ to provide a 2,3,4-trihalo-5-nitrobenzoic acid.

Compounds of Formula II are then converted to compounds of Formula III-11 or III-12 by a stepwise amination process. A useful discovery was that the $X^3$ and $X^4$ groups of compounds represented by Formula II can be replaced independently. That is, the leaving group at the position ortho- to the nitro group in the compound of Formula II can be selectively replaced by a nitrogen nucleophile, in high yield, under carefully controlled conditions. The leaving group at the position para- to the nitro group can then be displaced by a second nucleophile at a convenient stage later in the synthetic route. Examples of selective stepwise mono-aminations are illustrated herein for Method 3 as well as in Method 4.

More specifically, in one embodiment a compound of Formula II is reacted with (i) a reagent that contains or generates ammonia, (ii) a primary or secondary amine other than an aromatic amine or (iii) a reagent that delivers a group that can subsequently be converted into an amine, under conditions that allow selective displacement of $X^4$, to provide a compound of Formula III-11, or said compound of Formula II is reacted with (iv) a metal azide under conditions that allow selective displacement of $X^4$ to provide a compound of Formula III-12

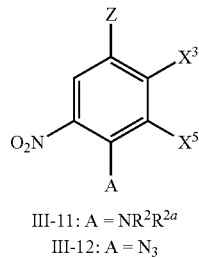

III-11: A = $NR^2R^{2a}$
III-12: A = $N_3$ wherein $X^3$, $X^5$, $R^2$, $R^{2a}$ and Z are as defined herein. In certain embodiments, $R^{2a}$ is a nitrogen protecting group such as substituted or unsubstituted benzyl, allyl or —C(O)OR$^6$. In another embodiment, $R^2$ and/or $R^{2a}$ is hydrogen.

Nucleophilic substitution of a halide or sulfonate ester ortho- or para- to a nitro group in an aromatic ring is a method well known in the art for the introduction of an amino group into an aromatic ring. The reaction conditions needed to achieve selective mono-amination at the position para- to the Z group depend on the type of nucleophile used in the mono-amination reaction. For example, if a strong nucleophile such as is used, the reaction may proceed easily at or below room temperature and at atmospheric pressure using one equivalent of the nucleophile to provide the desired mono-amination product. Examples of strong nucleophiles include, but are not limited to, aqueous ammonia (30% vol/vol) and metal amides such as sodium, potassium and lithium amide. Alternatively, if a weak nucleophile is used, more forcing conditions such as elevated temperatures and/or elevated pressure and/or an excess amount of the nucleophile may be required to achieve monoamination. Examples of weak nucleophiles include, but are not limited to, a primary or secondary amine substituted with a sterically bulky group such as t-butyl. The introduction of an amino group ortho- to the nitro groups causes the substitution product represented by Formula III-11 or III-12 to be less reactive to further nucleophilic attack at the position para- to the nitro group, so the reaction can be carried out with a high level of selectivity.

For example, according to one embodiment a compound of Formula III-11 can be prepared by reacting a compound of Formula II with NH$_4$OH at temperatures between 0° C. and room temperature in water (with or without an organic co-solvent) followed by acidification to pH between 0 and 7. Examples of suitable organic co-solvents include THF, 1,4-dioxane and N-methylpyrrolidine. In certain embodiments, a compound of Formula III-11 is prepared by reacting a compound of Formula II with excess NH$_4$OH in water at room temperature. The acidification can be accomplished by the addition of an acid such as, but not limited to, a dilute or concentrated mineral acid or a carboxylic acid such as acetic acid. In one embodiment, the above-described preparation of a compound of Formula III-11 or III-12 is performed without isolation of the intermediate compound. In another embodiment, the intermediate compound represented by Formula II is isolated.

Examples of reagents that contain or generate ammonia for preparing a compound of Formula III-11 or III-12 include, but are not limited to, NH$_3$ and NH$_4$OH. Examples of primary and secondary amines suitable for purposes of this invention include amines having the formula HNR$^2$R$^{2a}$, wherein R$^2$ and R$^{2a}$ are as defined herein. Specific examples of primary and secondary amines include, but are not limited to methylamine, benzylamine, dibenzylamine, allylamine, diallylamine and hexamethyldisilazane. Examples of reagents that deliver a group that can subsequently be converted into an amine include, but are not limited to, (1) metal amides such as sodium, potassium and lithium amide, or alkylated derivatives thereof, (2) protected ammonia or amide equivalents such as, but not limited to, hydroxylamines and hydrazines, (3) nitrogen nucleophiles having the Formula MNR$^2$R$^{2a}$ wherein M is a metal such as Na, K, Li, Cs, Mg or Al, and (4) metal silylamides such as lithium (bis)(trimethylsilyl)amide, sodium (bis)(trimethylsilyl)amide or potassium (bis)(trimethylsilyl)amide. Examples of metal azides include, but are not limited to, sodium azide (NaN$_3$), potassium azide (KN$_3$) and lithium azide (LiN$_3$).

This invention further provides compounds of Formula III and salts and solvates thereof. In some embodiments of compounds of Formula III, Z is COOR$^1$ or —C(=O)NR$^6$R$^7$. In certain embodiments, R$^6$ is —OR$^8$ and R$^7$ is H. In particular embodiments, R$^8$ is —(CH$_2$)$_2$—OH. In some embodiments, X$^5$ is halogen. In particular embodiments, X$^5$ is F. In certain embodiments, A is —NH$_2$.

With continued reference to FIG. 3, the compound of Formula III-11 or III-12 is reacted, optionally at elevated temperatures, with (i) a reagent that contains or generates ammonia, (ii) a primary or secondary amine other than an aromatic amine or (iii) a reagent that delivers a group that can subsequently be converted into an amine to provide a compound having Formula Vb-11 wherein B is —NR$^{2b}$R$^{2c}$ and A is —NR$^2$R$^{2a}$ or N$_3$, or said compound of Formula III-11 or III-12 is reacted with (iv) a metal azide, optionally at elevated temperatures, to provide a compound of Formula Vb-12 wherein B is N$_3$ and A is —NR$^2$R$^{2a}$ or N$_3$,

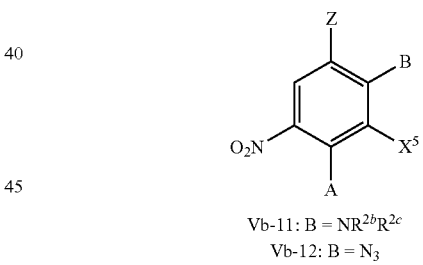

Vb-11: B = $NR^{2b}R^{2c}$
Vb-12: B = $N_3$ wherein Z, X$^5$, R$^2$, R$^{2a}$, and R$^{2b}$ are as defined herein and R$^{2c}$ is hydrogen, C$_1$-C$_{10}$ alkyl, C$_2$-C$_{10}$ alkenyl, C$_2$-C$_{10}$ alkynyl, benzyl, allyl, arylalkyl, trialkylsilyl, dialkylarylsilyl, —COR$^6$, —C(O)OR$^6$, —C(O)NR$^6$R$^7$, —OR$^1$ or —NHR$^1$, wherein said alkyl, alkenyl, alkynyl, benzyl, allyl and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl. In a particular embodiment, X$^5$ is F.

According to one embodiment, the amination reaction is performed by reacting a compound of Formula III with a suitable nitrogen nucleophile using methods well known to those skilled in the art. Nitrogen nucleophiles suitable for purposes of this invention include, but are not limited to, (i) reagents that contain or generate ammonia (including, but not limited to, NH$_3$ and NH$_4$OH); (ii) primary and secondary amines having the formula HNR$^{2b}$R$^{2c}$, wherein R$^2$ and R$^{2a}$ are as defined herein; (iii) metal azides including, but not limited to, (NaN$_3$), potassium azide (KN$_3$) and lithium azide (LiN$_3$) and (iv) reagents that deliver a group that can subsequently be converted into an amine include, but are not limited to, protected ammonia or amide equivalents such as, but not limited to, hydroxylamines and hydrazines, (3) nitrogen nucleophiles having the Formula MNR$^{2b}$R$^{2c}$ wherein M is a metal such as Na, K, Li, Cs, Mg or Al; and metal silylamides such as lithium (bis)(trimethylsilyl)amide, sodium (bis)(trimethylsilyl)amide or potassium (bis)(trimethylsilyl)amide. The reaction can be performed in any suitable organic or inorganic solvent at temperatures ranging from −20° C. to 200° C. Typically the reaction is performed at elevated temperatures in the range of about 30 and 130° C., more preferably at temperatures between 50 and 95° C.

For example, in one embodiment a compound of Formula Vb-11 wherein A=B=NH$_2$ can be obtained by reaction of a compound of Formula III with aqueous ammonia in an organic solvent such as, but not limited to, tetrahydrofuran, dioxane or N-methyl pyrrolidinone, at elevated temperature, for example, between 30 and 130° C., and as a further example between 55-90° C. under a slight pressure of ammonia (for example between 1 to 5 bar).

The nitro group of the compound of Formula Vb-11 or Vb-12 is then reduced to provide a compound of Formula VIIb-1

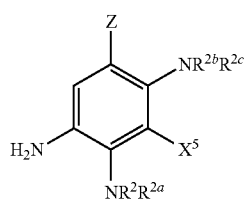

VIIb-1 wherein Z, R$^2$, R$^{2a}$, R$^{2b}$, R$^{2c}$ and X$^5$ are as defined herein. In embodiments of Method 3 wherein A and/or B is N$_3$, —NH-benzyl, —NHOR$^1$ or —NHNHR$^1$, then NR$^2$R$^{2a}$ and/or NR$^{2b}$R$^{2c}$ group of the compound of Formula VIIb-1 is —NH$_2$. The reduction step can be performed utilizing reaction conditions and reagents known to those skilled in the art. Examples of suitable methods for reducing an aromatic nitro group include, but are not limited to, dissolving metal reductions, catalytic hydrogenations, and enzymatic reactions as described above.

This invention further provides compounds of Formula VIIb-1 and salts and solvates thereof.

When R$^{2a}$ is hydrogen, compounds of Formula VIIb-1 can be cyclized to provide the benzimidazole derivative represented by Formula VIIIb-1

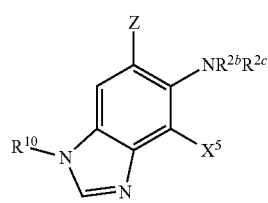

VIIIb-1 wherein Z, R$^{2b}$, R$^{2c}$, R$^{10}$ and X$^5$ are as defined herein. The cyclization step to provide the benzimidazole core structure can be performed in several ways, such as any one of cyclization Methods A-E as described herein.

This invention further provides compounds of Formula VIIIb-1 and salts and solvates thereof.

When R$^{2c}$ is hydrogen, the benzimidazole represented by Formula VIIIb-1 is optionally isolated or directly converted to compound of Formula Ib-1 without isolation by reacting the compound of Formula VIIIb-1 with a compound having the formula

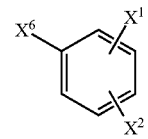

optionally either (i) at elevated temperature and optionally in the presence of a base, or (ii) in the presence of a metal-based catalyst and a base, wherein X$^1$, X$^2$ and X$^6$ are as defined herein, to provide said compound of Formula Ib-1. The coupling reaction can be performed generally as described for Method 1, using any suitable metal-based catalyst. Suitable catalysts include, but are not limited to, copper-based and palladium-based catalysts. Illustrative examples of suitable organopalladium catalysts include, but are not limited to, Pd(OAc)$_2$ and Xantphos, Pd(OAc)$_2$ and DPE-phos, Pd$_2$(dba)$_3$ and Xantphos, Pd$_2$(dba)$_3$ and DPE-phos, palladium tetrakis(triphenylphosphine), and palladium dichloride [bis(diphenylphosphino)ferrocene]. Preferred catalysts include organopalladium catalysts such as Pd$_2$(dba)$_3$ in combination with Xantphos or DPE-phos, and Pd(OAc)$_2$ in combination with Xantphos or DPE-phos.

Method 4:

In yet another embodiment, the present invention provides a method, referred to herein as Method 4, for preparing compounds of Formula Ib-2 and their synthetic intermediates

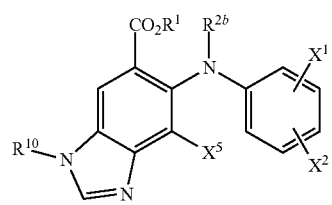

Figure 4:
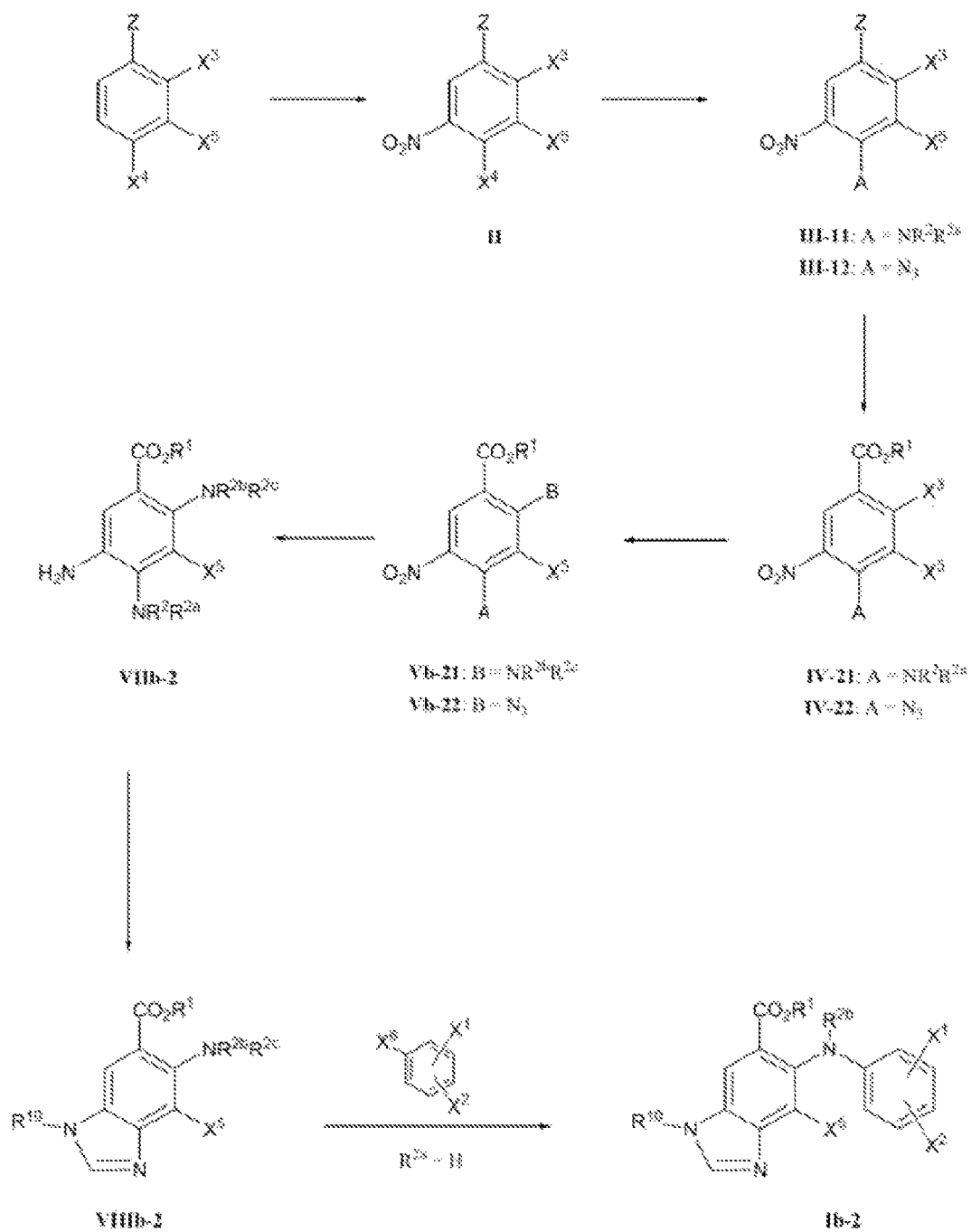
FIG. 4 shows a reaction scheme (Method 4) for the synthesis of compounds having the Formula Ib-2.

Ib-2 and salts and solvates thereof, wherein R$^1$, R$^{2b}$, R$^{10}$, X$^1$, X$^2$ and X$^5$ are as defined herein. Method 4, which is illustrated in FIG. 4, follows the stepwise amination route of Method 3, with the exception that the Z group is converted to a COOR$^1$ group at some point during the synthesis. For example, as shown in FIG. 4, the Z group of a compound of Formula III-11 or III-12 (prepared as described in Method 3)

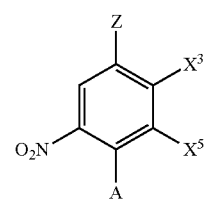

III-11: A = NR$^2$R$^{2a}$
III-12: A = N$_3$ can be converted to the corresponding ester derivative represented by Formula IV-21 or IV-22

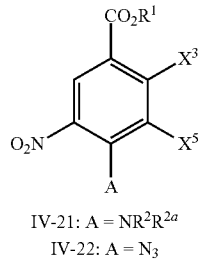

IV-21: A = NR²R²ᵃ
IV-22: A = N₃ by reacting said compound of Formula III-11 or III-12 with a compound having the formula $R^1OH$, wherein $R^1$ is as defined herein, optionally in the presence of an activating reagent that activates the Z group towards reaction with said compound of formula $R^1OH$, under reaction conditions well known to those skilled in the art. Examples of activating agents suitable for purposes of this invention include, but are not limited to, (a) mineral and organic acids; (b) reagents capable of converting a carboxylic acid into an acid chloride including, but not limited to, halogenating agents such as $SOCl_2$ or $(COCl)_2$, alkyl chloroformates, aryl chloroformates and acid chlorides (such as trimethylacetyl chloride); (c) carbodiimides including, but not limited to, dicyclohexylcarbodiimide (DCC); (d) trialkylsilyl halides including, but not limited to, trimethylsilyl chloride ($Me_3SiCl$); and (e) dialkylazodicarboxylates such as, but not limited to, diethylazodicarboxylate (DEAD), typically in conjunction with a phosphine reagent such as, but not limited to, $Ph_3P$. In a particular embodiment, a compound of Formula III-11 or III-12 where Z is COOH can be converted into a methyl ester derivative represented by Formula IV-21 or IV-22 by reaction with methanol in the presence of trimethylsilyl chloride.

A compound of Formula IV-21 or IV-22 is then reacted, optionally at elevated temperatures, with (i) a reagent that contains or generates ammonia, (ii) a primary or secondary amine other than an aromatic amine or (iii) a reagent that delivers a group that can subsequently be converted into an amine to provide a compound of Formula Vb-21 wherein A is —$NR^{2b}R^{2c}$ or $N_3$, or said compound of Formula IV-21 or IV-22 is reacted with (iv) a metal azide, optionally at elevated temperatures, to provide a compound of Formula Vb-22 wherein A is —$NR^{2b}R^{2c}$ or $N_3$,

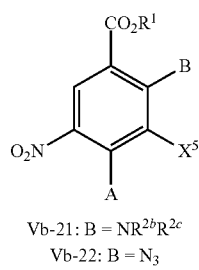

Vb-21: B = NR²ᵇR²ᶜ
Vb-22: B = N₃ wherein $R^1$, $R^{2b}$, $R^{2c}$, $R^{10}$, $X^1$, $X^2$ and $X^5$ are as defined herein. The reaction can be performed in any suitable organic or inorganic solvent at temperatures ranging from −20° C. to 200° C. Typically the reaction is performed at elevated temperatures in the range of about 30 and 130° C., more preferably at temperatures between 50 and 95° C. For example, in one embodiment a compound of Formula Vb-21 can be obtained by reaction of a compound of Formula IV-21 or IV-22 with aqueous ammonia in an organic solvent such as, but not limited to, tetrahydrofuran, dioxane or N-methylpyrrolidinone at elevated temperature and under a slight pressure of ammonia (for example between 1 to 5 bar).

This invention also includes compound of Formula Vb-21 and Vb-22. In one particular embodiment, $R^1$ is $C_1$-$C_{10}$ alkyl. In another embodiment, $R^1$ is methyl. According to one embodiment, the compound of Formula Vb-21 is a 2,4-diamino-3-fluoro-5-nitrobenzoic acid ester. In a particular embodiment, the compound of Formula Vb-21 is methyl 2,4-diamino-3-fluoro-5-nitrobenzoate.

With continued reference to FIG. 4, carboxylic acid esters represented by Formula Vb-21 or Vb-22 can be utilized to prepare compounds of Formula Ib-2 by the method comprising:

(i) reducing the compound of Formula Vb-21 or Vb-22 utilizing reaction conditions known in the art, such as those described for Method 1, to provide a compound represented by Formula VIIb-2

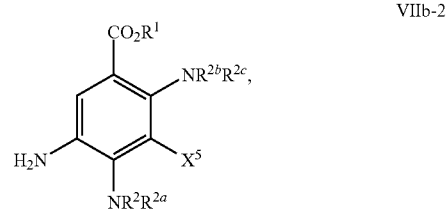

wherein when A and/or B of Formula Vb-21 or Vb-22 is —NH-benzyl, —$NHOR^1$, —$NHNHR^1$, or $N_3$, then $R^2$ and $R^{2a}$ and/or $R^{2b}$ and $R^{2b}$, respectively, of Formula VIIb-2 are hydrogen;

(ii) when $R^{2a}$ is hydrogen, cyclizing said compound of Formula VIIb-2 using methods such as, but not limited to, any one of Methods A-E described herein, to provide a compound of Formula VIIIb-2

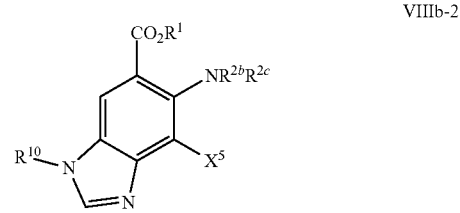

wherein $R^1$, $R^2$, $R^{2b}$, $R^{2c}$, $R^{10}$ and $X^5$ are as defined herein; and (iii) when $R^{2c}$ is hydrogen, coupling said compound of Formula VIIIb-2 with a reagent having the Formula

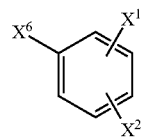

optionally either (i) at elevated temperature and optionally in the presence of a base, or (ii) in the presence of a metal-based catalyst and a base, wherein $X^1$, $X^2$ and $X^6$ are as defined herein, using reaction conditions such as those described for Method 1, to provide said compound of Formula Ib-2.

According to one embodiment of the present invention, a process for the conversion of a compound of Formula VIIIb-2 into a compound of Formula Ib-2 comprises a coupling reaction between said compound of Formula VIIIb-2 and an aryl halide in the presence of a suitable metal-based catalyst and a base in an appropriate solvent. In one embodiment, the aryl halide has the Formula

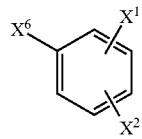

wherein $X^1$, $X^2$ and $X^6$ are as defined herein. The coupling reaction can be performed generally as described for Method 1. The preparation of compounds of Formula VIIIb-2 from compounds of Formula Vb-2 as described in Method 4 can be prepared in one pot or in a step-wise manner.

While Method 4 as illustrated in FIG. 4 shows the conversion of the Z group to a —COOR$^1$ group during the preparation of a compound of Formula IV-21 or IV-22 from a compound of Formula III-11 or III-12, it is to be understood that FIG. 4 shows only one of several embodiments of Method 4 for ease of explanation. That is, the Z group can be converted to —COOR$^1$ at any point during the process of Method 4.

This invention further provides compounds of Formula VIIb-2 and VIIIb-2 and salts and solvates thereof.

Yet another embodiment of the present invention provides a method, referred to herein as Method 5, for preparing N–1 benzimidazole compounds represented by Formula Ic-1 and their synthetic intermediates

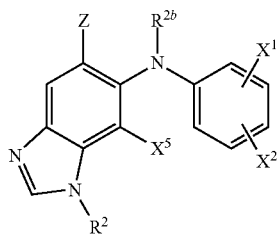

Ic-1 and salts and solvates thereof, wherein Z, $R^{2b}$, $X^1$, $X^2$ and $X^5$ are as defined herein and $R^2$ is not hydrogen, said method comprising:

cyclizing a compound of Formula VIIb-1

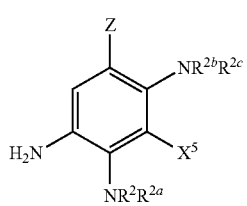

VIIb-1 prepared as described in Method 3, wherein $R^{2a}$ is hydrogen and Z, $R^{2b}$, $R^{2c}$ and $X^5$ are as defined herein, to provide a compound of Formula XIb-1

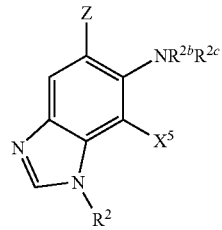

XIb-1 wherein Z, $R^2$, $R^{2b}$, $R^{2c}$, $R^{10}$ and $X^5$ are as defined herein; and when $R^{2c}$ is hydrogen, coupling said compound of Formula XIb-1 with a reagent having the formula

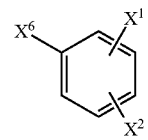

optionally either (i) at elevated temperatures and optionally in the presence of a base, or (ii) in the presence of a metal-based catalyst and a base, wherein $X^1$, $X^2$ and $X^6$ are as defined herein, to provide said compound of Formula Ic-1.

Methods 1-5 of the present invention provide a number of distinct advantages over conventional processes for preparing compounds of the general Formulas Ia-1, Ib-1 and Ic-1. For example, the processes of the present invention provide compounds of the general Formulas Ia-1, Ib-1 and Ic-1 in higher yields compared to conventional processes. Further, the invention provides methods for the regioselective and chemoselective cyclization of compounds of Formulas VIIa-1 and VIIb-1 to provide benzimidazoles of Formulas VIIIa-1 and VIIIb-1, respectively. In addition, the process of the present invention is more reliable and suitable for the large-scale synthesis of benzimidazoles than conventional processes. For example, the conversion of a compound of Formula VIIa-1 or VIIb-1 to a compound of Formula VIIIa-1 or VIIIb-1, respectively, according to the methods of the present invention produces far less toxic by-products than methods utilized in the prior art for the synthesis of benzimidazole ring systems, and is a more efficient process. The synthetic methods of the present invention are selective and the preparation of compounds of this invention can be carried out in high yield, thus providing industrial value. Furthermore, benzimidazole derivatives represented by Formulas VIIIa-1, VIIIb-1, Ia-1, Ib-1 and Ic-1 can be synthesized from trihalobenzoic acids in a relatively short number of steps.

Benzimidazole Cyclizations

As stated, the cyclization of compounds of Formulas VIIa-1, VIIa-2, VIIb-1 and VIIb-2 in any of Methods 1-5 of the present invention to provide benzimidazole core structures can be performed in several ways. Several methods, namely Methods A-E, are described below and are illustrated in FIGS. 6-10. While Methods A-E are described specifically with respect to the cyclization of a compound of Formula VIIb-1 for ease of explanation, it is to be understood that Methods A-E also apply equally to the cyclization of compounds of Formulas VIIa-1, VIIa-2 and VIIb-2. The cyclization methods will provide either N-3 benzimidazole derivatives or N-1 benzimidazole derivatives, depending on the reagents used and the particular $R^2$ and $R^{2a}$ substituents on the compounds of Formulas VIIa-1, VIIa-2, VIIb-1 and VIIb-2

Figure 6:
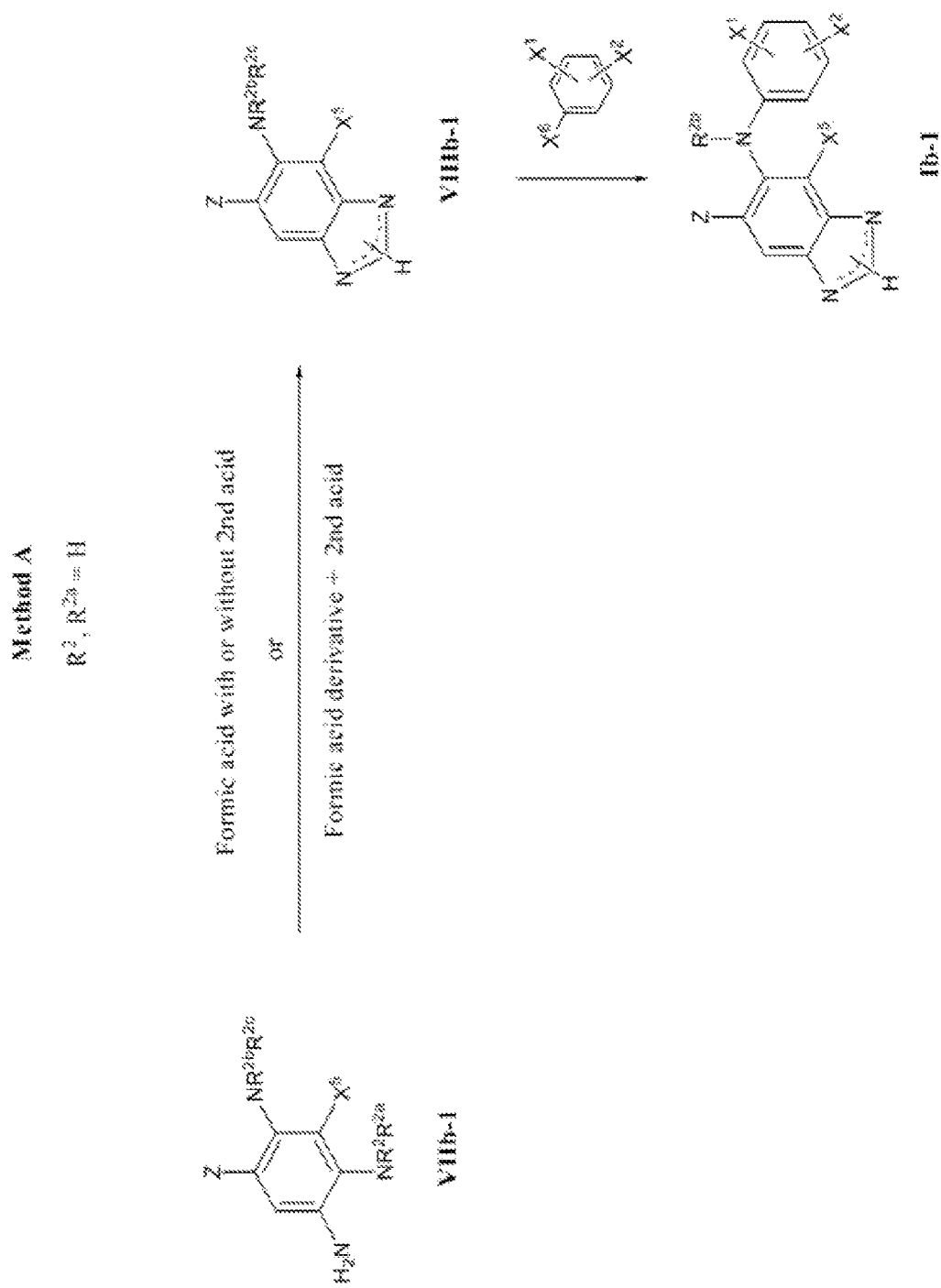
FIG. 6 shows a "one pot" cyclization method (Method A) using formic acid or a formic acid derivative for the preparation of benzimidazole core structures represented by Formula Ib-1.

Method A:

According to cyclization Method A as shown in FIG. 6, a compound of Formula VIIb-1, where $R^2$ and $R^{2a}$ are hydrogen, can be cyclized to the corresponding benzimidazole tautomer represented by Formula VIIIb-1

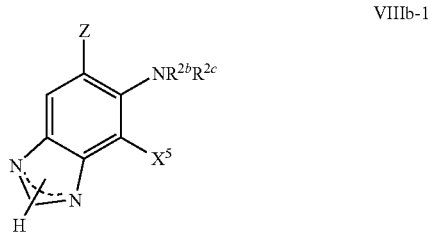

VIIIb-1

(i.e., wherein $R^{10}$ is hydrogen) according to a "one-pot" process which comprises reacting a compound of Formula VIIb-1 with (i) formic acid optionally in the presence of an additional acid, or (ii) a formic acid derivative in the presence of an acid under appropriate conditions known to those skilled in the art. As used herein, the term "formic acid derivative" includes, but is not limited to, esters of formic acid such as, but not limited to, trimethylorthoformate, triethylorthoformate, and formamidine acetate. For example, in one embodiment, a compound of Formula VIIb-1 (wherein Z is $CO_2Me$, and $R^2$ and $R^{2a}$ are H) was converted into a compound of Formula VIIIb-1 (wherein Z is $CO_2Me$) in very high yield upon reaction with methyl orthoformate and sulfuric acid in THF solution.

Figure 7:
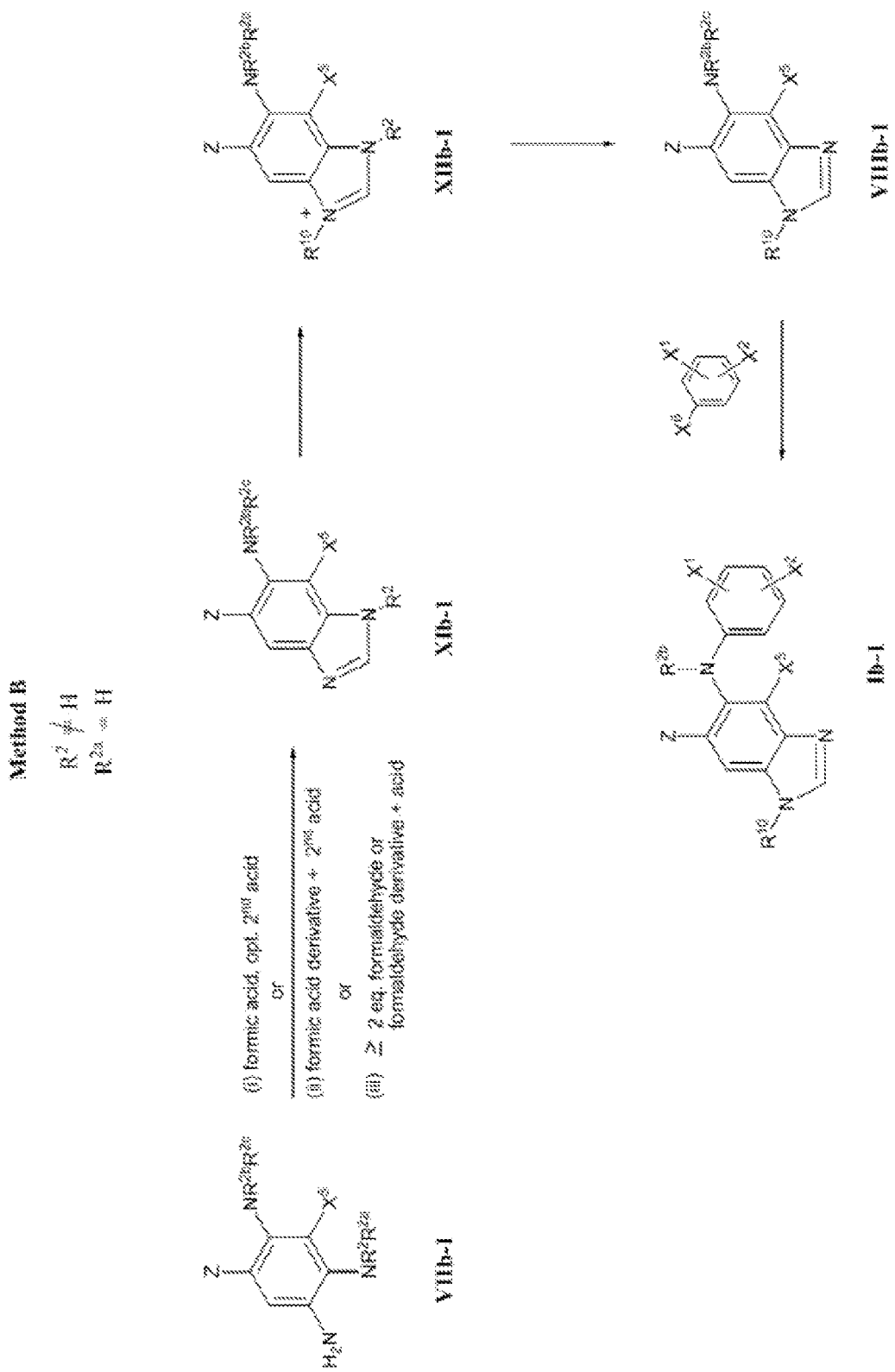
FIG. 7 shows a multi-step cyclization method (Method B) using formic acid or a formic acid derivative for the preparation of benzimidazole core structures represented by Formula Ib-1.

Method B:

According to Method B, as illustrated in FIG. 7, compound of Formula VIIb-1, wherein $R^{2a}$ is hydrogen and $R^2$ is not hydrogen, can be cyclized to the corresponding N-3 benzimidazole represented by Formula VIIIb-1 by a multi-step method upon treatment with (i) formic acid, optionally in the presence of an additional acid, (ii) a formic acid derivative (for example, a formic acid ester such as trimethylorthoformate, triethylorthoformate, or formamidine acetate) in the presence of an acid, or (iii) formaldehyde or a formaldehyde derivative in the presence of an acid, to provide an intermediate N-1 benzimidazole compound represented by the Formula XIb-1. As used herein, the term "formaldehyde derivative" includes, but is not limited to, dialkoxymethanes such as diethoxymethane and dimethoxymethane.

Alkylation of the compound of Formula XIb-1 provides the benzimidazolium ion represented by the compound of Formula XIIb-1. Removal of the N-1 substituent (i.e., the $R^2$ substituent) from the compound of Formula XIIb-1 provides the N-3 benzimidazole compound represented by Formula VIIIb-1, which can undergo an arylation reaction such as described in Method 1 to provide the N-3 benzimidazole compound represented by Formula Ib-1.

Methods for removing N-1 substituents benzimidazoles are well known to persons skilled in the art, and the reagents and reaction conditions required depend on the nature of the $R^2$ group. For example, when the $R^2$ group of a compound of Formula XIIb-1 is substituted or unsubstituted benzyl, allyl or $COOR^6$ wherein $R^6$ is benzyl, removal of the $R^2$ group can be achieved by hydrogenation. An N-1 allyl substituent can also be removed by heating a compound of Formula XIIb-1 in the presence of an organometallic catalyst such as $Rh(PPh_3)_3Cl$ (also known as Wilkinson's catalyst).

Figure 8:
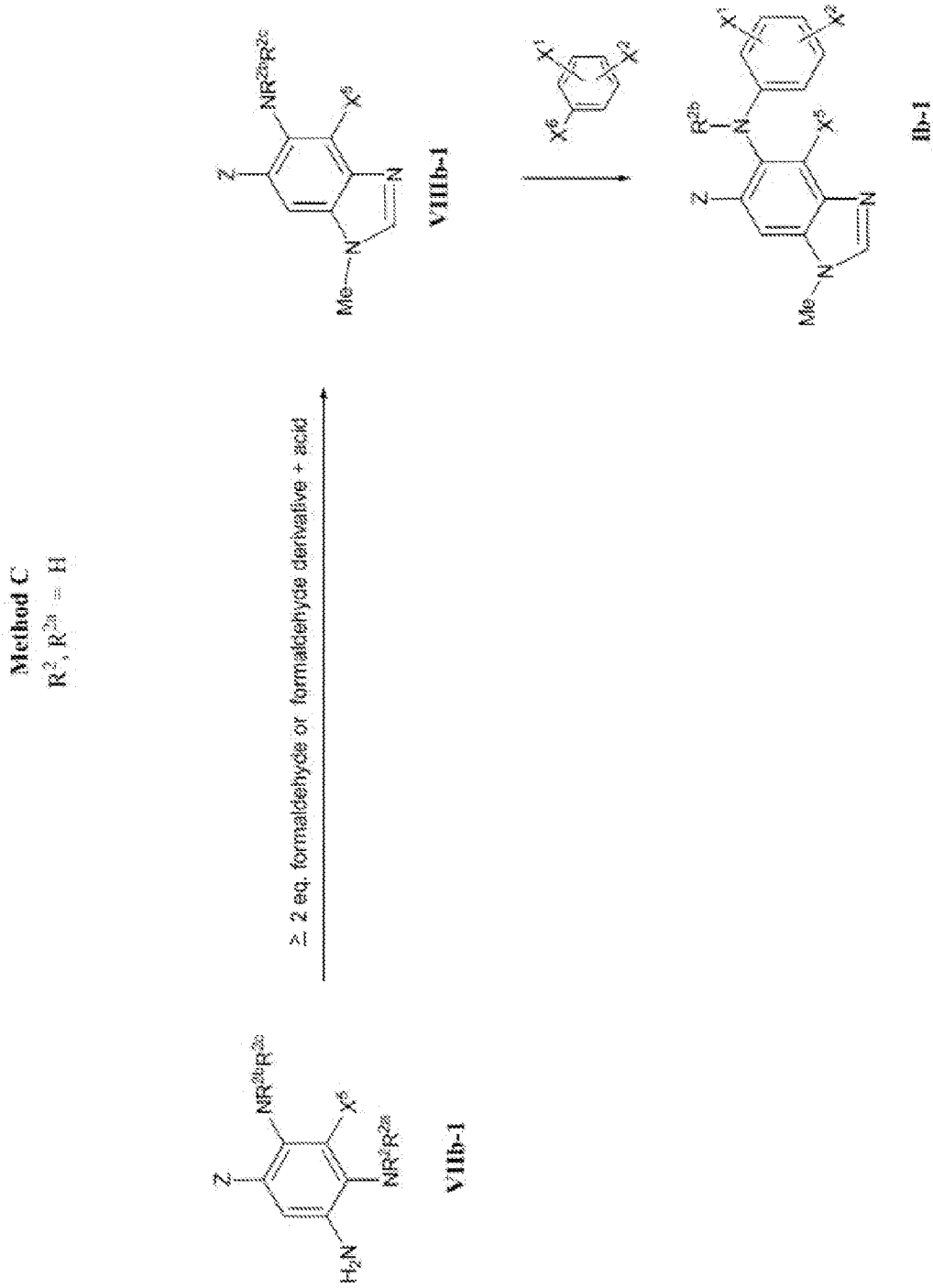
FIG. 8 shows a "one pot" cyclization method (Method C) using formaldehyde or a formaldehyde derivative for the preparation of benzimidazole core structures represented by Formula Ib-1.

Method C:

Cyclization Method C, as shown in FIG. 8, provides a "one pot" method of selectively and directly converting a compound of Formula VIIb-1, where $R^2$ and $R^{2a}$ are hydrogen, to an N-3 benzimidazole derivative represented by Formula VIIIb-1

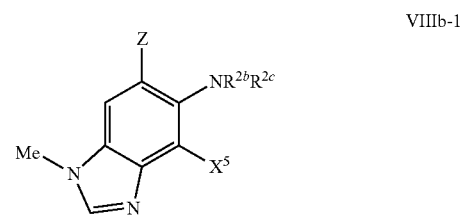

VIIIb-1 wherein $R^{10}$ is methyl. Method C comprises treating a compound of Formula VIIb-1 with (i) two or more equivalents of formaldehyde or a formaldehyde derivative in the presence of an acid. Suitable formaldehyde derivatives include, but are not limited to, dialkoxymethanes such as diethoxymethane and dimethoxymethane. Suitable acids for purposes of this invention include mineral acids (e.g., sulfuric acid, HCl, HBr), sulfonic acids (methanesulfonic acid, toluenesulfonic acid, etc.) or carboxylic acids such as formic acid or acetic acid. In one non-limiting embodiment, the reaction is performed in acetonitrile containing some water and diethoxymethane or dimethoxymethane in the presence of an acid such as toluenesulfonic acid. This reaction advantageously proceeds with complete regioselectivity to provide N-3 methyl benzimidazoles represented by Formula VIIIb-1. Another advantageous feature of this process is that the formaldehyde does not appear to react with the amino group ortho to the Z group of compounds represented by Formula VIIIb-1. Furthermore, the reaction conditions avoid the production of bis-chloromethyl ether as a by-product. This by-product is a carcinogen, and its production on an industrial scale is highly undesirable.

Figure 9:
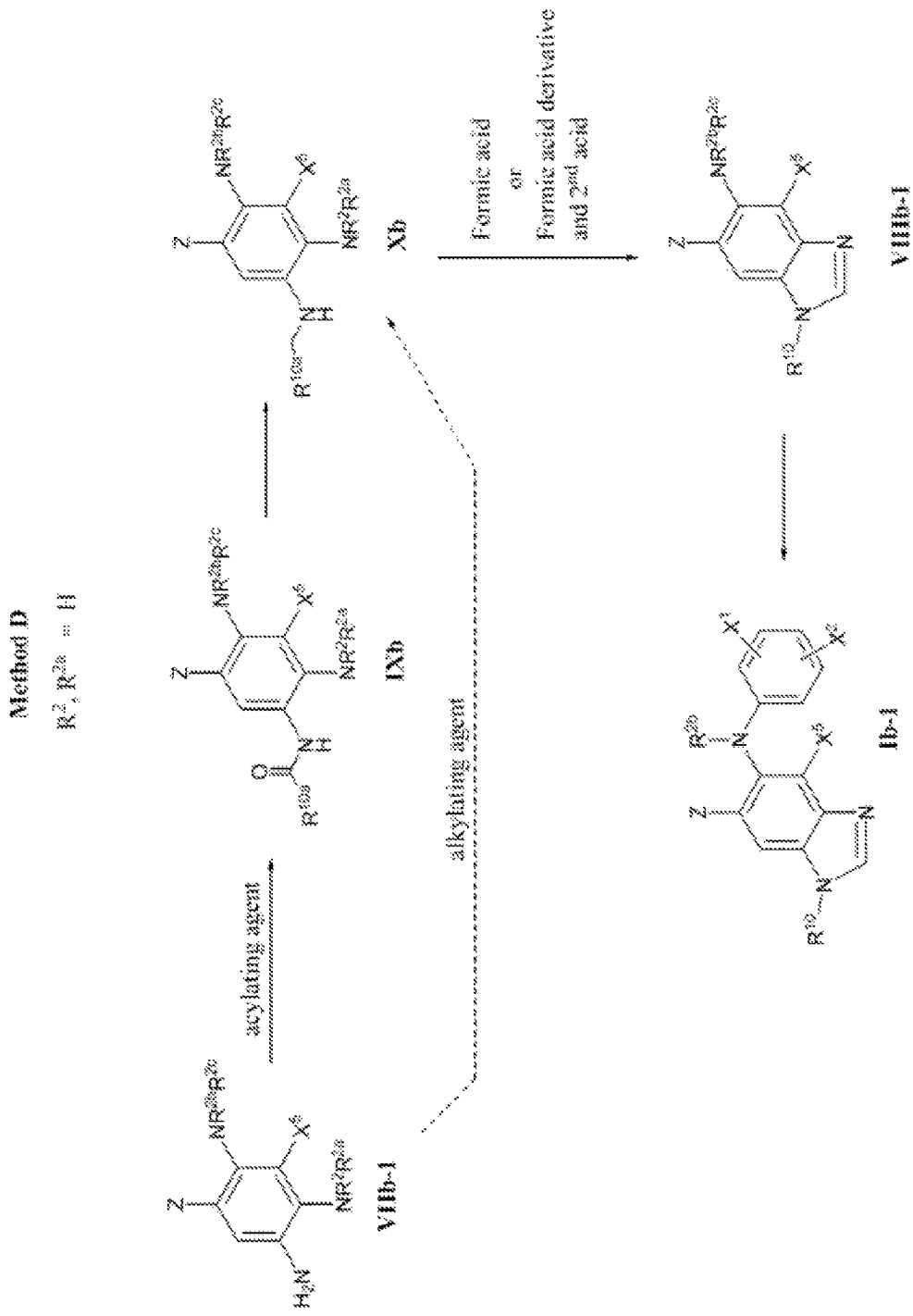
FIG. 9 shows an alternative multi-step cyclization method (Method D) for the preparation of benzimidazole core structures represented by Formula Ib-1.

Method D:

According to another embodiment, an N-3 benzimidazole derivative represented by Formula VIIIb-1, wherein $R^{10}$ is not hydrogen, can be prepared from a compound of Formula VIIb-1 in a stepwise manner as shown in FIG. 9. More specifically, Method D comprises treating a compound of Formula VIIb-1, wherein $R^2$ and $R^{2a}$ are hydrogen, with a suitable acylating agent such as, but not limited to, formic acid, an acid anhydride (for example acetic anhydride), an acid halide (for example acetyl chloride) or an ester (for example trifluoroethyl formate) to provide the intermediate compound represented by Formula IXb

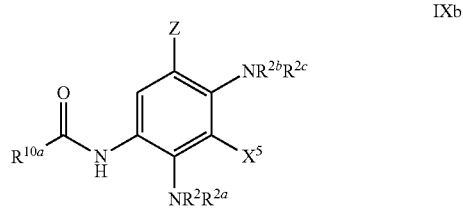

IXb wherein Z, $R^2$, $R^{2a}$ and $X^5$ are as defined herein and $R^{10a}$ is H, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl, and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$.

The amide group of the compound of Formula IXb is then reduced to provide an intermediate compound represented by Formula Xb

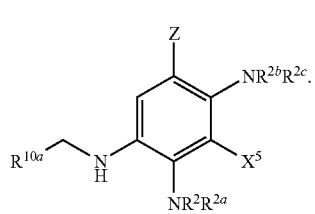

Xb

Suitable reducing agents include, but are not limited to, borane-type reducing agents (e.g., $BH_3$.THF) in an appropriate solvent such as THF. Alternatively, compounds of Formula Xb can be formed directly from a compound of Formula VIIb-1 by reaction with an alkylating agent of formula $R^{10a}CH_2X$, wherein X is a leaving group such as Cl, Br, I, OMs, OTs, OTf, etc. Examples of alkylating agents include alkyl halides such as ethyl iodide. Cyclization of the compound of Formula Xb to provide the benzimidazole represented by Formula VIIIb-1

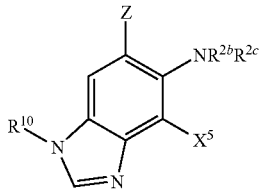

VIIIb-1 wherein $R^{10}$ is not hydrogen, is accomplished by reacting the compound of Formula Xb with (i) formic acid optionally in the presence of an additional acid or (ii) a formic acid derivative (for example, esters of formic acid such as, but not limited to, trimethylorthoformate, triethylorthoformate and formamidine acetate) in the presence of an acid under appropriate conditions known to those skilled in the art to provide a compound of Formula VIIIb-1. The compound of Formula VIIIb-1 can be reacted with an aryl halide as described in Method 1 to provide an N–3 benzimidazole compound of Formula Ib-1.

Figure 10:
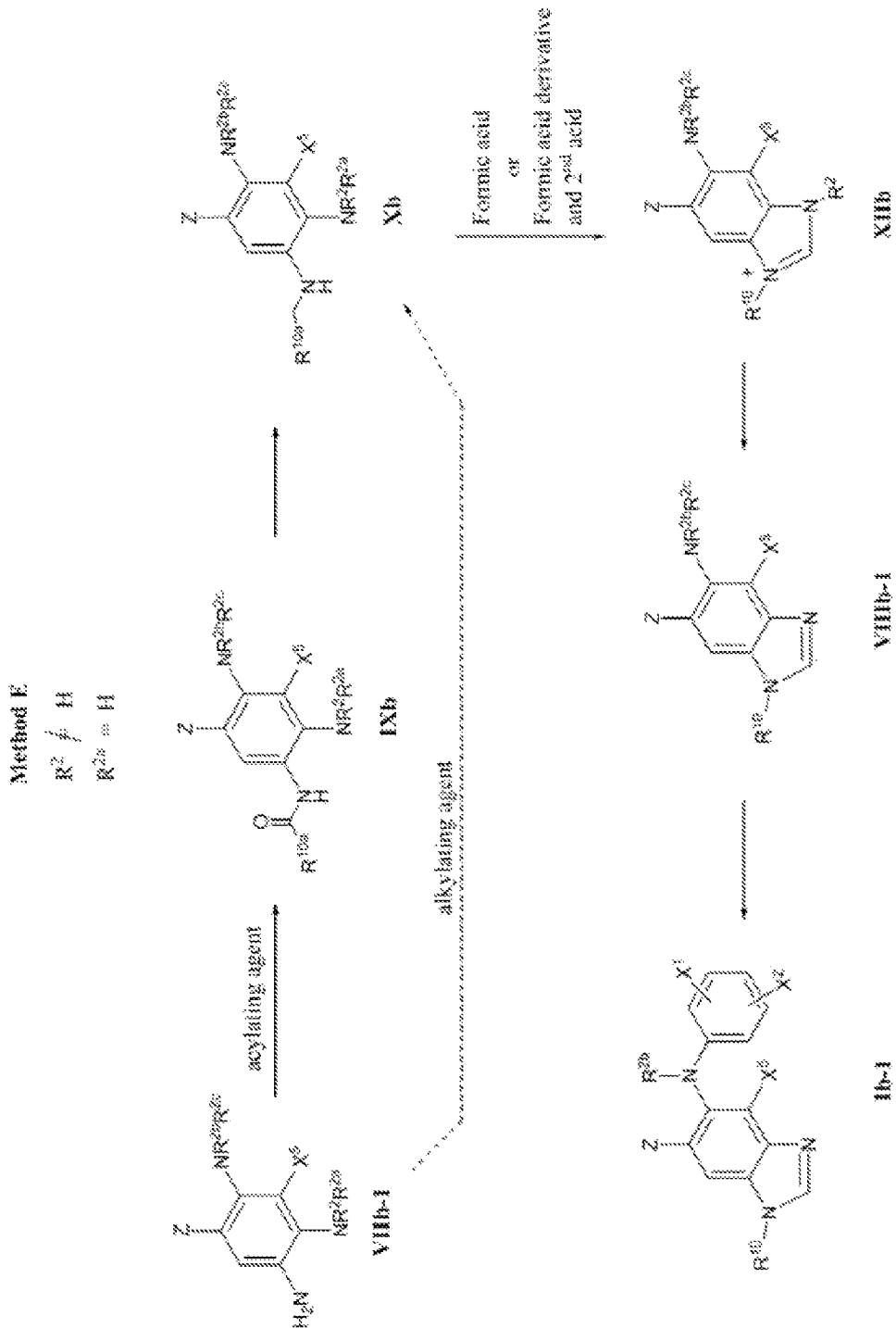
FIG. 10 shows yet another multi-step cyclization method (Method E) for the preparation of benzimidazole core structures represented by Formula Ib-1.

Method E:

In an alternative multi-step cyclization method, referred to herein as Method E as shown in FIG. 10, a compound of Formula VIIb-1, wherein $R^{2a}$ is hydrogen and $R^2$ is not hydrogen, can be cyclized to the corresponding benzimidazole compound of Formula VIIIb-1, wherein $R^{10}$ is not hydrogen, by a step-wise method comprising:

(a) reacting a compound of Formula VIIb-1

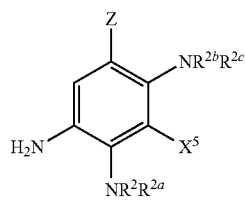

VIIb-1 with a suitable acylating agent to provide a compound of Formula IXb

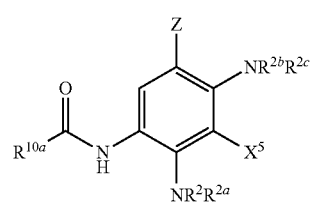

IXb wherein Z, $R^2$, $R^{2a}$ and $X^5$ are as defined herein and $R^{10a}$ is H, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$;

(b) reducing the amide group of said compound of Formula IXb to provide a compound of Formula Xb

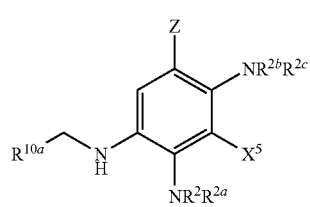

Xb wherein Z, $R^2$, $R^{2a}$, $R^{2b}$, $R^{2c}$, $R^{10a}$ and $X^5$ are as defined herein;

(c) reacting said compound of Formula Xb with (i) formic acid optionally in the presence of an additional acid or (ii) a formic acid derivative (for example, esters of formic acid such as, but not limited to, trimethylorthoformate, triethylorthoformate and formamidine acetate) in the presence of an acid to provide said compound of Formula XIIb-1

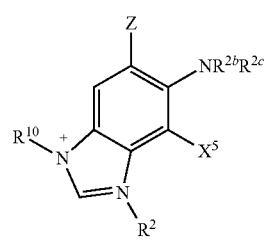

XIIb-1 wherein Z, $R^2$, $R^{2b}$, $R^{2c}$, $R^{10}$ and $X^5$ are as defined herein; and removing the $R^2$ group using methods such as those described in Method B to provide the N–3 benzimidazole compound of Formula VIIIb-1. The compound of Formula VIIIb-1 can be reacted with an aryl halide as described in Method 1 to provide an N–3 benzimidazole compound of Formula Ib-1. Alternatively, according to another embodiment of Method E, a compound of Formula Xb may be obtained by reaction of VIIb-1 with an alkylating agent of the formula $R^{10a}CH_2L$, wherein L is a leaving group, such as Cl, Br, I, OMs, OTs, OTf, etc.

The above-described cyclization Methods A-E of the present invention offer several advantages over conventional methods for the preparation of benzimidazole derivatives. First, there are only a few literature examples of the conversion of a diamino aryl compound to a benzimidazole (see, for example, G. P. Ellis, R. T. Jones, *J. Chem. Soc., Perkin I*, 1974, 903; G. T. Morgan, W. A. P. Challenor, *J. Chem. Soc. Trans.*, 1921, 1537; N. S. Zefirov, G. A. Sereda, V. P. Volkov, S. E. Tkachenko, N. V. Zyk, *ECHET98: Electronic Conference on Heterocyclic Chemistry*, (1988) 406-408; V. Milata, D. Ilaysky, *Organic Proc. And Prep. Int.*, (1993), 25:703-704), however, none of the reported examples involved highly substituted substrates such as those involved in the process of the present invention. In addition, in many of the literature examples the regioselectivity is uncertain (G. T. Morgan, W. A. P. Challenor, *J. Chem. Soc. Trans.*, 1921, 1537), and none of the methods prior to the present invention utilize a substrate having a third amino substituent on the aromatic ring, which has the potential to react with the formaldehyde, leading to the formation of alternative products. Furthermore, the methods of this invention are more suitable for industrial applications, since it uses reagents that are less toxic than the HCl/HCHO reagent mixture used in conventional methods, and therefore do not generate toxic by-products such as dichloromethyl ether.

The terms "$C_1$-$C_{10}$ alkyl" and "alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "$C_2$-$C_{10}$ alkenyl" and "alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "$C_2$-$C_{10}$ alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The terms "carbocycle," "carbocyclyl," "cycloalkyl" and "$C_3$-$C_{10}$ cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl and di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "heterocyclyl" refer to a saturated or partially unsaturated carbocyclic radical of 3 to 8 ring atoms in which at least one ring atom is a heteroatom selected from nitrogen, oxygen and sulfur, the remaining ring atoms being C, wherein one or more ring atoms may be optionally substituted independently with one or more substituent described below. The radical may be a carbon radical or heteroatom radical. The term further includes bicyclic and tricyclic fused ring systems, which include a heterocycle fused one or more carbocyclic or heterocyclic rings. "Heterocycloalkyl" also includes radicals wherein heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl and di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6- or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl. Spiro moieties are also included within the scope of this definition. Heteroaryl groups are optionally mono-, di-, or trisubstituted with, e.g., halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also as defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

The term "halogen" represents fluorine, bromine, chlorine, and iodine.

In general, the various moieties or functional groups of any of the compounds of the present invention may be optionally substituted by one or more substituents. Examples of substituents suitable for purposes of this invention include, but are not limited to, oxo (with the proviso that it is not on an aryl or heteroaryl), halogen, cyano, nitro, trifluoromethyl, difluoromethoxy, trifluoromethoxy, azido, —OR', —NR'SO$_2$R'''', —SO$_2$NR'R''', —C(O)R', —C(O)OR', —OC(O)R', —NR'C(O)OR'''', —NR'C(O)R''', —C(O)NR'R''', —SR', —S(O)R'''', —SO$_2$R'''', —NR'R''', —NR'C(O)NR''R''', —NR'C(NCN)NR''R''', aryl, heteroaryl, arylalkyl, heteroarylalkyl, heterocyclyl and heterocyclylalkyl, where R', R'', R''' and R'''' are independently lower alkyl, lower alkenyl, or lower alkynyl.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain compounds prepared according to a process of the present invention can exist as two or more tautomeric forms. Tautomeric forms of the compounds may interchange, for example, via enolization/de-enolization and the like. Accordingly, the present invention includes the preparation of all tautomeric forms of compounds of Formulas Ia-1, Ib-1, VIIIa-1 and VIIIb-1 wherein $R^{10}$ is hydrogen.

This invention also encompasses compounds of Formulas Ia-1, Ib-1, Ic-1, III, VI, VIIa-1, VIIb-1, VIIIa-1, VIIIb-1, XIa and XIb

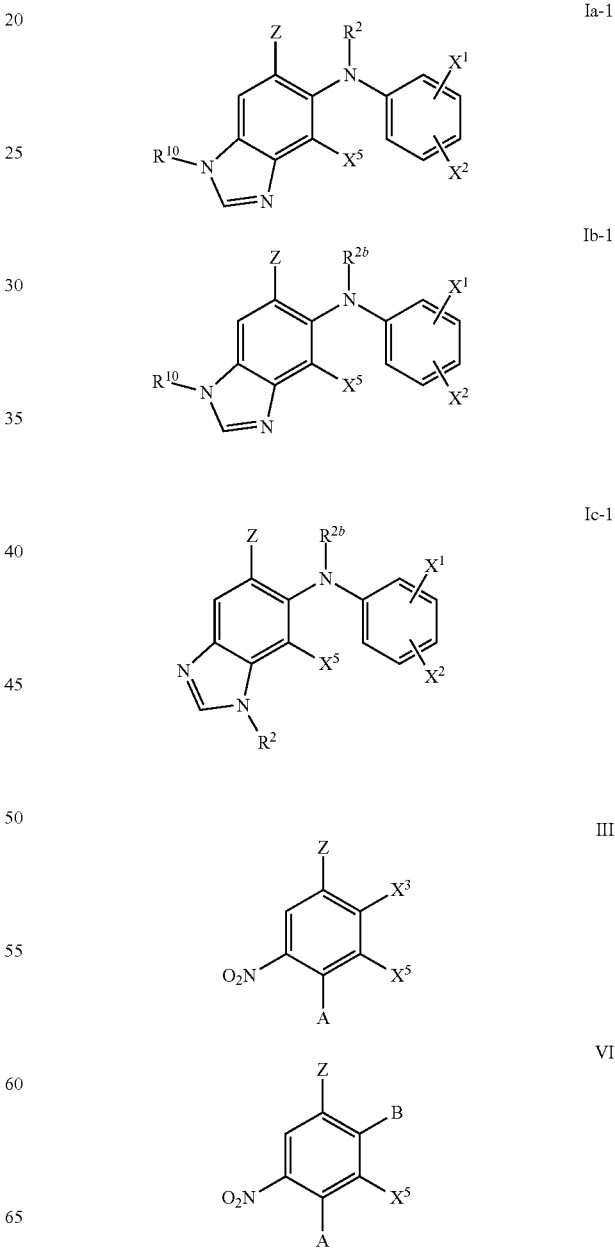

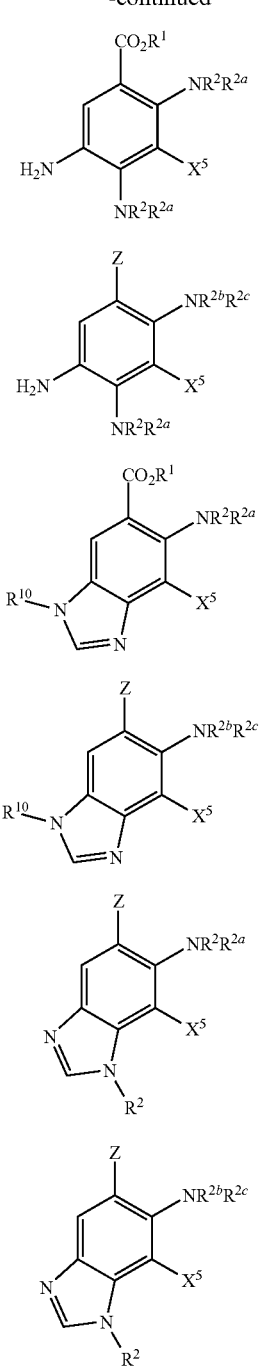

wherein Z, $R^1$, $R^2$, $R^{2a}$, $R^{2b}$, $R^{2c}$, $R^{10}$, $X^1$, $X^2$, $X^3$, $X^5$, A, and B are as defined herein. In certain embodiments, Z is —C(=O)$NR^6R^7$. In certain embodiments, $R^8$ is $C_1$-$C_{10}$ alkyl optionally substituted with OH, O—($C_1$-$C_6$-alkyl) or —O—($C_1$-$C_{10}$-alkenyl). In certain embodiments, $R^8$ is —$(CH_2)_2$—OH. In particular embodiments, Z is —C(=O)NH$(CH_2)_2$—OH. In other embodiments, Z is —COO$R^1$ and $R^1$ is $C_1$-$C_{10}$ alkyl. In particular embodiments, $R^1$ is methyl.

In certain embodiments, $X^5$ is halogen. In particular embodiments, $X^5$ is F. In certain embodiments, $X^1$ is H or halogen and $X^2$ is alkyl or halogen. In certain embodiments, $X^1$ is Br and $X^2$ is Cl.

In certain embodiments, $R^{10}$ is $C_1$-$C_{10}$ alkyl. In particular embodiments, $R^{10}$ is methyl. In certain embodiments, $R^2$, $R^{2a}$, $R^{2b}$ and $R^{2c}$ are hydrogen.

This invention further includes solvates of compound of Formula Ia-1, Ib-1, Ic-1, III, VI, VIIa-1, VIIb-1, VIIIa-1, VIIIb-1, XIa and XIb. The term "solvate" refers to an aggregate of a compound of this invention with one or more solvent molecules.

This invention also encompasses salts of compounds of Formula Ia-1, Ib-1, Ic-1, III, VI, VIIa-1, VIIb-1, VIIIa-1, VIIIb-1, XIa and XIb. That is, a compound of the invention may possess a sufficiently acidic, a sufficiently basic, or both functional groups, and accordingly react with any of a number of inorganic or organic bases, and inorganic and organic acids, to form a salt. Examples of salts include those salts prepared by reaction of the compounds of the present invention with a mineral or organic acid or an inorganic base, such salts including sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates and mandelates. Since a single compound of the present invention may include more than one acidic or basic moieties, the compounds of the present invention may include mono, di or tri-salts in a single compound.

If the inventive compound is a base, the desired salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The inventive compounds may be prepared using the reaction routes and synthesis schemes as described herein, employing the techniques available in the art using starting materials that are readily available or can be synthesized using methods known in the art.

Representative compounds of the present invention, which are encompassed by the present invention include, but are not limited to, the compounds of the examples and the acid or base addition salts thereof. The examples presented below are intended to illustrate particular embodiments of the invention, and are not intended to limit the scope of the specification or the claims in any way.

EXAMPLES

The example and preparations provided below further illustrate and exemplify the compounds of the present invention and methods of preparing such compounds. It is to be understood that the scope of the present invention is not limited in any way by the scope of the following examples and preparations. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the example described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H-NMR spectra were recorded on a Varian instrument operating at 400 MHz. $^1$H-NMR spectra were obtained as CDCl$_3$ or d$_6$ DMSO solutions (reported in ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

Synthesis of 6-(4-bromo-2-chlorophenylamino)-7-fluoro-3-methyl-3H-benzoimidazole-5-carboxylic acid

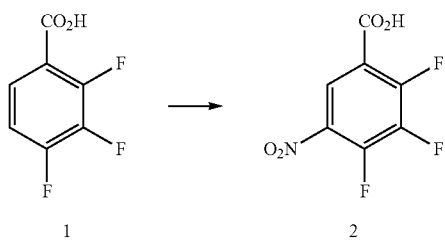 [SMILES: O=C(O)c1ccc(F)c(F)c1F ; O=C(O)c1cc([N+](=O)[O-])c(F)c(F)c1F]

Step 1: 2,3,4-Trifluoro-5-nitrobenzoic acid (2)

Fuming HNO$_3$ 90% (549.0 g, 7.84 mol corrected for 90% wt, 1.26 equiv.) was added to 2.0 L (3.35 kg) of concentrated H$_2$SO$_4$ over 18 minutes with stirring. The solution of HNO$_3$ was then added to a mixture of 2,3,4-trifluorobenzoic acid (1094 g, 6.21 mol, 1 equiv.) in 3.3 L (5.85 kg) of concentrated H$_2$SO$_4$ in a second flask with ice-water bath cooling over an hour. Upon complete addition, the reaction mixture was allowed to warm to room temperature. After 5 hours, the reaction was complete by HPLC and the reaction mixture (brown solution) was poured over 10 minutes into a mechanically stirred mixture of 10.6 kg of distilled water and 11.8 kg of ice. The yellow slurry was cooled to 14° C., stirred for 2 hours and then filtered. The cake was rinsed with 4.0 L of distilled water and then with 5 L of heptane. The wet cake was oven-dried overnight. The crude solids (1.791 kg) were then stirred in 16 L of distilled water (9 vol.), filtered and oven-dried at 55° C. under high vacuum overnight to yield 1035.9 g (75%) of compound 2 as a yellowish solid. HPLC was 98 a % (220 nm) and 100% (254 nm). $^1$H NMR (400 MHz, d$_6$ DMSO) δ 8.44 (1H, apparent dt, J 1.9, 7, Ar—H). $^{19}$F NMR (376 MHz, d$_6$ DMSO) δ −153.9, −131.5, −120.9. $^{13}$C NMR (100 MHz, d$_6$ DMSO) δ 117 (C, m), 124 (CH, b s), 134 (C, s), 141 (C—F, dt, J 251, 10), 148 (C—F, dd, J 265, 13), 154 (C—F, dd, J 265, 10), 163 (COOH). IR ν$_{max}$/cm$^{-1}$ 3108 (br), 1712, 1555, 1345, 1082. MS APCI (−) m/z 220 (M−1) detected.

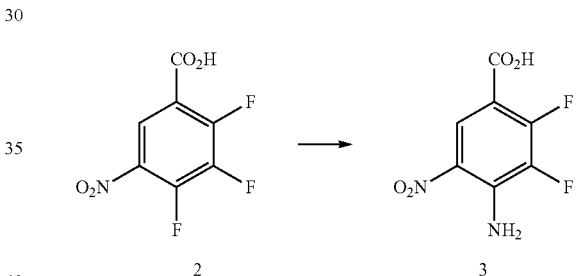

Step 2: 4-Amino-2,3-difluoro-5-nitrobenzoic acid (3)

To a mixture of 2,3,4-trifluoro-5-nitrobenzoic acid (2) (167.2 g, 0.756 mol, 1 equiv) in 400 mL of distilled water was added concentrated ammonium hydroxide (28% NH$_3$ solution; 340 g, 380 mL, 4.23 mol, 5.6 equiv.) ensuring that internal temperature was below 6.0° C. over 2-2.5 hours. The mixture was stirred for 50 minutes and then warmed to room temperature for 3-4 hours. When the reaction was >90% complete by HPLC, the reaction mixture was cooled in an ice-water bath and concentrated HCl (350 mL) was then added dropwise to adjust pH=2. The slurry was stirred for 1 hour with ice bath cooling and filtered. The cake was rinsed with 1 L of distilled water and then with 350 mL of MTBE. The cake was oven-dried at 48° C. overnight to give 134.9 g of a yellow solid. HPLC was 83.6 a % (220 nm) and 96.96 a % (254 nm). The MTBE filtrate was concentrated on a rotary evaporator and pumped overnight to give 9.9 g of a second crop as a yellow solid: HPLC was 81.1 a % (220 nm) and 95.40 a % (254 nm). Combined yield of 4-amino-2,3-difluoro-5-nitrobenzoic acid (3) was 144.8 g (88%). $^1$H NMR (400 MHz, d$_6$ DMSO) δ 8.0 (2H, br s, NH$_2$) 8.42 (1H, dd, J 1.5, 7.6, Ar—H). $^{19}$F NMR (376 MHz, d$_6$ DMSO) δ −153.9, −129.0. $^{13}$C NMR (100 MHz, d$_6$ DMSO) δ 106 (C, d, J 10), 126 (CH), 128 (C), 140 (C—F, dd, J 241, 16), 140.8 (C, dd, J 12, 4), 153 (C—F, dd, J 263, 11), 164 (COOH). IR $v_{max}$/cm$^{-1}$ 3494, 3383, 1697, 1641, 1280. MS APCI (−) m/z 217 (M−1) detected.

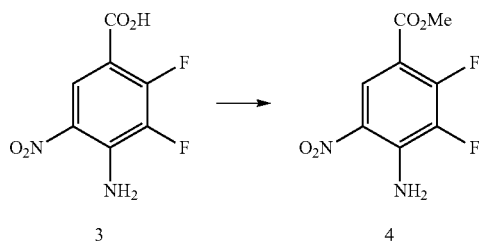 [SMILES: Nc1c([N+](=O)[O-])cc(C(=O)O)c(F)c1F ; COC(=O)c1cc([N+](=O)[O-])c(N)c(F)c1F]

Step 4: Methyl 4-amino-2,3-difluoro-5-nitrobenzoate (4)

TMSCl (132 g, 1.21 mol, 2.0 equiv) was added over 5 minutes to a slurry of 4-amino-2,3-difluoro-5-nitrobenzoic acid (3) (132.3 g, 0.607 mol, 1 equiv) in 325 mL of MeOH. The mixture was heated at reflux for 15 hours. Once the reaction was complete by HPLC, the reaction mixture was cooled in an ice-water bath for 45 minutes. Then the reaction mixture was filtered and the cake was washed with 65 mL of MeOH. The wet cake was dried overnight at 55° C. under high vacuum to provide 128.8 g (92%) of 4-amino-2,3-difluoro-5-nitrobenzoic acid methyl ester (4). HPLC was 97.9 a % (220 nm) and 99.2 a % (254 nm). $^1$H NMR (400 MHz, d$_6$ DMSO) δ 3.84 (3H, s, OMe), 8.1 (2H, br s, NH$_2$), 8.43 (1H, apparent dd, J 1.9, 7.2, Ar—H). $^{19}$F NMR (376 MHz, d$_6$ DMSO) δ −153.6, −129.2. $^{13}$C NMR (100 MHz, d$_6$ DMSO) δ 52 (CH$_3$O), 105 (C, d, J 10), 125 (CH, t, J 2.7), 128 (CH, d, J 5), 140 (C—F, dd, J 244, 15), 141 (C, dd, J 14, 5), 152 (C—F, dd, J 263, 11), 162 (COO, t, J 3). IR $v_{max}$/cm$^{-1}$ 3433, 3322, 1699, 1637, 1548, 1342, 1234. MS APCI (−) m/z 231 (M−1) detected.

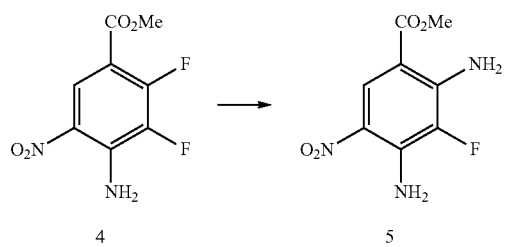 [SMILES: COC(=O)c1cc([N+](=O)[O-])c(N)c(F)c1F ; COC(=O)c1cc([N+](=O)[O-])c(N)c(F)c1N]

Step 5: Methyl 2,4-diamino-3-fluoro-5-nitrobenzoate (5)

To a stirred solution of methyl 4-amino-2,3-difluoro-5-nitrobenzoate (4) (33.0 g, 142.15 mmol) in 1,4-dioxane (165 mL, 1.93 moles), in a 250 mL glass pressure vessel, was added an aqueous solution of ammonia (39 g, 711 mmol, 42.9 mL, 16.5 M). The vessel was then heated in an immersion bath at a bath temperature between 79 and 105° C., for 80 minutes, over which time the internal pressure ranged between 0.2 and 2.7 bar. The pressure was then released slowly and the mixture was treated with water (330 mL, 10 vol). The resultant suspension was stirred for 20 minutes and then filtered under vacuum, and the solid was washed with water (33 mL, 1 vol). The solid was sucked dry, then dried in a vacuum oven at 50° C. to provide methyl 2,4-diamino-3-fluoro-5-nitrobenzoate (5) (32.6 g, 92% yield) as a yellow solid. $^1$H NMR (500 MHz, d$_6$ DMSO) δ 3.83, (3H, s, OMe), 7.20 (2H, br, NH$_2$), 7.37 (2H, br, NH$_2$), 8.47 (1H, s, Ar—H). $^{13}$C NMR (100 MHz, d$_6$ DMSO) δ 52 (CH$_3$), 101 (C), 122 (C), 126 (CH), 134 (C), 137 (C), 142 (C), 166 (C=O). $v_{max}$/cm$^{-1}$ 3474, 3358, 1697, 1633, 1528, 1435, 1317, 1285.

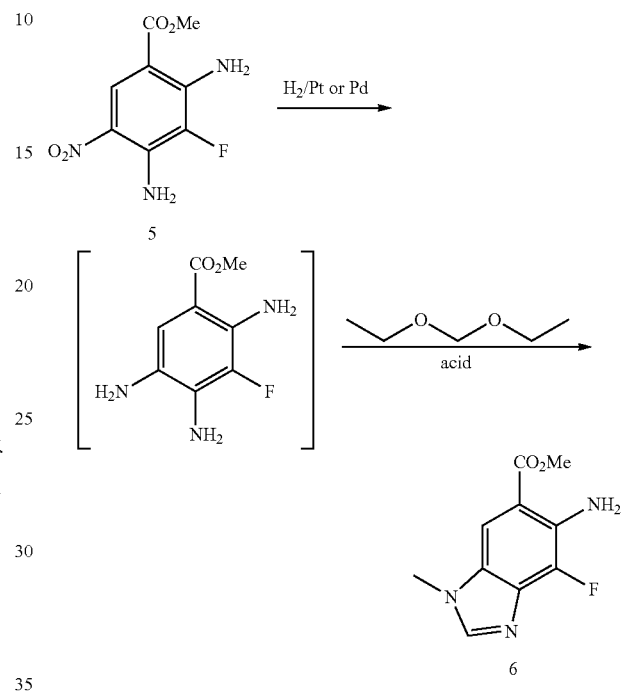

Step 6: 6-Amino-7-fluoro-3-methyl-3H-benzoimidazole-5-carboxylic acid methyl ester (6)

A nitrogen purged hydrogenation vessel was charged with palladium on carbon (5.53 g, 1.30 mmol), and to this was added a solution of methyl 2,4-diamino-3-fluoro-5-nitrobenzoate (5) (100 g, 419 mmol) in tetrahydrofuran (1.3 L) 15.98, followed by methanol (700 mL). The mixture was then stirred, purged with nitrogen, and heated to 55° C. Stirring was then paused while the system was purged with hydrogen (4 bar), and stirring was then recommenced at 750 rpm. After 6.75 hours observable hydrogen uptake had ceased and 29.1 L of hydrogen had been taken up. The system was then purged with nitrogen and allowed to cool to 20° C. HPLC analysis indicated that all starting material had been reacted and that the solution yield of the desired triamine product was approximately 96%. The mixture was then filtered using a Whatman 1μ in-line filter to remove the catalyst and the system was washed with tetrahydrofuran (400 mL). Solvent was then distilled off until a total of 1400 mL had been collected and the mixture was allowed to cool to ambient temperature. Acetonitrile (1.0 L) was added to the mixture, followed by removal of solvent (1 L) by distillation, then two additional 500 mL aliquots of acetonitrile were added, followed each time by removal of solvent (2×500 mL) by distillation.

Following the solvent swap procedure above, the stirred mixture was cooled to 60° C. and a solution of p-toluenesulfonic acid monohydrate (87.7 g, 461 mmol) in acetonitrile (175 mL) and water (7.6 mL, 419 mmol) was added slowly, followed by diethoxymethane (95.98 g, 921.59 mmol). After 3 hours, HPLC analysis indicated incomplete reaction and the temperature was raised to 65° C. for an additional 1 hour, after which time the reaction was complete by HPLC analysis. Pyridine (66.3 g, 838 mmol) was added over 10 minutes and the reaction mixture was cooled to 20° C. over about 30 minutes and held at this temperature for 2.5 hours. The resultant slurry was then filtered and the solid was washed with acetonitrile (2×200 mL), and then dried at 45° C. in a vacuum oven, to provide 73.65 g of 6-amino-7-fluoro-3-methyl-3H-benzoimidazole-5-carboxylic acid methyl ester (6) as a pale brown solid (assay 95.3%), yield at 100%, 75%. $^1$H NMR (400 MHz, d$_6$ DMSO) δ 3.79 (3H, s, NMe), 3.87, (3H, s, OMe), 6.04 (2H, br, NH$_2$), 7.82 (1H, s, ArH), 8.23 (1H, s, Ar—H). $^{13}$C NMR (100 MHz, d$_6$ DMSO) δ 33 (NCH$_3$), 52 (OMe), 110 (CH, d J 5), 111 (C, d J 4), 124 (C, d J 5), 125 (C, d J 14), 136 (C, d J 11), 137 (CF, d J 242), 145 (CH), 167 (C=O). ν$_{max}$/cm$^{-1}$ 3455, 3283, 3166, 3096, 2950, 2361, 2342, 1689, 1608, 1228. MS APCI (+) m/z 224 (M+1) detected.

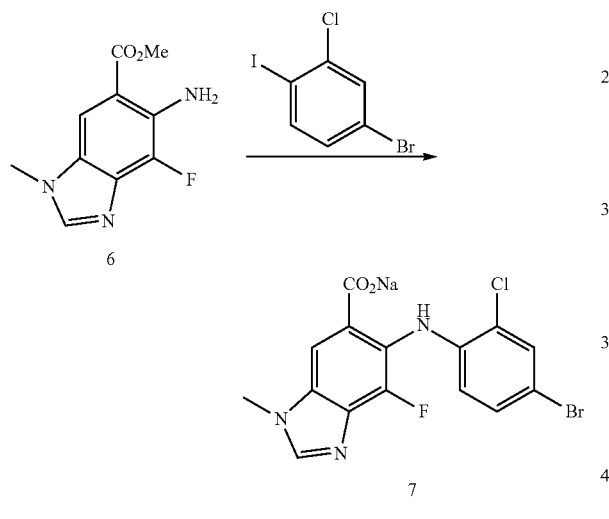

Step 7: 6-(4-Bromo-2-chlorophenylamino)-7-fluoro-3-methyl-3H-benzoimidazole-5-carboxylic acid (Na Salt) (7)

A mixture of Xantphos (1.20 g, 2.05 mmol) and tris(dibenzylideneacetone)dipalladium (0) (1.26 g, 1.37 mmol) in anhydrous anisole (76 mL) was stirred under nitrogen, at 50° C. for 30 minutes to provide a an orange-brown solution of the catalyst.

To a stirred mixture of 6-amino-7-fluoro-3-methyl-3H-benzoimidazole-5-carboxylic acid methyl ester (6) (8.00 g, 34.16 mmol) and cesium carbonate (22.48 g, 68.31 mmol) in anhydrous anisole (76 mL) under nitrogen was added 4-bromo-2-chloroiodobenzene (1.60 g, 1.10 equiv., 4.88 mmol). The preformed catalyst, as prepared above, was then added to the mixture to provide a dark brown suspension, which was heated at 100±2° C., with stirring at 350 rpm. The reaction was monitored by HPLC analysis. After 41 hours, no 6-amino-7-fluoro-3-methyl-3H-benzoimidazole-5-carboxylic acid methyl ester (6) remained. The reaction mixture was cooled to about 80° C. and 1M sulfuric acid (40.99 mL 40.99 mmol) was added. Gas evolution was observed after 10 minutes and the rate of addition was controlled to moderate the effervescence. At the end of the addition the pH was between 7 and 8. Additional sulfuric acid (1M, 10.25 mL, 10.25 mmol) was then added to give mobile slurry with a pH of 0. The mixture was diluted with anisole (20 mL) and Celatom FW-14 filter agent was added. It was then filtered at about 80° C. through a water-wet pad of Celatom FW-14 filter agent and the cake was washed with anisole (1×40 mL+3×20 mL), then water (10 mL). The lower aqueous layer was separated and discarded and the organic layer was washed with 10% aqueous NaCl solution (2×40 mL). This was added to a sodium hydroxide (5.46 g, 68.3 mmol) in methanol (24 mL) and the mixture was heated at 65° C. with stirring. After 17.5 hours HPLC analysis indicated that the hydrolysis of the ester was complete and the slurry was cooled to 15° C., then filtered on a sinter. The solid was washed with water (4×24 mL), MTBE (24 mL), and acetonitrile (2×25 mL) and then dried at 45° C. in a vacuum oven to provide 11.07 g of 6-(4-bromo-2-chlorophenylamino)-7-fluoro-3-methyl-3H-benzoimidazole-5-carboxylic acid (7) as a fine pale brown solid (assay 93.7% by $^1$H NMR), actual wt 10.37 g (72.2% yield). $^1$H NMR (400 MHz, d$_6$ DMSO) δ 3.85 (3H, s, NMe), 6.53 (1H, dd, J 9, 7, Ar—H), 7.27 (1H, dd, J 9, 2.5, Ar—H), 7.56 (1H, d, J 9, Ar—H), 7.97 (1H, s, Ar—H), 8.20 (1H, s, Ar—H), 11.5 (1H, s, CO$_2$H). $^{13}$C NMR (100 MHz, d$_6$ DMSO) δ 31 (CH$_3$), 108 (CH, d, J 2), 109 (CH), 117 (C, d, J 6), 122 (C), 124 (C, d, J 7), 127 (C), 130 (C), 131 (C), 132 (C, d, J 9), 133 (C, d, J 11), 141 (C), 145 (CF, d, J 252), 146 (CH), 170 (C=O).

Example 1A

Synthesis of 6-(4-bromo-2-chlorophenylamino)-7-fluoro-3-methyl-3H-benzoimidazole-5-carboxylic acid, Na salt

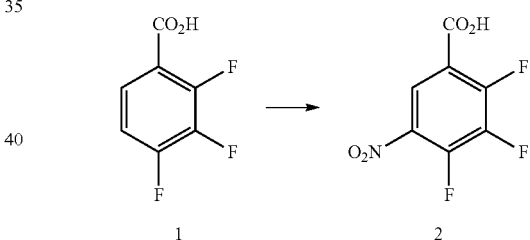

Step 1: 2,3,4-Trifluoro-5-nitrobenzoic acid (2)

To a stirred solution of 2,3,4-Trifluorobenzoic acid (70 Kg, 398 Mol) in sulphuric acid (96 wt %; 194 L) and hexamethyldisiloxane (6.5 Kg, 40 Mol), at 23° C., was added a 1:1 mixture of sulphuric acid (96 wt %) and nitric acid (98 wt %) (total 70.1 Kg), over 75 min. The temperature of the reaction mixture was maintained between 15 and 25° C. during the addition. The mixture was stirred for a further 5 hours and then run onto ice (700 Kg), keeping the temperature of the ice mixture below 0° C. Water (35 L) was used to rinse the nitration reactor into the quench reactor and the obtained mixture was stirred for 2 hours at 0° C., then isolated on a centrifuge. The resultant wet cake was washed with cold water (350 L), and the solid was then suspended in water (280 L) and stirred for 2 hours at 0° C. This suspension was then centrifuged and the cake was washed with cold water (210 L), then dried in a vacuum oven at 45° C. for 2 days, to provide 2,3,4-Trifluoro-5-nitro benzoic acid (69.4 Kg, 74.3% yield). $^1$H NMR (400 MHz, d$_6$ DMSO) δ 8.44 (1H, apparent dt, J 2, 7, Ar—H). $^{19}$F NMR (376 MHz, d$_6$ DMSO) δ −153.9, −131.5, −120.9. $^{13}$C NMR (100 MHz, d$_6$ DMSO) δ 117 (C, m), 124 (CH, b s), 134 (C, s), 141 (C—F, dt, J 251, 10), 148 (C—F, dd, J 265, 13), 154 (C—F, dd, J 265, 10), 163 (COOH). IR $v_{max}$/cm$^{-1}$ 3108 (br), 1712, 1555, 1345, 1082. MS APCI (−) m/z 220 (M−1) detected.

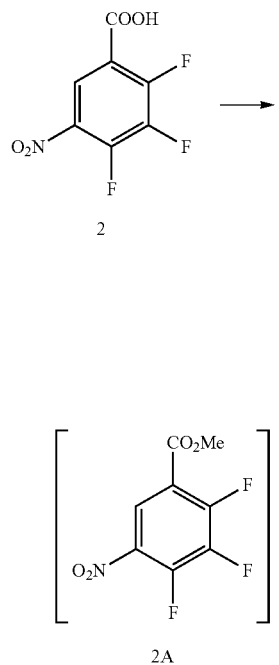

Step 2: Methyl 2,4-diamino-3-fluoro-5-nitrobenzoate (5)

2,3,4-Trifluoro-5-nitrobenzoic acid (100 g, 0.452 Mol) was dissolved in methanol (60 mL) at 25-30° C. To the resulting stirred solution, at 10° C., was added chlorotrimethylsilane (98.3 g, 0.91 Mol, 2 equiv.), maintaining the temperature between 10 and 20° C. On completion of the addition the mixture was heated at reflux for 5 hours. At this point 99% (area) conversion to methyl 2,3,4-trifluoro-5-nitrobenzoate (2) was indicated by HPLC analysis. After cooling the mixture to room temperature it was diluted with N-methylpyrrolidone (NMP, 380 mL) and the reaction vessel was placed in an ice-bath. Ammonium hydroxide solution (33 wt % [d 0.88], 164 mL, 144 g, 2.7 Mol) was added to the vigorously stirred mixture, keeping the temperature below 15° C. A yellow precipitate was formed during the addition. The reactor was then closed and heated at 80° C., with an internal pressure of 2.5 barg. After 5 hour the reaction mixture was cooled to 60° C. and the pressure was released. The temperature was then increased to 75° C., followed by addition of ammonium hydroxide (33 wt % [d 0.88] in water, 53 mL, 47 g. 1.0 Mol). The mixture was then cooled to 50° C. over 90 min. during with time a yellow precipitate was formed. After a further 1 hour at 50° C. water (400 mL) was added over 1 hour and the resulting suspension was cooled to 25° C. and filtered. The filter cake was washed once with 1:1 NMP/water (540 mL), once with water (540 mL) and then dried in a vacuum oven at 50° C. for 24 hours, to provide methyl 2,4-diamino-3-fluoro-5-nitrobenzoate 4) (91 g, 88% yield).

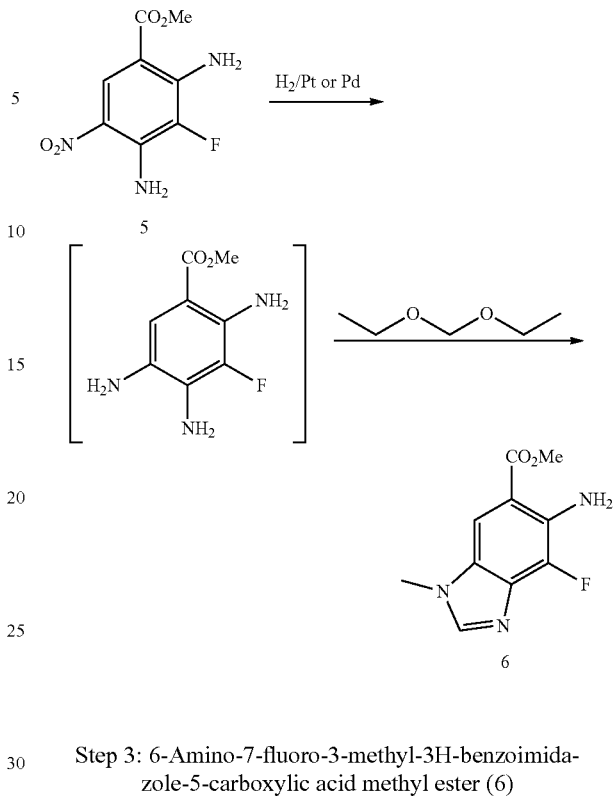

Step 3: 6-Amino-7-fluoro-3-methyl-3H-benzoimidazole-5-carboxylic acid methyl ester (6)

A nitrogen purged hydrogenation vessel was charged with palladium on carbon (5.53 g, 1.30 mmol), and to this was added a solution of methyl 2,4-diamino-3-fluoro-5-nitrobenzoate (5) (100 g, 419 mmol) in tetrahydrofuran (1.3 L) 15.98, followed by methanol (700 mL). The mixture was then stirred, purged with nitrogen, and heated to 55° C. Stirring was then paused while the system was purged with hydrogen (4 bar), and stirring was then recommenced at 750 rpm. After 6.75 hours observable hydrogen uptake had ceased and 29.1 L of hydrogen had been taken up. The system was then purged with nitrogen and allowed to cool to 20° C. HPLC analysis indicated that all starting material had been reacted and that the solution yield of the desired triamine product was approximately 96%. The mixture was then filtered using a Whatman 1μ in-line filter to remove the catalyst and the system was washed with tetrahydrofuran (400 mL). Solvent was then distilled off until a total of 1400 mL had been collected and the mixture was allowed to cool to ambient temperature. Acetonitrile (1.0 L) was added to the mixture, followed by removal of solvent (1 L) by distillation, then two additional 500 mL aliquots of acetonitrile were added, followed each time by removal of solvent (2×500 mL) by distillation.

Following the solvent swap procedure above, the stirred mixture was cooled to 60° C. and a solution of p-toluenesulfonic acid monohydrate (87.7 g, 461 mmol) in acetonitrile (175 mL) and water (7.6 mL, 419 mmol) was added slowly, followed by diethoxymethane (95.98 g, 921.59 mmol). After 3 hours, HPLC analysis indicated incomplete reaction and the temperature was raised to 65° C. for an additional 1 hour, after which time the reaction was complete by HPLC analysis. Pyridine (66.3 g, 838 mmol) was added over 10 minutes and the reaction mixture was cooled to 20° C. over about 30 minutes and held at this temperature for 2.5 hours. The resultant slurry was then filtered and the solid was washed with acetonitrile (2×200 mL), and then dried at 45° C. in a vacuum oven, to provide 73.65 g of 6-amino-7-fluoro-3-methyl-3H-benzoimidazole-5-carboxylic acid methyl ester (6) as a pale brown solid (assay 95.3%), yield at 100%, 75%. $^1$H NMR (400 MHz, d$_6$ DMSO) δ 3.79 (3H, s, NMe), 3.87, (3H, s, OMe), 6.04 (2H, br, NH$_2$), 7.82 (1H, s, ArH), 8.23 (1H, s, Ar—H). $^{13}$C NMR (100 MHz, d$_6$ DMSO) δ 33 (NCH$_3$), 52 (OMe), 110 (CH, d J 5), 111 (C, d J 4), 124 (C, d J 5), 125 (C, d J 14), 136 (C, d J 11), 137 (CF, d J 242), 145 (CH), 167 (C=O). $v_{max}/cm^{-1}$ 3455, 3283, 3166, 3096, 2950, 2361, 2342, 1689, 1608, 1228. MS APCI (+) m/z 224 (M+1) detected.

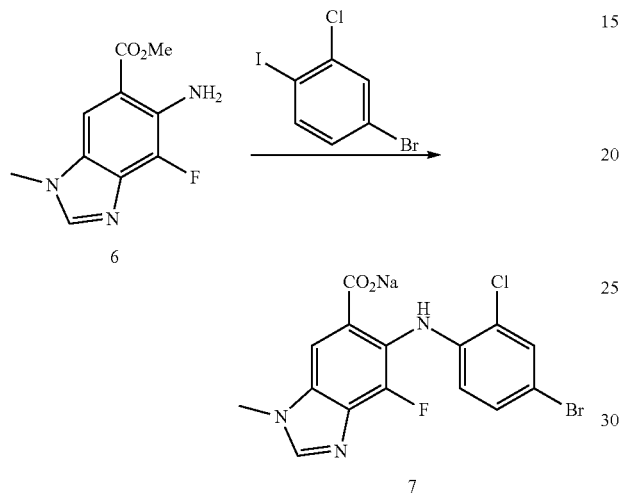

Step 4: 6-(4-Bromo-2-chlorophenylamino)-7-fluoro-3-methyl-3H-benzoimidazole-5-carboxylic acid (Na Salt) (7)

A mixture of Xantphos (1.95 g, 3.36 mmol) and tris(dibenzylideneacetone)dipalladium (0) (1.23 g, 1.34 mmol) in anisole (135 mL) was stirred under nitrogen, at 50° C. for 30 minutes to provide a brown solution of the catalyst.

To a stirred mixture of 6-amino-7-fluoro-3-methyl-3H-benzoimidazole-5-carboxylic acid methyl ester (6) (15.01 g, 67.2 mmol) and cesium carbonate (43.79 g, 134.4 mmol) in anisole (150 mL) under nitrogen was added 4-bromo-2-chloroiodobenzene (23.5 g, 1.10 equiv., 74.0 mmol). The preformed catalyst, as prepared above, was then added to the mixture, followed by an anisole (15 mL) line wash, to provide a dark brown suspension, which was heated at 90° C., with stirring at 400 rpm. The reaction was monitored by HPLC analysis. After 14 hours, no 6-amino-7-fluoro-3-methyl-3H-benzoimidazole-5-carboxylic acid methyl ester (6) remained. The reaction mixture was diluted with anisole (75 mL) and cooled to about 80° C. 1M aqueous sulfuric acid (108 mL 108 mmol) was added, gas evolution and an endotherm was observed and the rate of addition was controlled to moderate the effervescence and maintain the temperature above 75° C. At the end of the addition the pH was 0. Harbolite filter agent (3.75 g) was added to the biphasic mixture and the mixture was stirred for 20 minutes. It was then filtered at about 80° C. through a pad of Harbolite filter agent and the cake was washed with hot (80° C.) anisole (2×75 mL). The lower aqueous layer was separated and discarded and the organic layer was washed with 10% aqueous NaCl solution (2×75 mL).

Silicycle Siliabond Si-Thiourea (5.00 g) was added to the organic layer to provide a fine suspension, which was stirred at 80° C. After 2 hours the mixture was filtered through glass fiber filter paper (GF/C) at 80° C., to provide a clear orange-brown solution, which was cooled to 55° C. To the solution, was added methanol (45 mL) and water (2.7 mL 2.2 equiv.). A mixture of methanol (15 mL) and sodium methoxide in methanol 30% w/w (24.22 g 2.0 equiv.) was added to the organic solution over a period of 1 hour, to provide a beige slurry. After 2 hours HPLC analysis indicated that the hydrolysis of the ester was complete and water (75 mL) was added to the mixture over a period of 2 hours. The resultant slurry was then filtered and solid was washed with water (3×45 mL) then dried at 45° C. in a vacuum oven, to provide 6-(4-bromo-2-chlorophenylamino)-7-fluoro-3-methyl-3H-benzoimidazole-5-carboxylic acid Na salt (7) as a beige solid (22.9 g, [assay 95.0% by $^1$H NMR, actual wt 21.8 g], 77.0% yield). $^1$H NMR (400 MHz, d$_6$ DMSO) δ 3.85 (3H, s, NMe), 6.53 (1H, dd, J 9, 7, Ar—H), 7.27 (1H, dd, J 9, 2.5, Ar—H), 7.56 (1H, d, J 9, Ar—H), 7.97 (1H, s, Ar—H), 8.20 (1H, s, Ar—H), 11.5 (1H, s, CO$_2$H). $^{13}$C NMR (100 MHz, d$_6$ DMSO) δ 31 (CH$_3$), 108 (CH, d, J 2), 109 (CH), 117 (C, d, J 6), 122 (C), 124 (C, d, J 7), 127 (C), 130 (C), 131 (C), 132 (C, d, J 9), 133 (C, d, J 11), 141 (C), 145 (CF, d, J 252), 146 (CH), 170 (C=O).

Example 2

Synthesis of 6-(4-Bromo-2-chlorophenylamino)-7-fluoro-3-methyl-3H-benzoimidazole-5-carboxylic acid methyl ester (11)

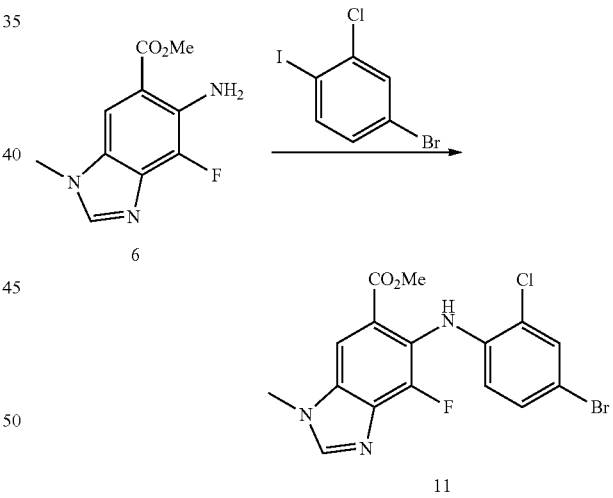

A solution of Pd(OAc)$_2$ (0.777 g, 3.46 mmol, 0.04 equiv.) and Xantphos (3.0 g, 5.19 mmol, 0.06 equiv.) in toluene (300 mL), under N$_2$ was stirred for 20 minutes and then added to a slurry of 6-amino-7-fluoro-3-methyl-3H-benzoimidazole-5-carboxylic acid methyl ester (6) (19.3 g, 86.5 mmol, 1 equiv.), bromochloroiodobenzene (30.2 g, 95.1 mmol, 1.1 equiv.) and Cs$_2$CO$_3$ (particle size=20 microns or less; 51 g, 156 mmol, 1.8 equiv.) in toluene (200 mL), over 15 minutes at about 50° C. The mixture was then heated at reflux for 29 hours, after which no starting material remained by HPLC analysis. After allowing the mixture to cool to ambient it was filtered through an M frit and the solid was washed with toluene (95 mL), then dried in a vacuum oven at 50° C. overnight. The solid was then suspended in water (784 mL) and 2N aqueous HCl (174 mL) was added slowly, over about 15 minutes to control bubbling. The resultant slurry was stirred at room temperature for 2 hours, then filtered through an M frit funnel (150 mL). The solid product was washed with water (3×87 mL) and dried in a vacuum oven at 45° C., to provide 6-(4-bromo-2-chlorophenylamino)-7-fluoro-3-methyl-3H-benzoimidazole-5-carboxylic acid methyl ester (11) 25.6 g (92 wt % by HPLC, corrected mass=23.6 g, 66% yield). $^1$H NMR (400 MHz, $d_6$ DMSO) δ 3.84 (3H, s, NMe), 3.93 (3H, s, OMe), 6.44 (1H, dd, J 8.8, 5.1, Ar—H), 7.28 (1H, dd, J 2, 9.8, Ar—H), 7.64 (1H, d J 2.1, Ar—H), 8.1 (1H, s, NH) 8.14 (1H, s, Ar—H), 8.5 (1H, s, Ar—H); δ $^{19}$F (376 MHz, $d_6$ DMSO) −133; $^{13}$C NMR (100 MHz, $d_6$ DMSO) δ 32 (MeN), 52 (MeO), 109.4 (C), 109.7 (CH), 115.7 (CH), 119.1 (C), 120.7 (C), 122.5 (C, d, J 10), 130.4 (CH), 131.0 (CH), 133.4 (C, d, J 10), 135.5 (C, d, J 16), 140.8 (C), 146.0 (C—F, d, J 252), 148.6 (CH), 166.7 (COO); $v_{max}$/cm$^{-1}$ 3401, 1700, 1506, 1274; m/z 412 and 414 (M+ and M+2) detected with MS APCI (+).

Example 3

Methyl 2,4,5-triamino-3-fluorobenzoate (9)

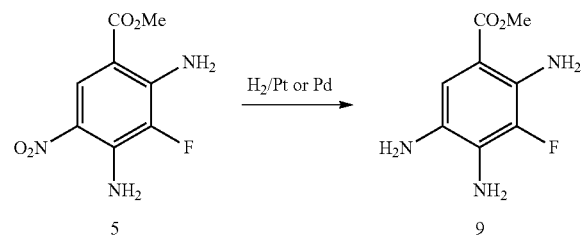 [SMILES: COC(=O)c1cc([N+](=O)[O-])c(N)c(F)c1N ; COC(=O)c1cc(N)c(N)c(F)c1N]

A mixture of methyl 2,4-diamino-3-fluoro-5-nitrobenzoate (5) (40.0 g, 173.7 mmol) and 5% Pd/C (3.0 g, Type 487; 0.4 mol % Pd relative to starting material), in methanol (300.0 mL) and tetrahydrofuran (300.0 mL) was stirred at 2000 RPM, under hydrogen (~3.5 bar), at 50° C. in a 1.5 L hydrogenation vessel. After 6 hours the vessel was purged with nitrogen and HPLC analysis indicated that no starting material remained. The mixture was then filtered under nitrogen pressure and the filter washed through with THF (160 mL), to give a clear yellow solution. The solvent was removed by rotary evaporation, to provide methyl 2,4,5-triamino-3-fluorobenzoate (9) 37.5 g (93.3% w/w by NMR) as a solid, yield ~100%. $^1$H NMR (400 MHz, $d_6$ DMSO) δ 3.69 (3H, s, NMe), 4.20 (2H, br s, NH$_2$), 5.24 (2H, br s, NH$_2$), 5.70 (2H, br s, NH$_2$), 6.83 (1H, d, J 1, Ar—H). $^{13}$C NMR (100 MHz, $d_6$ DMSO) δ 51 (CH$_3$), 98 (C, d, J 5), 110 (CH, d, J 2), 125 (C, d, J 6), 131 (C, d, J 12), 133 (C, d, J 12), 139 (CF, d, J 225), 166 (C=O). vmax/cm−1 3480, 3461, 3373, 3356, 3280, 3163, 1679, 1655, 1314. MS APCI (+) m/z 200 (M+1) detected.

Example 4

Synthesis of 6-(4-bromo-2-chlorophenylamino)-7-fluoro-3-methyl-3H-benzoimidazole-5-carboxylic acid (10) (Copper-Catalyzed Aryl Coupling Method)

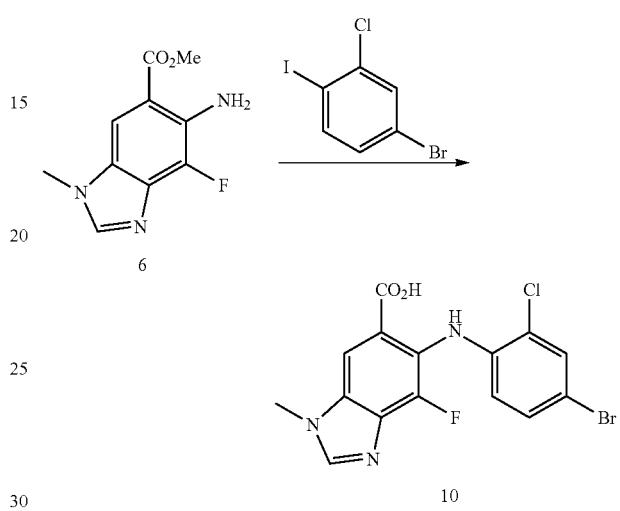

A mixture of methyl 6-amino-7-fluoro-3-methyl-3H-benzoimidazole-5-carboxylate (6) (1.0 g, 4.4 mmol), copper iodide (85.3 mg, 443.5 μmol) and isopropanol (10.0 mL, 130.8 mmol) was stirred at 40° C. for 15 minutes. Potassium carbonate (1.2 g, 8.9 mmol) and ethylene glycol (551 mg, 8.9 mmol) were then added and the mixture was heated at reflux for 1 hour under a Dean-Stark trap. An additional charge of isopropanol (1.5 mL) was added, followed by 4-bromo-2-chloroiodobenzene (1.5 g, 4.4 mmol) in isopropanol (2 mL) over 1 hour. After 26 hours, HPLC analysis showed that 81% of the benzimidazole substrate had been converted into 6-(4-Bromo-2-chlorophenylamino)-7-fluoro-3-methyl-3H-benzoimidazole-5-carboxylic acid (10).

Example 5

Synthesis of 6-Amino-7-fluoro-3H-benzoimidazole-5-carboxylic acid methyl ester (12)

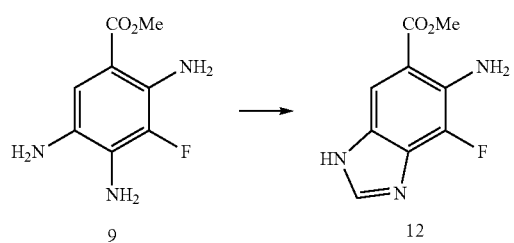 [SMILES: COC(=O)c1cc(N)c(N)c(F)c1N ; COC(=O)c1cc2[nH]cnc2c(F)c1N]

To a stirred solution of methyl 2,4,5-triamino-3-fluorobenzoate (9) (7.58 g, 38.1 mmol) in THF (152 mL, 20 vol) was added triethyl orthoformate (20.3 g, 22.8 mL, 137.0 mmol), followed by dropwise addition of H$_2$SO$_4$ (9.33 g, 18 M, 94.1 mmol). The mixture was then heated at 60° C. for 6 hours, at which point no starting material was detected by HPLC analysis. The solid product was filtered and rinsed with THF (150 mL, 20 vol), then transferred to a reaction vessel, suspended in water (150 mL) and the resulting mixture was neutralized to about pH 7.5 with 2 N NaOH. After stirring for 30 minutes, the suspension was filtered and the solid product was dried in a vacuum oven at 55° C., overnight to provide 6-amino-7-fluoro-3H-benzoimidazole-5-carboxylic acid methyl ester (12) 7.5 g, 94% yield (100% area by HPLC). $^1$H NMR (400 Hz, d$_6$ DMSO) δ 3.53 (1H, br s, NH), 3.85, (3H, s, OMe), 6.10 (2H, br s, NH$_2$), 7.90 (1H, s, Ar—H), 7.20 (1H, s, Ar—H). MS APCI (+) m/z 210 (M+1) detected with MS APCI (+).

Example 6

Synthesis of 2,4-Diamino-3-fluoro-5-nitrobenzoic acid (13)

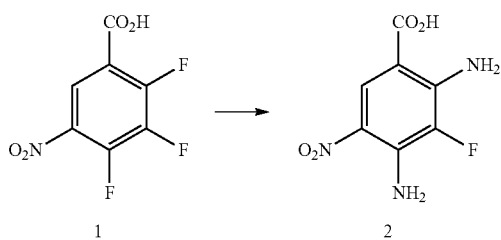 [SMILES: O=C(O)c1cc([N+](=O)[O-])c(F)c(F)c1F ; Nc1c(C(=O)O)cc([N+](=O)[O-])c(N)c1F]

A suspension of 2,3,4-trifluoro-5-nitrobenzoic acid (1) (5 g) and ammonium hydroxide (7.7 grams, 25 wt % NH$_3$ in H$_2$O, 4.9 equivalents) in N-methylpyrrolidinone (12.5 mL) was heated at 80-90° C. in a sealed reactor. During the reaction the mixture became homogeneous and the pressure rose to 0.4 bar. After 1.75 hours, HPLC analysis showed incomplete conversion and a further charge of ammonium hydroxide (2 g, 25 wt % NH$_3$ in H$_2$O) was added, followed by heating at 80-90° C. in the sealed reactor for an additional 1.5 hours. After this time HPLC analysis indicated >99% conversion and the mixture was allowed to cool to room temperature overnight. The contents of the reactor were then added to water (100 mL), producing a homogeneous, brown solution with a pH of 9.4. Acetic acid was then added to the mixture until the pH was 6. After cooling to 0° C. the product was isolated by filtration and washed with a mixture of water (10 mL) and MeOH (10 mL), then dried in a vacuum oven at 50° C., to provide 4.4 g (86% yield) of 2,4-diamino-3-fluoro-5-nitrobenzoic acid (2) (HPLC purity 99.7 a %). $^1$H NMR (400 MHz, d$_6$ DMSO) δ 7.27 (2H, br s, NH$_2$), 7.31 (2H, br s, NH$_2$), 8.46, (1H, s, Ar—H), 13.10 (1H, br, CO$_2$H). $^{13}$C NMR (100 MHz, d$_6$ DMSO) δ 102 (C), 123 (C), 127 (CH), 136 (d, J 229, CF), 138 (C), 143 (CF), 168 (C=O).

Example 7

Synthesis of Methyl 2,4-Diamino-3-fluoro-5-nitrobenzoate (5)

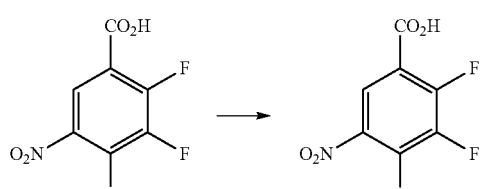

Step 1: 4-Amino-2,3-difluoro-5-nitrobenzoic acid (3)

To a mixture of 2,3,4-trifluoro-5-nitrobenzoic acid (2) (167.2 g, 0.756 mol, 1 equiv) in 400 mL of distilled water was added concentrated ammonium hydroxide (28% NH$_3$ solution; 340 g, 380 mL, 4.23 mol, 5.6 equiv.) ensuring that internal temperature was below 6.0° C. over 2-2.5 hours. The mixture was stirred for 50 minutes and then warmed to room temperature for 3-4 hours. When the reaction was >90% complete by HPLC, the reaction mixture was cooled in an ice-water bath and concentrated HCl (350 mL) was then added drop-wise to adjust pH=2. The slurry was stirred for 1 hour with ice bath cooling and filtered. The cake was rinsed with 1 L of distilled water and then with 350 mL of MTBE. The cake was oven-dried at 48° C. overnight to give 134.9 g of a yellow solid. HPLC was 83.6 a % (220 nm) and 96.96 a % (254 nm). The MTBE filtrate was concentrated on a rotary evaporator and pumped overnight to give 9.9 g of a second crop as a yellow solid: HPLC was 81.1 a % (220 nm) and 95.40 a % (254 nm). Combined yield of 4-amino-2,3-difluoro-5-nitrobenzoic acid (3) was 144.8 g (88%). $^1$H NMR (400 MHz, d$_6$ DMSO) δ 8.0 (2H, br s, NH$_2$) 8.42 (1H, dd, J 1.5, 7.6, Ar—H). $^{19}$F NMR (376 MHz, d$_6$ DMSO) δ −153.9, −129.0. $^{13}$C NMR (100 MHz, d$_6$ DMSO) δ 106 (C, d, J 10), 126 (CH), 128 (C), 140 (C—F, dd, J 241, 16), 140.8 (C, dd, J 12, 4), 153 (C—F, dd, J 263, 11), 164 (COOH). IR ν$_{max}$/cm$^{-1}$ 3494, 3383, 1697, 1641, 1280. MS APCI (−) m/z 217 (M−1) detected.

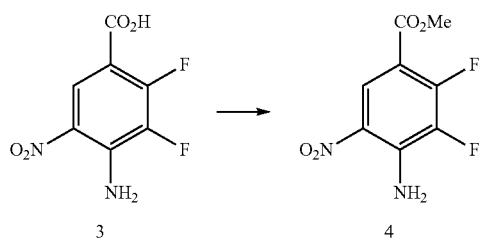 [SMILES: Nc1c([N+](=O)[O-])cc(C(=O)O)c(F)c1F ; COC(=O)c1cc([N+](=O)[O-])c(N)c(F)c1F]

Step 2: Methyl 4-amino-2,3-difluoro-5-nitrobenzoate (4)

TMSCl (132 g, 1.21 mol, 2.0 equiv) was added over 5 minutes to a slurry of 4-amino-2,3-difluoro-5-nitrobenzoic acid (3) (132.3 g, 0.607 mol, 1 equiv) in 325 mL of MeOH. The mixture was heated at reflux for 15 hours. Once the reaction was complete by HPLC, the reaction mixture was cooled in an ice-water bath for 45 minutes. Then the reaction mixture was filtered and the cake was washed with 65 mL of MeOH. The wet cake was dried overnight at 55° C. under high vacuum to provide 128.8 g (92%) of 4-amino-2,3-difluoro-5-nitrobenzoic acid methyl ester (4). HPLC was 97.9 a % (220 nm) and 99.2 a % (254 nm). $^1$H NMR (400 MHz, $d_6$ DMSO) δ 3.84 (3H, s, OMe), 8.1 (2H, br s, $NH_2$), 8.43 (1H, apparent dd, J 1.9, 7.2, Ar—H). $^{19}$F NMR (376 MHz, $d_6$ DMSO) δ −153.6, −129.2. $^{13}$C NMR (100 MHz, $d_6$ DMSO) δ 52 ($CH_3O$), 105 (C, d, J 10), 125 (CH, t, J 2.7), 128 (CH, d, J 5), 140 (C—F, dd, J 244, 15), 141 (C, dd, J 14, 5), 152 (C—F, dd, J 263, 11), 162 (COO, t, J 3). IR $v_{max}$/cm$^{-1}$ 3433, 3322, 1699, 1637, 1548, 1342, 1234. MS APCI (−) m/z 231 (M−1) detected.

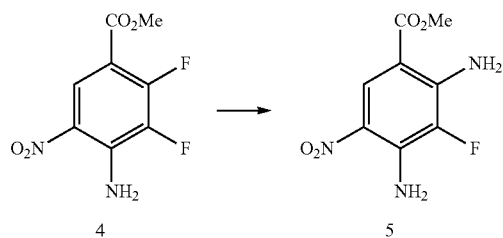 [SMILES: COC(=O)c1cc([N+](=O)[O-])c(N)c(F)c1F ; COC(=O)c1cc([N+](=O)[O-])c(N)c(F)c1N]

Step 3: Methyl 2,4-diamino-3-fluoro-5-nitrobenzoate (5)

To a stirred solution of methyl 4-amino-2,3-difluoro-5-nitrobenzoate (4) (33.0 g, 142.15 mmol) in 1,4-dioxane (165 mL, 1.93 moles), in a 250 mL glass pressure vessel, was added an aqueous solution of ammonia (39 g, 711 mmol, 42.9 mL, 16.5 M). The vessel was then heated in an immersion bath at a bath temperature between 79 and 105° C., for 80 minutes, over which time the internal pressure ranged between 0.2 and 2.7 bar. The pressure was then released slowly and the mixture was treated with water (330 mL, 10 vol). The resultant suspension was stirred for 20 minutes and then filtered under vacuum, and the solid was washed with water (33 mL, 1 vol). The solid was sucked dry, then dried in a vacuum oven at 50° C. to provide methyl 2,4-diamino-3-fluoro-5-nitrobenzoate (5) (32.6 g, 92% yield) as a yellow solid. $^1$H NMR (500 MHz, $d_6$ DMSO) δ 3.83, (3H, s, OMe), 7.20 (2H, br, $NH_2$), 7.37 (2H, br, $NH_2$), 8.47 (1H, s, Ar—H). $^{13}$C NMR (100 MHz, $d_6$ DMSO) δ 52 ($CH_3$), 101 (C), 122 (C), 126 (CH), 134 (C), 137 (C), 142 (C), 166 (C=O). $v_{max}$/cm$^{-1}$ 3474, 3358, 1697, 1633, 1528, 1435, 1317, 1285.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A process for the preparation of a compound of Formula VIIIb-1

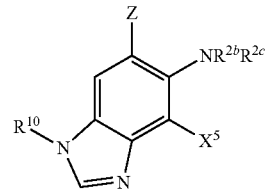

and salts and solvates thereof, wherein:

$Z$ is —C(=O)OR$^1$;

$X^5$ is F, Cl, Br, or I;

$R^1$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from the group consisting of halogen, hydroxyl, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl;

$R^{2b}$ and $R^{2c}$ are independently hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —COR$^6$, —C(O)OR$^6$ or —C(O)NR$^6$R$^7$, wherein said alkyl, alkenyl, alkynyl, and arylalkyl portions are optionally substituted with one or more groups independently selected from the group consisting of halogen, hydroxyl, $C_1$-$C_4$ alkyl, $C_2$-$C_4$ alkenyl, and $C_2$-$C_4$ alkynyl;

$R^6$ and $R^7$ are independently hydrogen, trifluoromethyl, —OR$^8$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^6$ and $R^7$ together with the atom to which they are attached form a 4 to 10 membered heteroaryl or heterocyclic ring, wherein said heteroaryl and heterocyclic rings are optionally substituted with one or more groups independently selected from the group consisting of halogen, trifluoromethyl, difluoromethoxy, trifluoromethoxy and OR$^8$;

$R^8$ is hydrogen, $C_1$-$C_{10}$ alkyl, $C_2$-$C_{10}$ alkenyl, aryl or arylalkyl, wherein said alkyl, alkenyl, aryl and arylalkyl are optionally substituted with one or more groups independently selected from the group consisting of OH, —O—($C_1$-$C_{10}$-alkyl) and O—($C_1$-$C_{10}$-alkenyl); and $R^{10}$ is $C_1$-$C_{10}$ alkyl, $C_3$-$C_{10}$ cycloalkylalkyl, or arylalkyl, wherein said alkyl, cycloalkylalkyl, and arylalkyl, portions are optionally substituted with one or more groups independently selected from the group consisting of halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —NR$^6$R$^7$ and —OR$^8$;

said method comprising cyclizing a compound of Formula VIIb-1

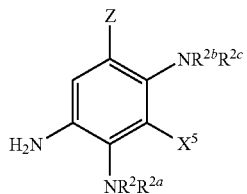

VIIb-1 wherein $R^2$ hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^6$, —$C(O)OR^6$ or —$C(O)NR^6R^7$, wherein said alkyl, alkenyl, alkynyl, benzyl, allyl, and arylalkyl portions are optionally substituted with one or more groups independently selected from the group consisting of halogen, hydroxyl, $C_1$-$C_4$ alkyl, $C_2$-$C_4$ alkenyl, and $C_2$-$C_4$ alkynyl, and $R^{2a}$ is hydrogen, to provide said compound of Formula VIIIb-1.

2. A process for the preparation of a compound of Formula VIIIb-1

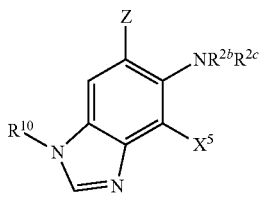

VIIIb-1 and salts and solvates thereof, wherein:

Z is —$C(=O)OR^1$;

$X^5$ is F, Cl, Br, or I;

$R^1$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from the group consisting of halogen, hydroxyl, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl;

$R^{2b}$ is hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —$COR^6$, —$C(O)OR^6$ or —$C(O)NR^6R^7$, wherein said alkyl, alkenyl, alkynyl, and arylalkyl portions are optionally substituted with one or more groups independently selected from the group consisting of halogen, hydroxyl, $C_1$-$C_4$ alkyl, $C_2$-$C_4$ alkenyl and $C_2$-$C_4$ alkynyl;

$R^{2c}$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^6$, —$C(O)OR^6$, —$C(O)NR^6R^7$, —$OR^1$ or —$NHR^1$, wherein said alkyl, alkenyl, alkynyl, benzyl, allyl and arylalkyl portions are optionally substituted with one or more groups independently selected from the group consisting of halogen, hydroxyl, $C_1$-$C_4$ alkyl, $C_2$-$C_4$ alkenyl and $C_2$-$C_4$ alkynyl;

$R^6$ and $R^7$ are independently hydrogen, trifluoromethyl, —$OR^8$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^6$ and $R^7$ together with the atom to which they are attached form a 4 to 10 membered heteroaryl or heterocyclic ring, wherein said heteroaryl and heterocyclic rings are optionally substituted with one or more groups independently selected from the group consisting of halogen, trifluoromethyl, difluoromethoxy, trifluoromethoxy and $OR^8$;

$R^8$ is hydrogen, $C_1$-$C_{10}$ alkyl, $C_2$-$C_{10}$ alkenyl, aryl or arylalkyl, wherein said alkyl, alkenyl, aryl and arylalkyl are optionally substituted with one or more groups independently selected from the group consisting of OH, —O—($C_1$-$C_{10}$-alkyl) and O—($C_1$-$C_{10}$-alkenyl);

$R^{10}$ is $C_1$-$C_{10}$ alkyl, $C_3$-$C_{10}$ cycloalkylalkyl, or arylalkyl, wherein said alkyl, cycloalkylalkyl, and arylalkyl, portions are optionally substituted with one or more groups independently selected from the group consisting of halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$;

said method comprising:

providing a compound of Formula Vb-11 wherein B is $NR^{2b}R^{2c}$ and A is $NR^2R^{2a}$ or $N_3$, or a compound of Formula Vb-12 wherein B is $N_3$ and A is $NR^2R^{2a}$ or $N_3$,

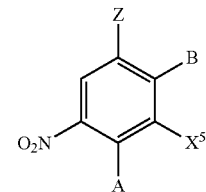

Vb-11: B = $NR^{2b}R^{2c}$, A = $NR^2R^{2a}$ or $N_3$
Vb-12: B = $N_3$, A = $NR^2R^{2a}$ or $N_3$ wherein $R^2$ is hydrogen, substituted or unsubstituted benzyl, allyl or —$C(O)OR^6$ and $R^{2a}$ is hydrogen;

reducing said compound of Formula Vb-11 or Vb-12 to provide a compound of Formula VIIb-1

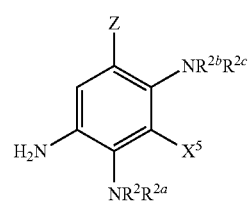

VIIb-1 wherein when A and/or B of Formula Vb-11 or Vb-12 is $N_3$, then $R^2$ and $R^{2a}$ and/or $R^{2b}$ and $R^{2c}$, respectively, of Formula VIIb-1 are hydrogen; and when $R^{2a}$ is hydrogen, cyclizing said compound of Formula VIIb-1 to provide said compound of Formula VIIIb-1.

3. The process of claim 1, wherein said cyclization comprises reacting said compound of Formula VIIb-1, wherein $R^2$ and $R^{2a}$ are H, with (i) formic acid, optionally in the presence of an additional acid, or (ii) a formic acid derivative in the presence of an acid, to provide said compound of Formula VIIIb-1 wherein $R^{10}$ is H.

4. The process of claim 1, wherein said cyclization comprises
   (a) reacting said compound of Formula VIIb-1, wherein $R^{2a}$ is hydrogen and $R^2$ is not hydrogen, with (i) formic acid, optionally in the presence of an additional acid, (ii) a formic acid derivative in the presence of an acid, or (iii) formaldehyde or a formaldehyde derivative in the presence of an acid, to provide a compound of Formula XIb-1

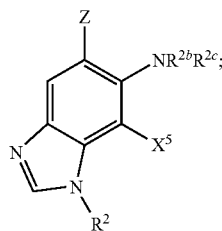

(b) alkylating said compound of Formula XIb-1 with a reagent having the formula $R_{10}$—Y wherein Y is Cl, Br, I, or a sulfonate ester, to provide a compound of Formula XIIb-1

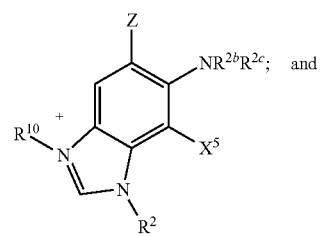

(c) removing said $R^2$ group from the N-1 position to provide said compound of Formula VIIIb-1.

5. The process of claim 1, wherein said cyclization comprises treating said compound of Formula VIIb-1, wherein $R^2$ and $R^{2a}$ are H, with two or more equivalents of formaldehyde or a formaldehyde derivative in the presence of an acid to provide said compound of Formula VIIIb-1 wherein $R^{10}$ is methyl.

6. The process of claim 1, wherein said cyclization comprises:
   (a) reacting said compound of Formula VIIb-1, wherein $R^2$ and $R^{2a}$ are hydrogen, with an acylating agent to provide a compound of Formula IXb

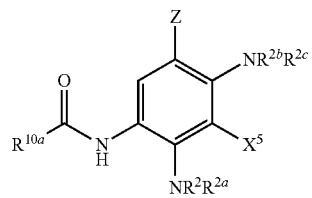

wherein $R^{10a}$ is H, $C_1$-$C_{10}$ alkyl, $C_3$-$C_{10}$ cycloalkylalkyl, or arylalkyl, wherein said alkyl, cycloalkylalkyl, and arylalkyl portions are optionally substituted with one or more groups independently selected from the group consisting of halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$;

(b) reducing the amide group of said compound of Formula IXb to provide a compound of Formula Xb

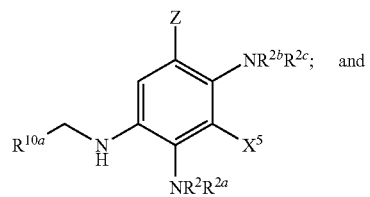

(c) reacting said compound of Formula Xb with (i) formic acid optionally in the presence of an additional acid or (ii) a formic acid derivative in the presence of an acid to provide said compound of Formula VIIIb-1.

7. The process of claim 1, wherein said cyclization comprises:
   (a) reacting said compound of Formula VIIb-1, wherein $R^{2a}$ is hydrogen and $R^2$ is not hydrogen, with an acylating agent to provide a compound of Formula IXb

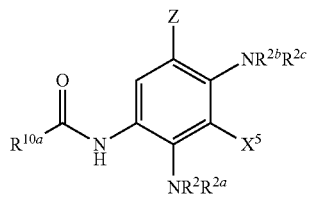

wherein $R^{10a}$ is H, $C_1$-$C_{10}$ alkyl, $C_3$-$C_{10}$ cycloalkylalkyl, or arylalkyl, wherein said alkyl, cycloalkylalkyl, and arylalkyl portions are optionally substituted with one or more groups independently selected from the group consisting of halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$;

(b) reducing the amide group of said compound of Formula IXb to provide a compound of Formula Xb

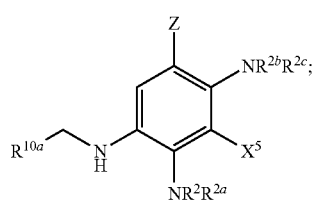

(c) reacting said compound of Formula Xb with (i) formic acid optionally in the presence of an additional acid or (ii) a formic acid derivative in the presence of an acid to provide a compound of Formula XIIb-1

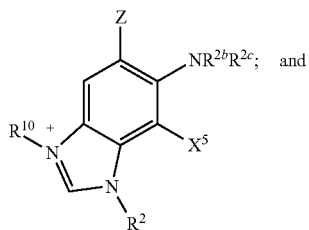

(d) removing the R² group from the N–1 position to provide said compound of Formula VIIIb-1.

8. The process of claim 2, wherein said cyclization comprises (a) reacting said compound of Formula VIIb-1, wherein R²ᵃ is hydrogen and R² is not hydrogen, with (i) formic acid, optionally in the presence of an additional acid, (ii) a formic acid derivative in the presence of an acid, or (iii) formaldehyde or a formaldehyde derivative in the presence of an acid, to provide a compound of Formula XIb-1

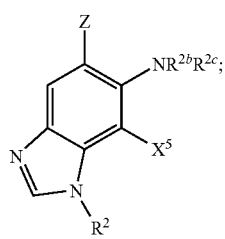

(b) alkylating said compound of Formula XIb-1 with a reagent having the formula R¹⁰—Y wherein Y is Cl, Br, I, or a sulfonate ester, to provide a compound of Formula XIIb-1

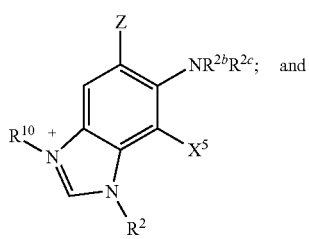

(c) removing said R² group from the N–1 position to provide said compound of Formula VIIIb 1.

9. The process of claim 2, wherein said cyclization comprises treating said compound of Formula VIIb-1, wherein R² and R²ᵃ are H, with two or more equivalents of formaldehyde or a formaldehyde derivative in the presence of an acid to provide said compound of Formula VIIIb-1 wherein R¹⁰ is methyl.

10. The process of claim 2, wherein said cyclization comprises:

(a) reacting said compound of Formula VIIb-1, wherein R² and R²ᵃ are hydrogen, with an acylating agent to provide a compound of Formula IXb

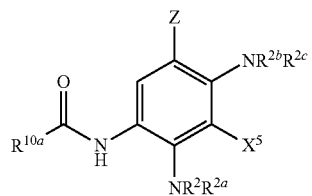

wherein $R^{10a}$ is H, $C_1$-$C_{10}$ alkyl, $C_3$-$C_{10}$ cycloalkylalkyl, or arylalkyl, wherein said alkyl, cycloalkylalkyl, and arylalkyl, portions are optionally substituted with one or more groups independently selected from the group consisting of halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —NR⁶R⁷ and —OR⁸;

(b) reducing the amide group of said compound of Formula IXb to provide a compound of Formula Xb

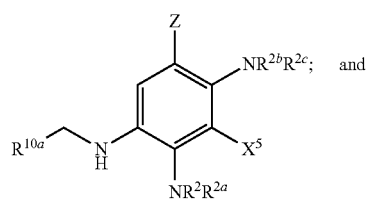

(c) reacting said compound of Formula Xb with (i) formic acid optionally in the presence of an additional acid or (ii) a formic acid derivative in the presence of an acid to provide said compound of Formula VIIIb-1.

11. The process of claim 2, wherein said cyclization comprises:

(a) reacting said compound of Formula VIIb-1, wherein R²ᵃ is hydrogen and R² is not hydrogen, with an acylating agent to provide a compound of Formula IXb

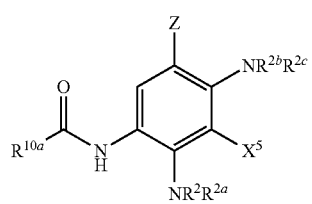

wherein $R^{10a}$ is H, $C_1$-$C_{10}$ alkyl, $C_3$-$C_{10}$ cycloalkylalkyl, or arylalkyl, wherein said alkyl, cycloalkylalkyl, and arylalkyl portions are optionally substituted with one or more groups independently selected from the group consisting of halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —NR⁶R⁷ and —OR⁸;

(b) reducing the amide group of said compound of Formula IXb to provide a compound of Formula Xb

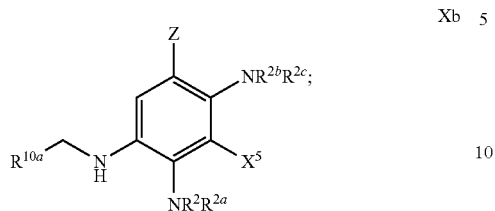

(c) reacting said compound of Formula Xb with (i) formic acid optionally in the presence of an additional acid or (ii) a formic acid derivative in the presence of an acid to provide a compound of Formula XIIb-1

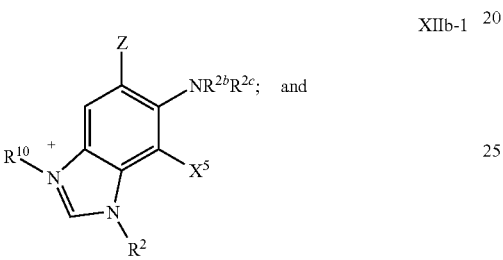

(d) removing the $R^2$ group from the N-1 position to provide said compound of Formula VIIIb-1.

* * * * *

UNITED STATES PATENT AND TRADEMARK OFFICE
CERTIFICATE OF CORRECTION

| | | |
|---|---|---|
| PATENT NO. | : 9,024,040 B2 | Page 1 of 1 |
| APPLICATION NO. | : 13/614941 | |
| DATED | : May 5, 2015 | |
| INVENTOR(S) | : John DeMattei et al. | |

It is certified that error appears in the above-identified patent and that said Letters Patent is hereby corrected as shown below:

In the claims

Column 68, Line 61, In Claim 1, delete "arylalkyl," and insert -- arylalkyl --, therefor.

Column 69, Line 14, In Claim 1, delete "wherein $R^2$ hydrogen" and insert -- wherein $R^2$ is hydrogen --, therefor.

Column 70, Line 20, In Claim 2, delete "arylalkyl," and insert -- arylalkyl --, therefor.

Column 71, Line 27 (Approx.), In Claim 4, delete "$R_{10}$-Y" and insert -- $R^{10}$-Y --, therefor.

Column 73, Line 55, In Claim 8, delete "VIIIb 1." and insert -- VIIIb-1. --, therefor.

Column 74, Lines 13-14, In Claim 10, delete "arylalkyl," and insert -- arylalkyl --, therefor.

Signed and Sealed this
First Day of March, 2016

Michelle K. Lee
*Director of the United States Patent and Trademark Office*